United States Patent
Van Slyke et al.

(10) Patent No.: US 9,186,390 B2
(45) Date of Patent: Nov. 17, 2015

(54) METHODS AND USES OF TIE2 BINDING AND/OR ACTIVATING AGENTS

(75) Inventors: Paul Van Slyke, North York (CA); Daniel Dumont, Oakville (CA)

(73) Assignee: Sunnybrook Health Sciences Center, Toronto (CA)

( * ) Notice: Subject to any disclaimer, the term of this patent is extended or adjusted under 35 U.S.C. 154(b) by 39 days.

(21) Appl. No.: 13/643,171

(22) PCT Filed: Apr. 28, 2011

(86) PCT No.: PCT/CA2011/000473
§ 371 (c)(1),
(2), (4) Date: Oct. 24, 2012

(87) PCT Pub. No.: WO2011/134056
PCT Pub. Date: Nov. 3, 2011

(65) Prior Publication Data
US 2013/0115226 A1    May 9, 2013

Related U.S. Application Data

(60) Provisional application No. 61/328,932, filed on Apr. 28, 2010.

(51) Int. Cl.
| | |
|---|---|
| *A61K 38/08* | (2006.01) |
| *A61K 38/16* | (2006.01) |
| *A61K 38/17* | (2006.01) |
| *A61K 47/48* | (2006.01) |
| *C07K 7/04* | (2006.01) |
| *C07K 7/06* | (2006.01) |
| *C07K 14/475* | (2006.01) |
| *C07K 14/515* | (2006.01) |
| *A61K 38/18* | (2006.01) |
| *A61K 38/39* | (2006.01) |
| *A01K 67/027* | (2006.01) |
| *A61K 48/00* | (2006.01) |

(52) U.S. Cl.
CPC .............. *A61K 38/08* (2013.01); *A01K 67/0275* (2013.01); *A61K 38/17* (2013.01); *A61K 38/1891* (2013.01); *A61K 38/39* (2013.01); *A61K 47/48215* (2013.01); *C07K 14/515* (2013.01); *A01K 2217/052* (2013.01); *A01K 2217/15* (2013.01); *A01K 2217/203* (2013.01); *A01K 2227/105* (2013.01); *A01K 2267/0368* (2013.01); *A01K 2267/0387* (2013.01); *A61K 48/005* (2013.01); *C07K 7/06* (2013.01); *C07K 14/475* (2013.01)

(58) Field of Classification Search
None
See application file for complete search history.

(56) References Cited

U.S. PATENT DOCUMENTS

| 8,507,656 B2 * | 8/2013 | Bedian et al. .............. 530/387.3 |
| 2007/0298996 A1 | 12/2007 | Koh et al. |
| 2011/0097300 A1 | 4/2011 | Van Slyke et al. |

FOREIGN PATENT DOCUMENTS

| WO | 2006/005361 A | 1/2006 |
| WO | 2008/049227 A | 5/2008 |
| WO | 2009/114539 | 3/2009 |
| WO | 2010/010551 | 7/2009 |
| WO | 2010/010551 A | 1/2010 |

OTHER PUBLICATIONS

Skolnick et al. From genes to protein structure and function: novel applications of computational approaches in the genomic era. Trends in Biotech 18(1): 34-39, 2000.*
Bork, A. Powers and pitfalls in sequence analysis: the 70% hurdle. Genome Res 10: 398-400, 2000.*
Doerks et al. Protein annotation: detective work for function prediction. Trends in Genetics 14(6): 248-250, 1998.*
Smith et al. The challenges of genome sequence annotation or "The devil is in the details". Nature Biotech 15: 1222-1223, 1997.*
Brenner, S.E. Errors in genome function. Trends in Genetics 15(4): 132-133, 1999.*
Bork et al. Go hunting in sequence databases but watch out for the traps. Trends in Genetics. 12(10): 425-427, 1996.*
Wells. J.A. Additivity of mutational effects in proteins. Biochemistry 29 (37): 8509-8517, 1990.*
Ngo et al. Computational complexity, protein structure prediction, and the Levinthal paradox. The Protein Folding Problem and Tertiary Structure Prediction, pp. 492-495, 1994.*
Phillips, A., The challenge of gene therapy and DNA delivery. J Pharm Pharmacology 53: 1169-1174, 2001.*
Rubanyi, G.M. The future of human gene therapy. Mol Aspects Med 22: 113-142, 2001.*
Juengst, E.T. What next for human gene therapy? BMJ 326: 1410-1411, 2003.*
Pirollo et al. Targeted delivery of small interfering RNA: approaching effective cancer therapies. Cancer Res 68(5): 1247-1250, 2008.*
Vidal et al Making sense of antisense. Eur J Cancer 41: 2812-2818, 2005.*
David et al. Effects of a synthetic PEG-ylated Tie2 agonist peptide on endotoxemic lung injury and mortality. Am J Physiol Lung Cell Mol Physiol 300: L851-L862, 2011.*
Van Slyke et al. Acceleration of diabetic wound healing by an angiopoietin peptide mimetic. Tissue Engineering: Part A 15(6): 1269-1280, published online Dec. 16, 2008.*

(Continued)

*Primary Examiner* — Bridget E Bunner
(74) *Attorney, Agent, or Firm* — Bereskin & Parr LLP; Melanie Szweras

(57) ABSTRACT

The present disclosure provides methods and uses of Tie2 binding and/or activating agents. In particular, the present disclosure provides methods and uses for inhibiting the expansion of colony forming unit-granulocytes, reducing eosinophils and/or basophils, for treating allergic disease or response or eosinophil/basophil associated condition and for reducing inflammatory cytokine and/or chemokine levels.

26 Claims, 31 Drawing Sheets

(56) References Cited

OTHER PUBLICATIONS

Tokuriki et al. Stability effects of mutations and protein evolvability. Curr Opin Structural Biol 19: 596-604, 2009.*

Chao et al., "The Role of Inflammation and Blood Cells in Wound Healing" in The ACL Handbook: Knee Biology, Mechanics, and Treatment (2013) New York: Springer Science+Business Media, pp. 73-89.*

Simoes, D.C.M. et al. "Angiopoietin-1 protects against airway inflammation and hyperreactivity in asthma". Am. J. Respir. Crit. Care Med. Mar. 20, 2008. vol. 177, pp. 1314-1321.

Kanazawa, H. et al. "Angiopoietin-2 as a contributing factor of exercise-induced bronchoconstriction in asthmatic patients receiving inhaled corticosteroid therapy". J. Allergy Clin. Immunol. Feb. 2008. vol. 121, pp. 390-395.

Makinde, T. and Agrawal, D.K. "Intra and extravascular transmembrane signalling of angiopoietin-1-Tie2 receptor in health and disease". J. Cell Mol. Med. Jun. 2008. vol. 12, No. 3, pp. 810-828.

Kuroda, K. et al. "Altered expression of angiopoietins and Tie2 endothelium receptor in psoriasis". J. Invest. Dermatol. May 2001. vol. 116, No. 5, pp. 713-720.

Wells, T.N.C. et al. "Chemokine blockers—therapeutics in the making?" TRENDS in Pharmacological Sciences, vol. 27, No. 1, Jan. 2006, pp. 41-47.

Lee, S. et al. "Protective effect of COMP-angiopoietin-1 on cyclosporine-induced renal injury in mice". Nephrol. Dial. Transplant (2008) 23:2784-2794.

Lee, K.S. et al. "Blockade of airway inflammation and hyper-responsiveness by an angiopoietin-1 variant, COMP-Ang1". Experimental and Molecular Medicine, vol. 39, No. 6, 733-745, Dec. 2007.

Dumont, Daniel et al., Vasculotide: A Unique Treatment for Acute Lung Injury, Biellette Therapeutics. York University Biotech Challenge, Executive Summary and presentation, Sep. 21, 2008.

Dumont, Daniel et al., Vasculotide: A Unique Treatment for Acute Lung Injury, Biellette Therapeutics, pp. 1-10. York University Biotech Challenge, Commercialization Plan, Oct. 19, 2008.

Dumont, Daniel et al., Vasculotide, An Angiopoietin Peptide-Mimetic for the Treatment of ALI/ARDS Resulting from: Biological & Chemical Warfare; Radiation; Blast-lung; Penetrating Chest Injury; Septic Shock; H1N1 & H5N1; SARS, Canada—U.S. Partners in Biomedical Conference 2009, Embassy of Canada, Washington, DC, Sep. 15, 2009.

Kim, So Ri et al., Angiopoietin-1 variant, COMP-Ang1 Attenuates Hydrogen Peroxide-Induced Acute Lung Injury, Experimental and Molecular Medicine, vol. 40, No. 3, Jun. 2008, pp. 320-331.

Kümpers, Philipp et al., Systemic Delivery of Recombinant Angiopoietin-1 Ameliorates Multiple-organ Dysfunction Syndrome in Experimental Abdominal Sepsis, Poster, Presented at 8th World Congress on Trauma, Shock, Inflammation and Sepsis, Munich, Germany, Mar. 10, 2010.

Kümpers, Philipp et al., The synthetic Tie2 Agonist Peptide Vasculotide Protects Against Vascular Leakage and Reduces Mortality in Murine Abdominal Sepsis, Critical Care, 2011, 15:R261.

van der Heijden, Melanie et al., The Angiopoietin-Tie2 System as a Therapeutic Target in Sepsis and Acute Lung Injury, Expert Opin. Ther. Targets (2009) 13(1):39-53.

Rubig, Eva et al., The Synthetic Tie2-Agonist Peptide Vasculotide Prevents Intra-Renal Microcirculatory Dysfunction and Improves Survival in Ischemic Acute Kidney Injury, Annual Meeting of the Austrian Society for Intensive Care Medicine and Emergency Medicine (ÖGIAIN) and the German Society for Internal Intensive Care Medicine (DGIIN), Jun. 11-14, 2014, Salzburg, Austria.

York biotech, The Catalyst, vol. 3, Issue 3, Nov. 2008, Newsletter.

Simoes, Davina, C.M. et al., Angiopoietin-1 Protects against Airway Inflammation and Hyperractivity in Asthma. American Journal of Respiratory and Critical Care Medicine, vol. 177, 2008 pp. 1314-1321.

Sunnybrook Research Institute, Magazine, Inventing the Future of Health Care, 2008, pp. 52-53.

Florence T H Wu et al., Vasculotide Reduces Endothelial Permeability and Tumor Cell Extravasation in the Absence of Binding to or Agonistic Activation of Tie2, EMBO Molecular Medicine, Apr. 7, 2015, pp. 1-18.

* cited by examiner

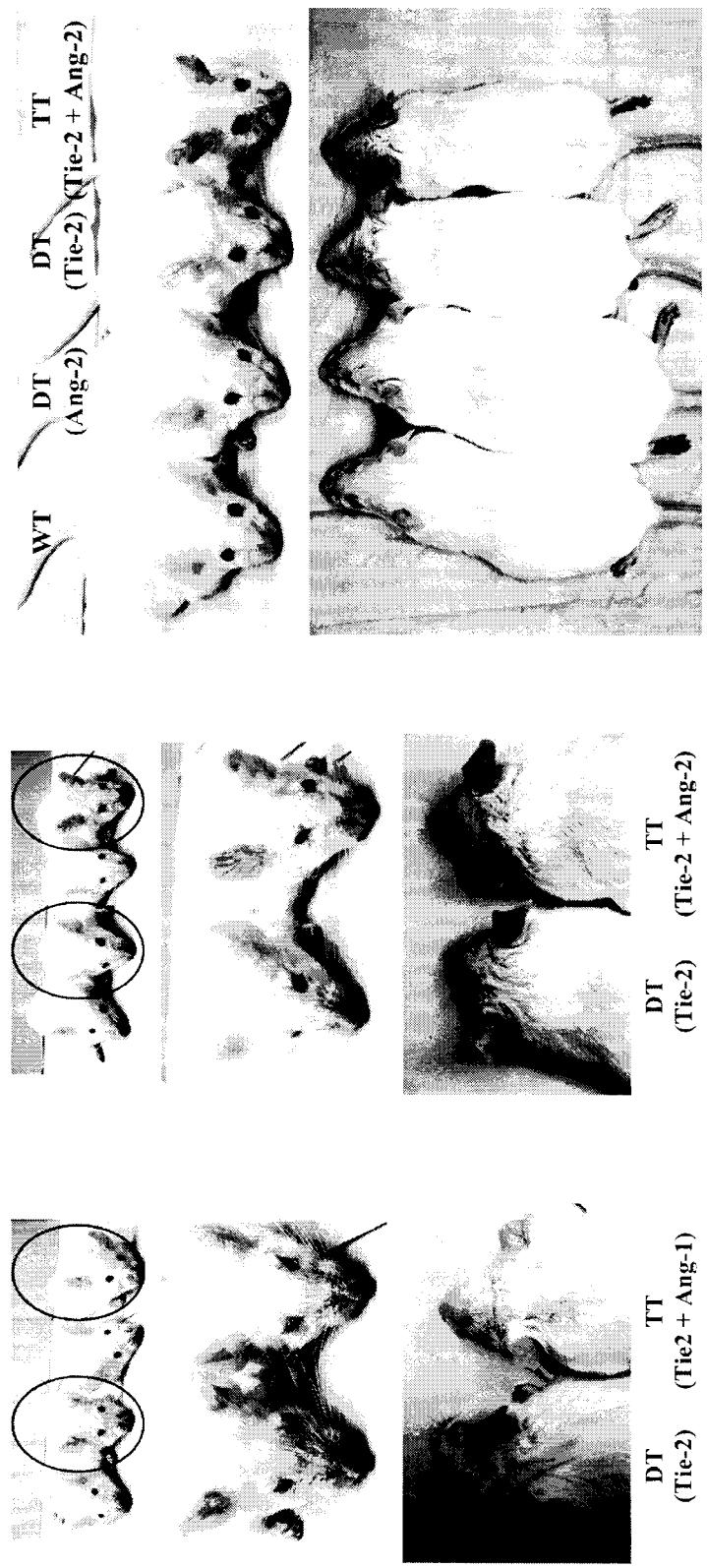

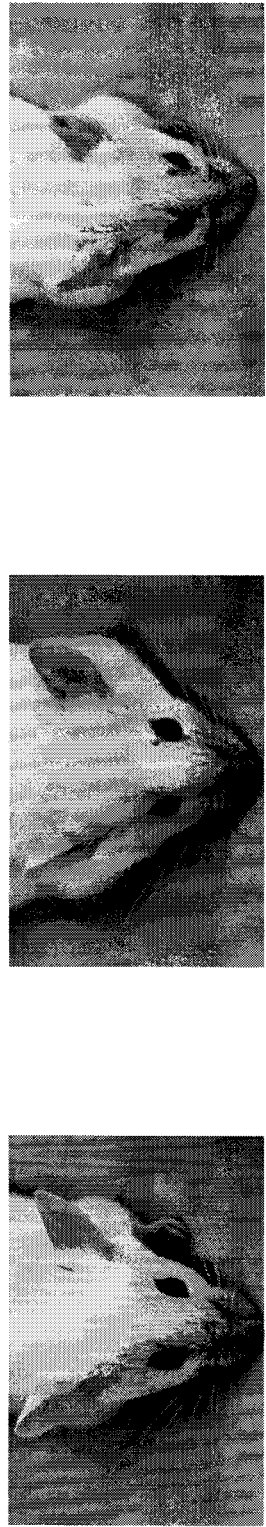

Contol (PBS)

Control (Vasc)

AT-Derm: Severe (PBS)

AT-Derm: Severe (Vasc)

Contol (PBS)

Control (Vasc)

AT-Derm: Severe (PBS)

AT-Derm: Severe (Vasc)

Contol (PBS)

Control (Vasc)

AT-Derm: Severe (PBS)

AT-Derm: Severe (Vasc)

Contol (PBS)

Control (Vasc)

AT-Derm: Severe (PBS)

AT-Derm: Severe (Vasc)

Contol (PBS)

Control (Vasc)

AT-Derm: Severe (PBS)

AT-Derm: Severe (Vasc)

Contol (PBS)

Control (Vasc)

AT-Derm: Severe (PBS)

AT-Derm: Severe (Vasc)

42 days (5 room air controls)
42 days (5 IP immunization only)

whole body
aerosolization
chamber 42 days (4 PBS; 10 vasculotide)

IP Immunization
(50ugOVA/1mg Alum)

PBS or Vasculotide injection every 48h
Aerosolization 3 times/ week 62 days (10 PBS; 10 vasculotide)

IP Immunization
(50ugOVA/1mg Alum)

PBS or Vasculotide injection every 48h
Aerosolization 3 times/ week

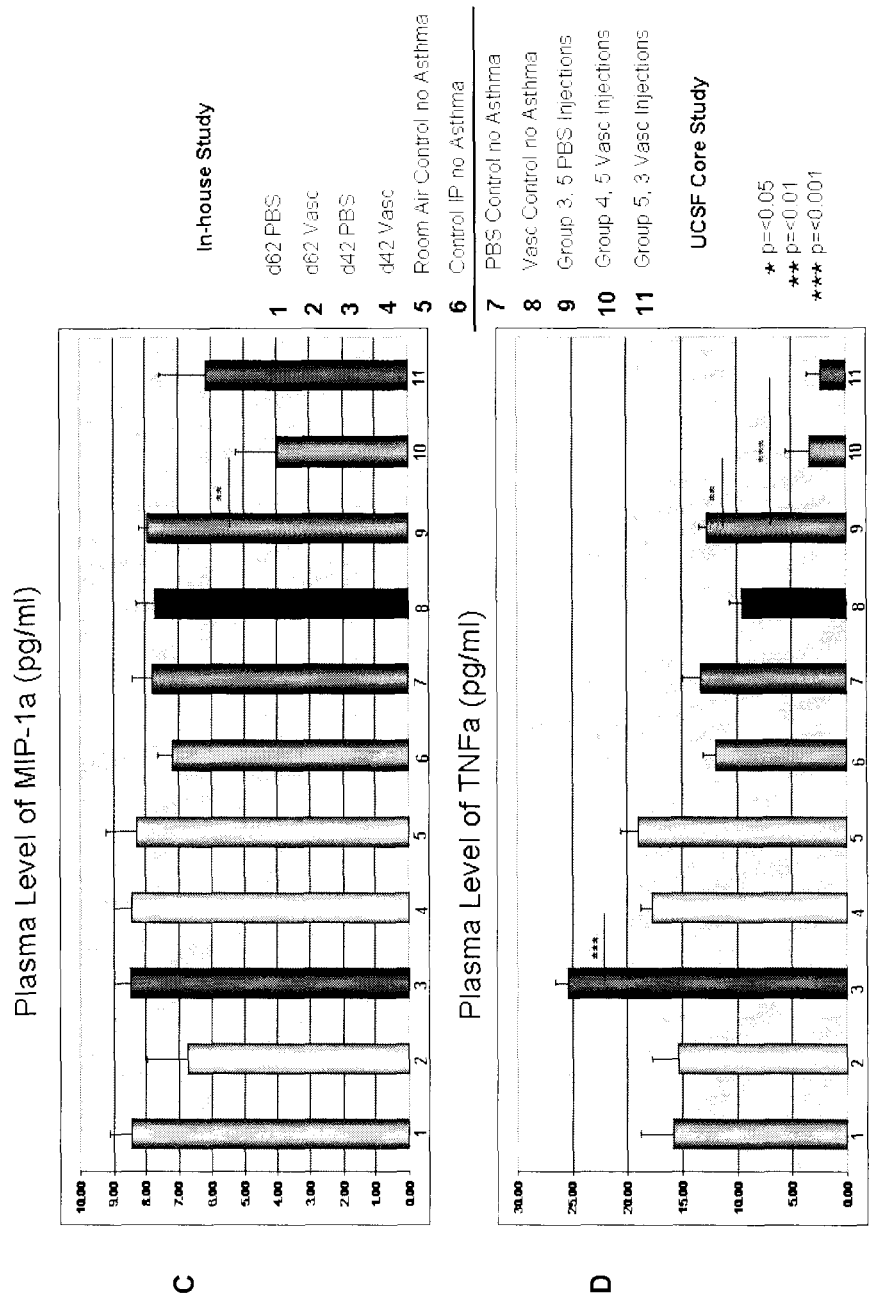

METHODS AND USES OF TIE2 BINDING AND/OR ACTIVATING AGENTS

CROSS REFERENCE TO RELATED APPLICATIONS

This is a national phase entry of PCT/CA2011/000473 filed Apr. 28, 2011 (which designates the U.S.) which claims priority from U.S. Provisional Patent Application No. 61/328,932 filed Apr. 28, 2010, all of which is incorporated by reference herein in their entirety.

INCORPORATION OF SEQUENCE LISTING

A computer readable form of the Sequence Listing "20925-P36806US01_SequenceListing.txt" (2,406 bytes), submitted via EFS-WEB and created on Jan. 10, 2013, is herein incorporated by reference.

FIELD OF THE DISCLOSURE

The disclosure relates to methods and uses of Tie2 binding and/or activating agents. In particular, the disclosure relates to methods and uses for inhibiting the expansion of granulocyte colony forming unit (CFU-G), for reducing eosinophils and basophils and for treating allergic diseases.

BACKGROUND OF THE DISCLOSURE

Angiopoietins (Ang) 1-4 have all been shown to bind to and activate Tie2 receptor tyrosine kinase activity to differing extents. All the Angs are characterized structurally by an N-terminal super clustering domain (SCD) followed by a coiled-coil domain (CCD) and a C-terminal fibrinogen-like domain (FLD) (Ward and Dumont 2002; Tsigkos et al. 2003). Functional studies have highlighted a role for the SCD and CCD's in forming high order homotypic multimers of Ang (Procopio et al. 1999). The specific nature of these multimers is variable and is unique to each Ang family member. Binding specificity of the Angs for the Tie2 receptor has been ascribed to the FLD (Tisgkos et al. 2003; Procopio et al. 1999). Taken together, it is the unique structural attributes of each Ang family member that promotes binding and differential clustering of Tie2. The pleiotropic physiological effects of Angs 1-4 are thought to at least in part be mediated by appropriate and specific clustering of the receptor. For instance mice engineered to overexpress the CCD of Ang 1, capable of multimerizing with endogenous Ang1 produced in the same cell, caused improper patterning of the coronary vessels (Ward et al. 2004). Furthermore, chimeric forms of Ang 1 engineered to contain the C-terminal FLD and one of several different CCD's differed in their ability to activate the Tie2 receptor (Cho et al. 2004a; Cho et al. 2004b).

Based on this information, the present inventors previously designed a peptide mimetic, called Vasculotide, that binds to Tie2 and when configured as a tetramer results in the clustering of the receptor and its activation.

Activating Tie2 through the tetramerization of high affinity Tie2 binding peptides using the biotin/avidin model (Van Slyke et al. 2009) has established the use of the peptide as an agonist to the Tie2 receptor to promote angiogenesis for applications in diabetic wound healing and other cardiovascular indications.

Patients with allergic diseases respond to an allergen with a systemic response that initiates the production of specific inflammatory cells, eosinophils and basophils and their progenitors, from the bone marrow (Denburg and Keith 2008; Hogan et al. 2008; Rothenberg and Hogan 2006). Upon release of these cells from the bone marrow they usually target the respiratory mucosa and other tissues and once activated eosinophils and basophils are one of the key immunomodulatory cells that sustain the allergic response (Rothenberg and Hogan 2006; Barrett and Austen 2009; Gauvreau et al. 2009; Schroeder 2009). These cells are known to secrete TGF-$\beta$, which is known to be an extremely potent pro-fibrogenic factor (Jacobsen et al. 2007; Hogan 2007; Raap and Wardlaw 2008).

SUMMARY OF THE DISCLOSURE

The present inventors have shown that administration of a multimeric form of a Tie2 binding peptide called "Vasculotide" is able to inhibit the expansion of CFU-G cells, resulting in a reduction in eosinophils and basophils, without a more general immunosuppression. The present inventors have also shown that in a transgenic mouse model of atopic dermatitis, triple transgenic mice which express Ang-1 showed amelioration of disease whereas triple transgenic mice, which express Ang-2, showed deterioration of disease.

Accordingly, the present disclosure provides a method of inhibiting the expansion of CFU-G cells in an animal or cell in need thereof comprising administering a Tie2 binding and/or activating agent. The disclosure also provides use of a Tie2 binding and/or activating agent for inhibiting the expansion of CFU-G cells in an animal or cell in need thereof. Also provided is use of a Tie2 binding and/or activating agent in the preparation of a medicament for inhibiting the expansion of CFU-G cells in an animal or cell in need thereof. Further provided is a Tie2 binding and/or activating agent for use in inhibiting the expansion of CFU-G cells in an animal or cell in need thereof.

The present disclosure also provides a method of reducing eosinophils and/or basophils in an animal or cell in need thereof comprising administering a Tie2 binding and/or activating agent. The disclosure also provides use of a Tie2 binding and/or activating agent for reducing eosinophils and/or basophils in an animal or cell in need thereof. Also provided is use of a Tie2 binding and/or activating agent in the preparation of a medicament for reducing eosinophils and/or basophils in an animal or cell in need thereof. Further provided is a Tie2 binding and/or activating agent for use in reducing eosinophils and/or basophils in an animal or cell in need thereof.

The present disclosure further provides a method of treating allergic disease or response in an animal or cell in need thereof comprising administering a Tie2 binding and/or activating agent. The disclosure also provides use of a Tie2 binding and/or activating agent for treating allergic disease or response in an animal or cell in need thereof. Also provided is use of a Tie2 binding and/or activating agent in the preparation of a medicament for treating allergic disease or response in an animal or cell in need thereof. Further provided is a Tie2 binding and/or activating agent for use in treating allergic disease or response in an animal or cell in need thereof. In one embodiment, the allergic disease is an atopic allergic disease, such as atopic dermatitis, asthma or allergic rhinitis.

The present disclosure also provides a method of treating a condition associated with eosinophils and/or basophils in an animal or cell in need thereof comprising administering a Tie2 binding and/or activating agent. The disclosure also provides use of a Tie2 binding and/or activating agent for treating a condition associated with eosinophils and/or basophils in an animal or cell in need thereof. Also provided is use of a Tie2 binding and/or activating agent in the preparation of a medicament for treating a condition associated with eosinophils and/or basophils in an animal or cell in need thereof. Further provided is a Tie2 binding and/or activating agent for use in treating a condition associated with eosinophils and/or basophils in an animal or cell in need thereof. In one embodiment, the condition associated with eosinophils and/or basophils is a myelodysplastic syndrome. In one embodiment, the condition associated with eosinophils and/or basophils is a leukemia of eosinophil and/or basophil origin, such as chronic myeloid leukemia, acute myeloid leukemia, chronic eosinophilc leukemia, acute eosinophilic leukemia, chronic myelomonocytic leukemia with eosinophilia, and acute basophilic leukemia. In another embodiment, the condition associated with eosinophils and/or basophils is inflammatory bowel disease. In yet another embodiment, the condition associated with eosinophils and/or basophils is a parasitic infection. In yet another embodiment, the condition associated with eosinophils and/or basophils is idiopathic hypereosinophilic syndrome (HES).

The present disclosure also provides a method of reducing inflammatory cytokine and/or chemokine levels in an animal or cell in need thereof comprising administering a Tie2 binding and/or activating agent. The disclosure also provides use of a Tie2 binding and/or activating agent for reducing inflammatory cytokine and/or chemokine levels in an animal or cell in need thereof. Also provided is use of a Tie2 binding and/or activating agent in the preparation of a medicament for reducing inflammatory cytokine and/or chemokine levels in an animal or cell in need thereof. Further provided is a Tie2 binding and/or activating agent for use in reducing inflammatory cytokine and/or chemokine levels in an animal or cell in need thereof. In one embodiment, the inflammatory cytokine and/or chemokine levels are serum inflammatory cytokine and/or chemokine levels. In one embodiment, the inflammatory cytokines and/or chemokines comprise at least one of eotaxin, IL-17, MIG, IL12/IL23 (p40), IL-9, MIP-1a, MIP-1b, RANTES, TNF-α, IL-1β, IL-5, IL-13, and MCP-1. In another embodiment, the inflammatory cytokines and chemokines comprise IL-17, MIG, IL12/IL23 (p40), IL-9, MIP-1a, MIP-1b, RANTES, TNF-α, IL-1β, IL-5, IL-13, and MCP-1. In yet another embodiment, the inflammatory cytokines and/or chemokines comprise eotaxin.

The agent may be administered in any suitable manner, including without limitation, topically, systemically, orally, intranasally or by inhalation.

In one embodiment, the agent is an angiopoietin-1 or a nucleic acid encoding angiopoietin-1. In another embodiment, the agent is an inhibitor of angiopoietin-2, such as a blocking antibody against angiopoietin-2 or an antisense nucleic acid against angiopoietin-2.

In another embodiment, the agent comprises a Tie2 binding peptide monomer or a multimeric form of a Tie2 binding peptide monomer.

The multimeric form can be, for example, a dimer, tetramer, or a multimeric form that comprises six, eight, ten or twelve units of the monomer. In another embodiment, the multimeric form comprises an odd number of units, such as three, five, seven, nine or eleven units.

In yet another embodiment, the Tie2 binding peptide monomer comprises a structure: A-B-C, wherein A comprises a Tie2 binding peptide, B comprises a spacer and C comprises a multimerizing group, wherein C has affinity for D, a multimer agent comprising multiple binding sites for C. For example, the multimer agent D can have four binding sites for the multimerizing group C such that a tetramer is formed when four Tie2 binding peptide monomers, A-B-C, interact with the multimer agent D. In an embodiment, C comprises a biotin group and D comprises an agent selected from the group consisting of avidin, streptavidin and neutravidin. In yet another embodiment, B comprises polyethylene glycol (PEG).

In a further embodiment, the Tie2 binding peptide monomer comprises a structure: A-B, wherein A comprises a Tie2 binding peptide and B comprises a spacer, wherein the multimeric form is created by covalent linkage of multiple Tie2 binding peptide monomers via the spacer B. In an embodiment, B comprises polyethylene glycol (PEG).

Tie2 binding peptides for use in the monomers include, but are not limited to, a T7 peptide as shown in SEQ ID NOs: 1 or 2, a GA3 peptide as shown in SEQ ID NOs: 3 or 4, a T6 peptide as shown in SEQ ID NOs: 7 or 8 or a T8 peptide as shown in SEQ ID NOs: 5 or 6. In an alternative embodiment, the Tie2 binding peptide is a T4 peptide as shown in SEQ ID NOs: 9 or 10.

In another embodiment, the multimeric form is a dimer, comprising: (a) a first peptide chain; (b) a second peptide chain; and (c) a linking moiety connecting said first and second peptide chains, wherein said peptide dimer binds to and activates the Tie2 receptor. In one embodiment, the first peptide chain is a T7 peptide (SEQ ID NOs: 1 or 2) and/or the second peptide chain is a T7 peptide (SEQ ID NOs: 1 or 2). Optionally, the linking moiety comprises one or more water soluble polymers covalently bound to the first peptide chain and the second peptide chain. The one or more water soluble polymers may be linear polymers. In one embodiment, the water soluble polymer is a polyethylene glycol (PEG), optionally having a molecular weight in the range of about 3,000 Daltons to 50,000 Daltons. In various embodiments, the PEG has a molecular weight of about 3,000, about 3,400, about 5,000, about 10,000, about 15,000, about 20,000, about 25,000, about 30,000 or about 40,000 Daltons.

In yet another embodiment, the multimeric form comprises a peptide tetramer, comprising: (a) a first peptide chain; (b) a second peptide chain; (c) a third peptide chain; (d) a fourth peptide chain; and (e) a linking moiety connecting said first, second, third and fourth peptide chains, wherein said peptide tetramer binds to and activates the Tie2 receptor. Optionally, the first, second, third and fourth peptide chains are T7 peptides (SEQ ID NOs: 1 or 2). The linking moiety may comprise one or more water soluble polymers covalently bound to the first, second, third and fourth peptide chains. In one embodiment, the water soluble polymer is a branched chain water soluble polymer, such as PEG. The branched PEG may have a molecular weight in a range of about 3,000 Daltons to about 50,000 Daltons. In various embodiments, the PEG has a molecular weight of about 3,000, about 3,400, about 5,000, about 10,000, about 15,000, about 20,000, about 25,000, about 30,000 or about 40,000 Daltons.

The multimeric forms described herein exhibit Tie2 agonist activity. For example, the multimeric form stimulates Tie2 phosphorylation or stimulates phosphorylation of MAPK, AKT and eNOS.

In a particular embodiment, the multimeric form is a tetramer and the Tie2 binding peptide monomer comprises a structure: A-B-C, wherein:
  A comprises a Tie2 binding peptide selected from a T7 peptide (SEQ ID NOs: 1 or 2) and a GA3 peptide (SEQ ID NOs: 3 or 4);
  B comprises a polyethylene glycol spacer; and
  C comprises a biotin group,
wherein four copies of A-B-C are associated with a tetramer agent, D, to create the tetramer form, the tetramer agent, D, being selected from the group consisting of avidin, streptavidin and neutravidin.

Other features and advantages of the present disclosure will become apparent from the following detailed description. It should be understood, however, that the detailed description and the specific examples while indicating embodiments of the disclosure are given by way of illustration only, since various changes and modifications within the spirit and scope of the disclosure will become apparent to those skilled in the art from this detailed description.

BRIEF DESCRIPTION OF THE DRAWINGS

The disclosure will now be described in relation to the drawings in which:

FIG. 3C shows the effect of Angiopoietin 1 (Ang1) in a mouse model of atopic dermatitis. Ang1 expression ameliorates the experimental atopic dermatitis phenotype. Gross phenotypic improvement is noted when experimental atopic dermatitis (pTek-tTA:pTetOS-Tek) mice (DT(Tie-2)) are crossed to Ang1 mice, triple transgenic (TT)(pTek-tTA:pTetOS-Tek:pTetOS-Ang1) (TT (Tie2+Ang-1)). The effects are evidenced by a decrease in erythema around the nose and eyes. Also noted is a reduction in ear microhaemorrhages (left images) and tail scaly plaque formation.

FIG. 3D shows the effect of Angiopoietin 2 (Ang2) in a mouse model of atopic dermatitis. Ang2 expression exacerbates all aspects of the experimental atopic dermatitis phenotype. Ang2 triple transgenic (TT) mice (TT) Tie-2+Ang-2 present with increased erythema and tail plaque compared to experimental atopic dermatitis animals (DT (Tie-2)).

FIG. 3E shows Angiopoietin 1 ameliorates experimental atopic dermatitis while Angiopoietin 2 exacerbates all aspects of the phenotype. Enforced expression of Ang2 by the minimal Tie2 promoter (DT (Ang-2)) does not induce atopic dermatitis or erythema compared to wild-type (WT) animals. Only in triple transgenics (pTek-tTA:pTetOS-Tek:pTetOS-Ang2) is it observed that Ang2 exacerbates the AT derm phenotype. These effects are evidenced by an increase in erythema around the nose and eyes. Also noted is an increase in ear microhaemorrhages and tail scaly plaque formation in the triple transgenic (pTek-tTA:pTetOS-Tek:pTetOS-Ang2).

FIG. 5 shows the effects of Vasculotide treatment on a mouse model of atopic dermatitis. Vasculotide treatment (D and F) was shown to ameliorate the superficial features of the atopic dermatitis phenotype. Gross phenotypic improvement was noted when experimental atopic dermatitis mice (pTek-tTA:pTetOS-Tek) (AT-Derm) were treated with Vasculotide (40 μg/kg every 3 days for 30 days) regardless of the initial severity of the phenotype (Moderate (C, D) or Severe (E, F)). Wild-type mice (Control) treated with Vasculotide (B) were indistinguishable from PBS-treated (A) littermates. Decreased erythema around the eyes and snout was observed in Vasculotide-treated moderate (D) and severe (F) mice with an overall reduction in ear microhaemorrhages compared to corresponding PBS-treated animals (C and E respectively).

DETAILED DESCRIPTION OF THE DISCLOSURE

Figure 1A:
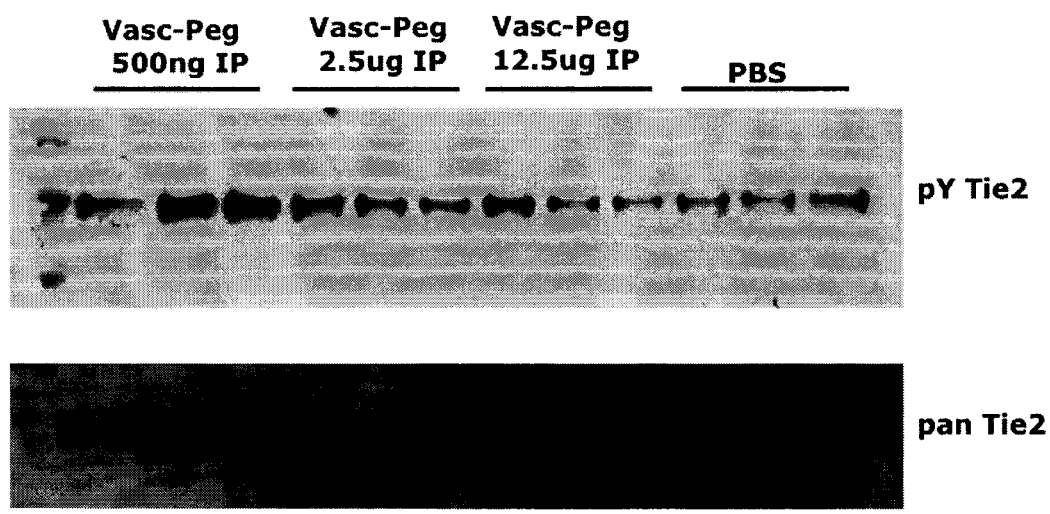
FIG. 1A shows Vasculotide-dependent activation of the Tie2 receptor in vivo. CD1 mice were injected intraperitoneally (I.P.) with indicated doses of Vasc-PEG. PBS was used as a control. The compound was allowed to circulate for 1 hour prior to sacrificing. Immunoprecipitation (IP) of Tie2 from lung lysates and western blot analysis of Tie2 activation were performed (indicated by phosphotyrosine (pY) Tie2). Total levels of Tie2 are indicated in the lower panel (pan Tie2).

The present inventors have shown that Vasculotide, a Tie2 binding peptide agent, inhibits the expansion of granulocyte colony forming units, resulting in reduced numbers of basophils and eosinophils, both of which are involved in allergic disease and response. Further, the inventors have shown that expression of Angiopoietin-1 (Ang1) improves the phenotype of mice with atopic dermatitis while expression of Angiopoietin-2 (Ang2) exacerbates the condition.

DEFINITIONS

As used herein, the term "Tie2" refers to a receptor protein tyrosine kinase that is expressed almost exclusively on endothelial and progenitor cells and that is also known in the art as TEK, p140 TEK, CD202B and VMCM. The term "Tie2" is intended to encompass the receptor from any species that expresses this receptor. In one embodiment, Tie2 is a human Tie2. The mRNA and protein sequences of human Tie2 are set forth at GenBank Accession Nos. NM_000459 and NP_000450, respectively.

As used herein, the term "angiopoietin" is intended to refer to any one of a family of protein growth factors known to be ligands for Tie2, including angiopoietin 1 (or Ang 1), angiopoietin 2 (or Ang 2), angiopoietin 3 (or Ang 3) and angiopoietin 4 (or Ang 4). The term "angiopoietin" is intended to encompass the growth factor from any species that expresses the growth factor, optionally human angiopoietin family members. The mRNA and protein sequences of human Ang 1 are set forth at GenBank Accession Nos. NM_001146 and NP_001137, respectively. The mRNA and protein sequences of human Ang 2 are set forth at GenBank Accession Nos. NM_001147 and NP_001138, respectively. The mRNA and protein sequences of human Ang 4 are set forth at GenBank Accession Nos. NM_015985 and NP_057069, respectively.

As used herein, the term "MAPK" is intended to refer to mitogen activated protein kinase, also known as ERK or extracellular signal-regulated kinase, an intracellular kinase that is phosphorylated upon activation of Tie2. The term "MAPK" is intended to encompass the kinase from any species that expresses the kinase, optionally human MAPK. The mRNA and protein sequences of human MAPK are set forth at GenBank Accession Nos. NM_002736 and NP_002745, respectively.

As used herein, the term "AKT" is intended to refer to a protein kinase also known as v-akt murine thymoma viral oncogene homolog, an intracellular kinase that is phosphorylated upon activation of Tie2. The term "AKT" is intended to encompass the kinase from any species that expresses the kinase, optionally human AKT. The mRNA and protein sequences of human AKT are set forth at GenBank Accession Nos. NM_001014431 and NP_001014431, respectively.

As used herein, the term "eNOS" is intended to refer to endothelial cell nitric oxide synthetase, also known as NOS 3, NOS III or ECNOS, an intracellular enzyme that is phosphorylated upon activation of Tie2. The term "eNOS" is intended to encompass the enzyme from any species that expresses the enzyme, optionally human eNOS. The mRNA and protein sequences of human eNOS are set forth at GenBank Accession Nos. NM_000603 and NP_000594, respectively.

As used herein, the term "Tie2 binding peptide" is intended to encompass peptides at least two amino acids in length and optionally no more than 100 amino acids in length that have binding affinity for Tie2. The term "Tie2 binding peptide" is not intended to encompass naturally occurring ligands for Tie2, such as native, full-length angiopoietin proteins. Furthermore, the term "Tie2 binding peptide" is intended to encompass peptides comprised in whole or in part of L-amino acids, peptides comprised in whole or in part of D-amino acids and peptides comprised of both L- and D-amino acids. Still further, the term "Tie2 binding peptide" is intended to encompass peptides comprised in whole or in part of the 20 naturally-occurring amino acid residues, peptides comprised in whole or in part of non-naturally-occurring amino acid residues and peptide comprised of both naturally-occurring and non-naturally-occurring amino acid residues.

As used herein, the term "Tie2 binding peptide monomer" is intended to refer to a single unit of a Tie2 binding peptide compound. The Tie2 binding peptide compound, or monomer, comprises the Tie2 binding peptide, and may comprise other chemical moieties (e.g., spacers, multimerizing groups and the like), but the Tie2 binding peptide monomer comprises only one copy (or unit) of the Tie2 binding peptide and thus has a single valency for the Tie2 receptor.

As used herein, the term "multimeric form" of a Tie2 binding peptide monomer is intended to refer to forms that contain more than one unit of the Tie2 binding peptide monomer such that the multimeric form (e.g., dimer, tetramer and the like) comprises more than one copy (or unit) of the Tie2 binding peptide and thus has multivalency for the Tie2 receptor. In a particular embodiment, the multimeric form is a tetramer. Multimeric forms of Tie2 binding peptides have been previously described in PCT/CA2007/001903, incorporated herein by reference in its entirety.

As used herein, the term "high affinity", as used with respect to binding of a Tie2 binding peptide to the Tie2 receptor, is intended to mean binding of the peptide to the receptor with $K_d$ of about $10^{-3}$ M or less, $10^{-4}$ M or less, or $10^{-5}$ M or less.

As used herein, the term "Tie2 agonist activity" is intended to refer to stimulating, enhancing, increasing or upregulating Tie2 receptor activity, as measured by any method, technique, signal, detector or indicator that is known in the art to be indicative of Tie2 receptor activity. Non-limiting examples of such indicators of Tie2 activity include phosphorylation of human Tie2 at amino acid residue Y897, Y992, Y1048, Y1102, Y1108 or Y1113, or at amino acid Y1100, Y1106, or Y1106, 1111 of mouse Tie2, or phosphorylation of one or more of MAPK, AKT and eNOS. Also included as indicators are the ability to reduce the expansion of CFU-G cells in vitro and to reduce circulating basophils and/or eosinophils.

Methods and Uses

The present inventors have shown that administration of a multimeric form of a Tie2 binding peptide, called Vasculotide, is able to inhibit the expansion of CFU-G cells.

Accordingly, the present disclosure provides a method of inhibiting the expansion of CFU-G cells comprising administering a Tie2 binding and/or activating agent. The disclosure also provides use of a Tie2 binding and/or activating agent for inhibiting the expansion of CFU-G cells in an animal or cell in need thereof. Also provided is use of a Tie2 binding and/or activating agent in the preparation of a medicament for inhibiting the expansion of CFU-G cells in an animal or cell in need thereof. Further provided is a Tie2 binding and/or activating agent for use in inhibiting the expansion of CFU-G cells in an animal or cell in need thereof.

The term "CFU-G" as used herein refers to colony-forming unit-granulocyte cells, which is a type of blood-forming cell that produces granulocytes, such as eosinophils, basophils and neutrophils. "Inhibition of expansion" as used herein refers to a decrease of at least 5%, 10%, 20%, 30%, 40%, 50%, 60%, 70%, 80% or more in the number of granulocyte colony-forming cells as compared to an untreated control.

The present inventors have shown that the administration of Vasculotide results in a reduction in circulating eosinophils and basophils, without a more general immunosuppression of T cells, B cells, monocytes or neutrophils. Accordingly, the present disclosure also provides a method of reducing eosinophils and/or basophils in an animal or cell in need thereof comprising administering a Tie2 binding and/or activating agent. The disclosure also provides use of a Tie2 binding and/or activating agent for reducing eosinophils and/or basophils in an animal or cell in need thereof. Also provided is use of a Tie2 binding and/or activating agent in the preparation of a medicament for reducing eosinophils and/or basophils in an animal or cell in need thereof. Further provided is a Tie2 binding and/or activating agent for use in reducing eosinophils and/or basophils in an animal or cell in need thereof.

The phrase "reducing eosinophils and/or basophils" as used herein refers to a reduction in the number of circulating eosinophils and/or basophils wherein at least 5%, 10%, 20%, 30%, 40%, 50%, 60%, 70%, or 80% less eosinophils and/or basophils are circulating compared to control. Further, reduction of basophils leads to reduction of mast cells, thus reduction of basophils, includes reduction of mast cells.

Eosinophils and basophils are implicated in the allergic response. Accordingly, the present disclosure also provides a method of treating an allergic disease or response in an animal or cell in need thereof comprising administering a Tie2 binding and/or activating agent. The disclosure also provides use of a Tie2 binding and/or activating agent for treating an allergic disease or response in an animal or cell in need thereof. Also provided is use of a Tie2 binding and/or activating agent in the preparation of a medicament for treating an allergic disease or response in an animal or cell in need thereof. Further provided is a Tie2 binding and/or activating agent for use in treating an allergic disease or response in an animal or cell in need thereof.

The term "treatment or treating" as used herein means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable.

In an embodiment, the allergic disease or response is atopic disease. The term "atopic disease" as used herein refers to an allergic sensitivity affecting parts of the body not in direct contact with an allergen and is defined by an increase in levels of IgE in the serum of the animal. In one embodiment, the atopic disease is atopic dermatitis/eczema, asthma, conjunctivitis, chronic sinusitis, eosinophil esophagitis, food allergies or allergic rhinitis/hay fever. Asthma, allergic rhinitis and atopic dermatitis are commonly referred to as the atopic triad wherein in many cases atopic dermatitis is the first to manifest itself (Eichenfield et al. 2003) and is commonly followed by either the development of asthma and/or allergic rhinitis. Accordingly, in one embodiment, the atopic disease is atopic dermatitis. In another embodiment, the atopic disease is asthma.

In another embodiment, the present disclosure also provides a method of treating a condition associated with eosinophils and/or basophils in an animal or cell in need thereof comprising administering a Tie2 binding and/or activating agent. The disclosure also provides use of a Tie2 binding and/or activating agent for treating a condition associated with eosinophils and/or basophils in an animal or cell in need thereof. Also provided is use of a Tie2 binding and/or activating agent in the preparation of a medicament for treating a condition associated with eosinophils and/or basophils in an animal or cell in need thereof. Further provided is a Tie2 binding and/or activating agent for use in treating a condition associated with eosinophils and/or basophils in an animal or cell in need thereof. In one embodiment, the condition associated with eosinophils and/or basophils is a myelodysplastic syndrome. In another embodiment, the condition associated with eosinophils and/or basophils is a leukemia of eosinophil and/or basophil origin such as chronic myeloid leukemia, acute myeloid leukemia, chronic eosinophilc leukemia, acute eosinophilic leukemia, chronic myelomonocytic leukemia with eosinophilia, and acute basophilic leukemia. In another embodiment, the condition associated with eosinophils and/or basophils is inflammatory bowel disease. In yet another embodiment, the condition associated with eosinophils and/or basophils is a parasitic infection. In yet another embodiment, the condition associated with eosinophils and/or basophils is idiopathic hypereosinophilic syndrome (HES).

The present disclosure also provides a method of reducing inflammatory cytokine and/or chemokine levels in an animal or cell in need thereof comprising administering a Tie2 binding and/or activating agent. The disclosure also provides use of a Tie2 binding and/or activating agent for reducing inflammatory cytokine and/or chemokine levels in an animal or cell in need thereof. Also provided is use of a Tie2 binding and/or activating agent in the preparation of a medicament for reducing inflammatory cytokine and/or chemokine levels in an animal or cell in need thereof. Further provided is a Tie2 binding and/or activating agent for use in reducing inflammatory cytokine and/or chemokine levels in an animal or cell in need thereof. In one embodiment, the inflammatory cytokine and/or chemokine levels are serum inflammatory cytokine and/or chemokine levels. In one embodiment, the inflammatory cytokines and/or chemokines comprise at least one of eotaxin, IL-17, MIG, IL12/IL23 (p40), IL-9, MIP-1a, MIP-1b, RANTES, TNF-α, IL-1β, IL-5, IL-13, and MCP-1. In another embodiment, the inflammatory cytokines and chemokines comprise IL-17, MIG, IL12/IL23 (p40), IL-9, MIP-1a, MIP-1b, RANTES, TNF-α, IL-1β, IL-5, IL-13, and MCP-1. In yet another embodiment, the inflammatory cytokines and/or chemokines comprise eotaxin. Such methods and uses have therapeutic applications in treating diseases and conditions associated with increased inflammatory cytokines and/or chemokines.

In an embodiment, the methods and uses further comprise administration or use of an immunomodulator or corticosteroid in combination with the Tie2 binding and/or activating agent.

The Tie2 binding and/or activating agent may be administered by any suitable method, including topically, systemically, orally, intranasally or by inhalation.

The term "administering" includes the administration of the multimeric form to an animal or to a cell in vitro or in vivo.

The term "a cell" includes a single cell as well as a plurality or population of cells. Administering to a cell includes administering in vitro (or ex vivo) as well as in vivo.

Administration of an "effective amount" of the agents described herein is defined as an amount effective, at dosages and for periods of time necessary to achieve the desired result. The effective amount of the Tie2 binding and/or activating agent may vary according to factors such as the disease state, age, sex, and weight of the animal. Dosage regimens may be adjusted to provide the optimum therapeutic response. For example, several divided doses may be administered daily or the dose may be proportionally reduced as indicated by the exigencies of the therapeutic situation. The mode of administration (e.g. in vivo by injection or topical application or ex vivo in culture) will also impact the dosage regime.

The term "animal" as used herein includes all members of the animal kingdom including humans.

The methods and uses described herein include administration or use of the Tie2 binding and/or activating agent alone or as part of a pharmaceutical composition comprising the Tie2 binding and/or activating agent. Such pharmaceutical compositions can be for intralesional, intravenous, topical, rectal, parenteral, local, inhalant, intranasal or subcutaneous, intradermal, intramuscular, intrathecal, transperitoneal, oral, and intracerebral use. The composition can be in liquid, solid or semisolid form, for example pills, tablets, creams, gelatin capsules, capsules, suppositories, soft gelatin capsules, gels, membranes, tubelets, solutions or suspensions.

The pharmaceutical compositions can be prepared by per se known methods for the preparation of pharmaceutically acceptable compositions which can be administered to patients, and such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 2003—20$^{th}$ Edition) and in The United States Pharmacopeia: The National Formulary (USP 24 NF19) published in 1999).

On this basis, the pharmaceutical compositions for use in the methods and/or uses described herein include, albeit not exclusively, the active compound or substance in association with one or more pharmaceutically acceptable vehicles or diluents, and contained in buffered solutions with a suitable pH and iso-osmotic with the physiological fluids. The pharmaceutical compositions may additionally contain other agents such as corticosteroids and immune modulators.

Tie2 Binding and/or Activating Agents for Use in the Methods and Uses Described Herein Angiopoietin-1

In one embodiment, the Tie2 binding and/or activating agent comprises an angiopoietin-1 protein or a variant thereof. In one embodiment, the angiopoietin-1 protein comprises the amino acid sequence as shown in NP__00137 or a variant thereof.

In another embodiment, the Tie2 binding and/or activating agent comprises a nucleic acid encoding an angiopoietin-1 protein or variant thereof. In one embodiment, the angiopoietin-1 nucleic acid molecule comprises the amino acid sequence as shown in NM__00146 or a variant thereof.

The term "nucleic acid" as used herein refers to a sequence of nucleotide or nucleoside monomers consisting of naturally occurring bases, sugars and intersugar (backbone) linkages. The nucleic acid sequences may be ribonucleic (RNA) or deoxyribonucleic acids (DNA).

The term "variant" as used herein includes modifications, substitutions, additions, derivatives, analogs, fragments or chemical equivalents of the angiopoietin amino acid sequences that perform substantially the same function as the angiopoietin peptides disclosed herein in substantially the same way. For instance, the variants of the angiopoietin peptides would have the same function of being able to bind to and/or activate Tie2.

Variants also include peptides with amino acid sequences that are substantially or essentially identical to the angiopoietin sequences.

The term "substantially identical" or "essentially identical" as used herein means an amino acid sequence that, when optimally aligned, for example using the methods described herein, share at least 75%, 80%, 85%, 90%, 95%, 96%, 97%, 98%, 99%, or 100% sequence identity with a second amino acid sequence.

The term "angiopoietin-1 fragment" as used herein means a portion of the angiopoietin-1 peptide that contains at least 10%, 20%, 30%, 40%, 50%, 60%, 70%, 80%, 90%, 95%, or more of the entire length of the angiopoietin-1 polypeptide that is able to bind and/or activate Tie2.

The term "homolog" means those amino acid or nucleic acid sequences which have slight or inconsequential sequence variations from angiopoietin-1, i.e., the sequences function in substantially the same manner. The variations may be attributable to local mutations or structural modifications. Sequences having substantial homology include nucleic acid sequences having at least 65%, at least 85%, or 90-95% identity with angiopoietin-1 sequences. Sequence identity can be calculated according to methods known in the art. Nucleic acid sequence identity can be assessed by the algorithm of BLAST version 2.1 advanced search. BLAST is a series of programs that are available online at .ncbi.nlm.nih.gov/BLAST. The advanced blast search (ncbi.nlm.nih.gov/blast/blast.cgi?Jform=1) is set to default parameters. (ie Matrix BLOSUM62; Gap existence cost 11; Per residue gap cost 1; Lambda ratio 0.85 default). References to BLAST searches are: Altschul, S. F., Gish, W., Miller, W., Myers, E. W. & Lipman, D. J. (1990) "Basic local alignment search tool." J. Mol. Biol, 215:403410; Gish, W. & States, D. J. (1993) "Identification of protein coding regions by database similarity search." Nature Genet. 3:266272; Madden, T. L., Tatusov, R. L. & Zhang, J. (1996) "Applications of network BLAST server" Meth. Enzymol. 266:131__141; Altschul, S. F., Madden, T. L., Schaffer, A. A., Zhang, J., Zhang, Z., Miller, W. & Lipman, D. J. (1997) "Gapped BLAST and PSI_BLAST: a new generation of protein database search programs." Nucleic Acids Res. 25:33893402; Zhang, J. & Madden, T. L. (1997) "PowerBLAST: A new network BLAST application for interactive or automated sequence analysis and annotation." Genome Res. 7:649656.

The term "analog" means an amino acid or nucleic acid sequence which has been modified as compared to the angiopoietin-1 sequences wherein the modification does not alter the utility of the sequence (e.g. as a Tie2 binding and/or activating agent) as described herein. The modified sequence or analog may have improved properties over the angiopoietin-1 sequences. One example of a nucleic acid modification to prepare an analog is to replace one of the naturally occurring bases (i.e. adenine, guanine, cytosine or thymidine) of the sequence with a modified base such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8 amino guanine, 8-thiol guanine, 8-thiolalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

Another example of a modification is to include modified phosphorous or oxygen heteroatoms in the phosphate backbone, short chain alkyl or cycloalkyl intersugar linkages or short chain heteroatomic or heterocyclic intersugar linkages in the nucleic acid molecules. For example, the nucleic acid sequences may contain phosphorothioates, phosphotriesters, methyl phosphonates, and phosphorodithioates.

A further example of an analog of a nucleic acid molecule of the disclosure is a peptide nucleic acid (PNA) wherein the deoxyribose (or ribose) phosphate backbone in the DNA (or RNA), is replaced with a polyamide backbone which is similar to that found in peptides (P. E. Nielsen, et al Science 1991, 254, 1497). PNA analogs have been shown to be resistant to degradation by enzymes and to have extended lives in vivo and in vitro. PNAs also bind stronger to a complementary DNA sequence due to the lack of charge repulsion between the PNA strand and the DNA strand. Other nucleic acid analogs may contain nucleotides containing polymer backbones, cyclic backbones, or acyclic backbones. For example, the nucleotides may have morpholino backbone structures (U.S. Pat. No. 5,034,506). The analogs may also contain groups such as reporter groups, a group for improving the pharmacokinetic or pharmacodynamic properties of nucleic acid sequence.

The disclosure also includes sequences that hybridize to the angiopoietin-1 sequences or a fragment thereof and maintain the property of binding and/or activating Tie2. The term "sequence that hybridizes" means a nucleic acid sequence that can hybridize to a sequence under stringent hybridization conditions. Appropriate "stringent hybridization conditions" which promote DNA hybridization are known to those skilled in the art, or may be found in Current Protocols in Molecular Biology, John Wiley & Sons, N.Y. (1989), 6.3.1-6.3.6. The term "stringent hybridization conditions" as used herein means that conditions are selected which promote selective hybridization between two complementary nucleic acid molecules in solution. Hybridization may occur to all or a portion of a nucleic acid sequence molecule. The hybridizing portion is at least 50% the length with respect to one of the polynucleotide sequences encoding a polypeptide. In this regard, the stability of a nucleic acid duplex, or hybrids, is determined by the Tm, which in sodium containing buffers is a function of the sodium ion concentration, G/C content of labeled nucleic acid, length of nucleic acid probe (I), and temperature (Tm=81.5° C.−16.6 (Log 10 [Na+])+0.41(% (G+C)−600/I). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a greater than 95% identity, the final wash will be reduced by 5° C. Based on these considerations stringent hybridization conditions shall be defined as: hybridization at 5× sodium chloride/sodium citrate (SSC)/5×Denhardt's solution/1.0% SDS at Tm (based on the above equation)−5° C., followed by a wash of 0.2×SSC/0.1% SDS at 60° C.

Angiopoietin-1 may be modified to contain amino acid substitutions, insertions and/or deletions that do not alter the binding and/or activating properties of the protein. Conserved amino acid substitutions involve replacing one or more amino acids of the protein with amino acids of similar charge, size, and/or hydrophobicity characteristics. When only conserved substitutions are made the resulting analog should be functionally equivalent to angiopoietin-1. Non-conserved substitutions involve replacing one or more amino acids of the conjugate protein with one or more amino acids which possess dissimilar charge, size, and/or hydrophobicity characteristics.

Administration or use of a nucleic acid encoding Angiopoietin-1 or variant thereof includes administration or use of a vector containing the nucleic acid molecule and the necessary regulatory sequences for the transcription and translation of the inserted sequence.

Suitable regulatory sequences may be derived from a variety of sources, including bacterial, fungal, viral, mammalian, or insect genes (for example, see the regulatory sequences described in Goeddel, Gene Expression Technology Methods in Enzymology 185, Academic Press, San Diego, Calif. (1990)). Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector. It will also be appreciated that the necessary regulatory sequences may be supplied by angiopoietin-1 sequences and/ or its flanking regions.

The recombinant expression vectors used in the methods and uses described herein may also contain a selectable marker gene which facilitates the selection of host cells transformed or transfected with a recombinant molecule described herein. Examples of selectable marker genes are genes encoding a protein such as G418 and hygromycin which confer resistance to certain drugs, β-galactosidase, chloramphenicol acetyltransferase, firefly luciferase, or an immunoglobulin or portion thereof such as the Fc portion of an immunoglobulin optionally IgG. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors and in particular to determine the effect of a mutation on expression and phenotype. It will be appreciated that selectable markers can be introduced on a separate vector from the nucleic acid of interest.

Recombinant expression vectors can be introduced into host cells to produce a transformed host cell. The term "transformed host cell" is intended to include cells that are capable of being transformed or transfected with a recombinant expression vector of the disclosure. The terms "transduced", "transformed with", "transfected with", "transformation" and "transfection" are intended to encompass introduction of nucleic acid (e.g. a vector or naked RNA or DNA) into a cell by one of many possible techniques known in the art. Prokaryotic cells can be transformed with nucleic acid by, for example, electroporation or calcium-chloride mediated transformation. For example, nucleic acid can be introduced into mammalian cells via conventional techniques such as calcium phosphate or calcium chloride co-precipitation, DEAE-dextran mediated transfection, lipofectin, electroporation, microinjection, RNA transfer, DNA transfer, artificial chromosomes, viral vectors and any emerging gene transfer technologies. Suitable methods for transforming and transfecting host cells can be found in Sambrook et al. (Molecular Cloning: A Laboratory Manual, 2nd Edition, Cold Spring Harbor Laboratory press (1989)), and other laboratory textbooks.

Suitable host cells include a wide variety of eukaryotic host cells and prokaryotic cells. For example, the proteins may be expressed in yeast cells or mammalian cells. Other suitable host cells can be found in Goeddel, Gene Expression Technology: Methods in Enzymology 185, Academic Press, San Diego, Calif. (1991). In addition, the proteins of the disclosure may be expressed in prokaryotic cells, such as *Escherichia coli* (Zhang et al., Science 303(5656): 371-3 (2004)).

Suitable mammalian cells include, among others: 293T cells, COS (e.g., ATCC No. CRL 1650 or 1651), BHK (e.g. ATCC No. CRL 6281), CHO (ATCC No. CCL 61), HeLa (e.g., ATCC No. CCL 2), 293 (ATCC No. 1573) and NS-1 cells.

Suitable expression vectors for directing expression in mammalian cells generally include a promoter (e.g., derived from viral material such as polyoma, Adenovirus 2, cytomegalovirus and Simian Virus 40), as well as other transcriptional and translational control sequences. Examples of mammalian expression vectors include pCDM8 (Seed, B., Nature 329:840 (1987)), pMT2PC (Kaufman et al., EMBO J. 6:187-195 (1987)) and pCMV (Clontech, California, U.S.A.).

Angiopoietin-2 Inhibitors

In another embodiment, the Tie2 binding and/or activating agent comprises an inhibitor of angiopoietin-2.

An "angiopoietin-2 inhibitor" as used herein includes any substance that is capable of inhibiting the expression or activity of angiopoietin-2 and thus, includes substances that inhibit angiopoietin-2 or the interaction of angiopoietin-2 with the Tie2 receptor. Such inhibitors optionally include antisense nucleic acid molecules, siRNAs, proteins, antibodies (and fragments thereof), aptamers, peptibodies, small molecule inhibitors and other substances. In an embodiment, the inhibitor is a blocking antibody or fragment thereof against angiopoietin-2. In one embodiment, the angiopoietin-2 has the amino acid sequence as shown in NP_001138. In another embodiment, the inhibitor is an antisense nucleic acid or an siRNA against an angiopoietin-2 nucleic acid molecule. In one embodiment, the angiopoietin-2 nucleic acid molecule has the nucleic acid sequence as shown in NM_001147.

The term "antisense nucleic acid" as used herein means a nucleic acid that is produced from a sequence that is inverted relative to its normal presentation for transcription. Antisense nucleic acid molecules may be chemically synthesized using naturally occurring nucleotides or variously modified nucleotides designed to increase the biological stability of the molecules or to increase the physical stability of the duplex formed with mRNA or the native gene e.g. phosphorothioate derivatives and acridine substituted nucleotides. The antisense sequences may be produced biologically using an expression vector introduced into cells in the form of a recombinant plasmid, phagemid or attenuated virus in which antisense sequences are produced under the control of a high efficiency regulatory region, the activity of which may be determined by the cell type into which the vector is introduced.

The term "siRNA" refers to a short inhibitory RNA that can be used to silence gene expression of a specific gene. The siRNA can be a short RNA hairpin (e.g. shRNA) that activates a cellular degradation pathway directed at mRNAs corresponding to the siRNA. Methods of designing specific siRNA molecules and administering them are known to a person skilled in the art. It is known in the art that efficient silencing is obtained with siRNA duplex complexes paired to have a two nucleotide 3' overhang. Adding two thymidine nucleotides is thought to add nuclease resistance. A person skilled in the art will recognize that other nucleotides can also be added.

The term "aptamer" as used herein refers to short strands of nucleic acids that can adopt highly specific 3-dimensional conformations. Aptamers can exhibit high binding affinity and specificity to a target molecule. These properties allow such molecules to specifically inhibit the functional activity of proteins. Thus, in another embodiment, the Ang2 inhibitor is an aptamer that binds and inhibits Ang2 activity.

The term "peptibody" as used herein refers to a recombinant protein that fuses a peptide region with the Fc region of IgG. Thus, in another embodiment, the Ang2 inhibitor is an Ang2 peptide inhibitor fused with the Fc region of IgG.

The term "antibody" as used herein is intended to include monoclonal antibodies, polyclonal antibodies, and chimeric antibodies. The antibody may be from recombinant sources and/or produced in transgenic animals. The term "antibody fragment" as used herein is intended to include without limitations Fab, Fab', F(ab')2, scFv, dsFv, ds-scFv, dimers, minibodies, diabodies, and multimers thereof, multispecific antibody fragments and domain antibodies. Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, dsFv, ds-scFv, dimers, minibodies, diabodies, bispecific antibody fragments and other fragments can also be synthesized by recombinant techniques.

Conventional methods can be used to prepare antibodies. For example, by using a peptide from angiopoietin or Tie2, polyclonal antisera or monoclonal antibodies can be made using standard methods. A mammal, (e.g., a mouse, hamster, or rabbit) can be immunized with an immunogenic form of the peptide which elicits an antibody response in the mammal. Techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art, (e.g., the hybridoma technique originally developed by Kohler and Milstein (Nature 256:495-497, 1975) as well as other techniques such as the human B-cell hybridoma technique (Kozbor and Roder, Immunology Today 4:3, 72-79, 1983), the EBV-hybridoma technique to produce human monoclonal antibodies (Cole et al., "The EBV-Hybridoma Technique and its Application to Human Lung Cancer" in "Monoclonal Antibodies in Cancer Therapy", Allen R. Bliss, Inc. (1985), pages 77-96) and screening of combinatorial antibody libraries (Huse et al. Science 246:4935, 1275-1282, 1989). Hybridoma cells can be screened immunochemically for production of antibodies specifically reactive with the peptide and the monoclonal antibodies can be isolated. Therefore, the disclosure also contemplates hybridoma cells secreting monoclonal antibodies with specificity for angiopoietin-2 or Tie2.

Chimeric antibody derivatives, i.e., antibody molecules that combine a non-human animal variable region and a human constant region are also contemplated. Chimeric antibody molecules can include, for example, the antigen binding domain from an antibody of a mouse, rat, or other species, with human constant regions. Conventional methods may be used to make chimeric antibodies containing the immunoglobulin variable region which recognizes angiopoietin-2 or Tie2 protein (See, for example, Morrison et al. (PNAS 81:21, 6851-6855, 1984), and Takeda et al. (Nature 314:452-454), and the patents of Cabilly et al., U.S. Pat. No. 4,816,567; Boss et al., U.S. Pat. No. 4,816,397; Tanaguchi et al., European Patent Publication No. EP171496; European Patent Publication No. 0173494, United Kingdom patent GB 21770966).

Monoclonal or chimeric antibodies specifically reactive with angiopoietin-2 or Tie2 as described herein can be further humanized by producing human constant region chimeras, in which parts of the variable regions, particularly the conserved framework regions of the antigen-binding domain, are of human origin and only the hypervariable regions are of non-human origin. Such immunoglobulin molecules may be made by techniques known in the art, (e.g., Teng et al. (1983) Proc. Natl. Acad. Sci. 80:12, 7308-7312), Kozbor and Roder (1983) Immunology Today 4:3, 72-79; Olsson et al. (1982) Methods in Enzymol. 92, 3-16, PCT Patent Application Publication No. WO92/06193 and EP Patent Application Publication No. 0 239 400). Humanized antibodies can also be commercially produced (Scotgen Limited, 2 Holly Road, Twickenham, Middlesex, Great Britain.)

Specific antibodies, or antibody fragments, reactive against angiopoietin-2 or Tie2 may also be generated by screening expression libraries encoding immunoglobulin genes, or portions thereof, expressed in bacteria with peptides produced from the nucleic acid molecules encoding a angiopoietin-2 or Tie2. For example, complete Fab fragments, VH regions and FV regions can be expressed in bacteria using phage expression libraries (See for example Ward et al. (1989) Nature 348:544-546, Huse et al. (1989) Science 246:4935, 1275-1282, and McCafferty et al. (1989) Nature 348, 552-555).

Antibodies may also be prepared using DNA immunization. For example, an expression vector containing a nucleic acid encoding angiopoietin-2 may be injected into a suitable animal such as mouse. The protein will therefore be expressed in vivo and antibodies will be induced. The antibodies can be isolated and prepared as described above for protein immunization.

The angiopoietin-2 inhibitors, the angiopoietin-1 peptides or the Tie2 binding peptides described herein may also contain or be used to obtain or design "peptide mimetics". For example, a peptide mimetic may be made to mimic the function of an angiopoietin-2 inhibitor. "Peptide mimetics" are structures which serve as substitutes for peptides in interactions between molecules (See Morgan et al. (1989), *Ann. Reports Med. Chem.* 24, 243-252 for a review). Peptide mimetics include synthetic structures which may or may not contain amino acids and/or peptide bonds but retain the structural and functional features of the protein, including binding to and/or activating Tie2. Peptide mimetics also include peptoids, oligopeptoids (Simon et al. (1992) Proc. Natl. Acad. Sci. 89, 9367-9371).

Peptide mimetics may be designed based on information obtained by systematic replacement of L-amino acids by D-amino acids, replacement of side chains with groups having different electronic properties, and by systematic replacement of peptide bonds with amide bond replacements. Local conformational constraints can also be introduced to determine conformational requirements for activity of a candidate peptide mimetic. The mimetics may include isosteric amide bonds, or D-amino acids to stabilize or promote reverse turn conformations and to help stabilize the molecule. Cyclic amino acid analogues may be used to constrain amino acid residues to particular conformational states. The mimetics can also include mimics of the secondary structures of the proteins described herein. These structures can model the 3-dimensional orientation of amino acid residues into the known secondary conformations of proteins. Peptoids may also be used which are oligomers of N-substituted amino acids and can be used as motifs for the generation of chemically diverse libraries of novel molecules.

Tie2 Binding Peptides Monomers and Multimeric Forms

In another embodiment, the Tie2 binding and/or activating agent for use in the methods and uses described herein comprises a Tie2 binding peptide monomer or a multimeric form thereof.

In one embodiment, the multimeric form comprises an even number of units of the monomer. In another embodiment, the multimeric form is a tetramer. In yet another embodiment, the multimeric form is a dimer. In yet other embodiments, the multimeric form comprises six, eight, ten or twelve units of the Tie2 binding peptide monomer. In another embodiment, the multimeric form comprises an odd number of units of the monomer. For example, the multimeric form can be a trimer or the multimeric form can comprise five, seven, nine or eleven units of the Tie2 binding peptide monomer. In a particular embodiment, the multimeric form is a tetramer.

The Tie2 binding peptide contained within the monomer is at least two amino acids in length, is at least five amino acids in length or is at least seven amino acids in length. An optional size range for the peptide is 7-25 amino acids in length, or 7-15 amino acids in length. Other size ranges include 5-30 amino acids in length, 5-40 amino acids in length, 5-50 amino acids in length, 5-60 amino acids in length, 5-70 amino acids in length, 5-80 amino acids in length, 5-90 amino acids in length or 5-100 amino acids in length. Optionally, the peptide is no more than 100 amino acids in length.

In one embodiment, the Tie2 binding peptide within the monomer comprises an amino acid sequence that is present in a native Tie2 ligand (e.g., an angiopoietin, such as Ang 1 or Ang 2). For example, a fragment of an angiopoietin that retains the ability to bind to Tie2 can be used as the Tie2 binding peptide. Alternatively, in another embodiment, the Tie2 binding peptide within the monomer comprises an amino acid sequence that is not present in a native Tie2 ligand. It has been shown that peptides having amino acid sequences that differ from the primary sequence of angiopoietins can be selected that have affinity for Tie2 (see e.g., Tournaire, R. et al. (2004) *EMBO Reports* 5, 262-267). Such peptides can be identified, for example, by screening of a phage displayed peptide library (e.g., a random 7-mer library) for peptides that bind to Tie2 (e.g., a Tie2-Fc fusion protein), with confirmation of peptide binding to Tie2 by screening of the selected peptide for binding to Tie2 using an ELISA assay (e.g., as described in Tournaire, R. et al. (2004) supra).

In an embodiment, the Tie2 binding peptide used in the monomer binds to Tie2 with high affinity but does not substantially inhibit binding of an angiopoietin to Tie2. In such an embodiment, the multimeric form does not compete with native angiopoietins for binding to Tie2. For example, the Tie2 binding peptide binds to Tie2 with high affinity but does not substantially inhibit the binding of Ang 1 to Tie2. Additionally or alternatively, the Tie2 binding peptide binds to Tie2 with high affinity but does not substantially inhibit the binding of, for example, Ang 2 or Ang 4, to Tie2.

In an embodiment, the Tie2 binding peptide monomer comprises a T7 peptide, which T7 peptide comprises an amino acid sequence: His-His-His-Arg-His-Ser-Phe (SEQ ID NO: 1). In one embodiment, the T7 peptide has an amino terminal cysteine residue added to it and, thus, in this embodiment, the T7 peptide comprises an amino acid sequence: Cys-His-His-His-Arg-His-Ser-Phe (SEQ ID NO: 2).

In another embodiment, the Tie2 binding peptide monomer comprises a GA3 peptide, which GA3 peptide comprises an amino acid sequence: Trp-Thr-Ile-Ile-Gln-Arg-Arg-Glu-Asp-Gly-Ser-Val-Asp-Phe-Gln-Arg-Thr-Trp-Lys-Glu-Tyr-Lys (SEQ ID NO: 3). In one embodiment, the GA3 peptide has an amino terminal cysteine residue added to it and, thus, in this embodiment, the GA3 peptide comprises an amino acid sequence: Cys-Trp-Thr-Ile-Ile-Gln-Arg-Arg-Glu-Asp-Gly-Ser-Val-Asp-Phe-Gln-Arg-Thr-Trp-Lys-Glu-Tyr-Lys (SEQ ID NO: 4).

In yet another embodiment, the Tie2 binding peptide monomer comprises a T8 peptide, which T8 peptide comprises an amino acid sequence: His-Pro-Trp-Leu-Thr-Arg-His (SEQ ID NO: 5). In one embodiment, the T8 peptide has an amino terminal cysteine residue added to it and, thus, in this embodiment, the T8 peptide comprises an amino acid sequence: Cys-His-Pro-Trp-Leu-Thr-Arg-His (SEQ ID NO: 6).

In yet another embodiment, the Tie2 binding peptide monomer comprises a T6 peptide, which T6 peptide comprises an amino acid sequence: Lys-Leu-Trp-Val-Ile-Pro-Lys (SEQ ID NO: 7). In one embodiment, the T6 peptide has an amino terminal cysteine residue added to it and, thus, in this embodiment, the T6 peptide comprises an amino acid sequence: Cys-Lys-Leu-Trp-Val-Ile-Pro-Lys (SEQ ID NO: 8).

In another embodiment, the Tie2 peptide binding monomer comprises a T4 peptide, which T4 peptide comprises an amino acid sequence: Asn-Leu-Leu-Met-Ala-Ala-Ser (SEQ ID NO: 9). In one embodiment, the T4 peptide has an amino terminal cysteine residue added to it and, thus, in this embodiment, the T4 peptide comprises an amino acid sequence: Cys-Asn-Leu-Leu-Met-Ala-Ala-Ser (SEQ ID NO: 10).

The Tie2 binding peptides T4, T6, T7 and T8 also are described in Tournaire, R. et al., (2004) *EMBO Reports* 5, 262-267. The Tie2 binding peptide GA3 also is described in Wu, X. et al. (2004) *Biochem. Biophys. Res. Commun.* 315, 1004-1010.

The Tie2 binding peptides described herein may be modified to contain amino acid substitutions, insertions and/or deletions that do not alter the peptides ability to bind and/or activate Tie2. Conserved amino acid substitutions involve replacing one or more amino acids of the peptide with amino acids of similar charge, size, and/or hydrophobicity characteristics. When only conserved substitutions are made the resulting analog should be functionally equivalent to the peptide. Non-conserved substitutions involve replacing one or more amino acids of the peptide with one or more amino acids which possess dissimilar charge, size, and/or hydrophobicity characteristics.

The Tie2 binding peptides described herein may be modified to make them more therapeutically effective or suitable. For example, the peptides may be converted into pharmaceutical salts by reacting with inorganic acids including hydrochloric acid, sulphuric acid, hydrobromic acid, phosphoric acid, etc., or organic acids including formic acid, acetic acid, propionic acid, glycolic acid, lactic acid, pyruvic acid, oxalic acid, succinic acid, malic acid, tartaric acid, citric acid, benzoic acid, salicylic acid, benzenesulphonic acid, and toluenesuiphonic acids.

In addition to the Tie2 binding peptide, the Tie2 binding peptide monomer can comprise other chemical moieties or groups, such as spacers and/or multimerizing groups. For example, the Tie2 binding peptide can be linked to a spacer, which may serve one or more functionalities. The spacer can, for example, function to increase the distance between the monomers when they are multimerized to facilitate interaction of the multimeric form with the Tie2 receptor (e.g., reduce steric hindrance). Additionally or alternatively, the spacer can, for example, serve as a chemical group by which the monomers can be multimerized and/or can contribute to the pharmacodynamics/pharmacokinetics of the compound.

Moreover, the Tie2 binding peptide monomer can comprise one or more multimerizing groups, chemical moieties that function to facilitate multimerization of the monomers. A particular multimerizing group is a biotin group, which has affinity for avidin, streptavidin and neutravidin such that any of the three latter compounds can be used for multimerization of monomers comprising a biotin group. Another example of a multimerizing group is a coiled coil domain, which can be linked to the amino terminus of the peptide through standard recombinant DNA engineering techniques and which self-assembles into oligomeric structures (see e.g., U.S. Patent Application Publication Nos. 2003/0220476 and 2006/0074230 for further description of the use of coiled coil domains for multimerization). Non-limiting examples of coiled coil domains suitable for use are the coiled coil domains from the yeast transcription factor GCN4, from cartilage matrix protein (CMP) or from cartilage oligomeric matrix protein (COMP).

In one embodiment, the spacer is a polyethylene glycol (PEG) spacer, which is a polymeric molecule that can contain different numbers of units, such as 2, 4, 6, 8, 10, 11 or 12 units. PEG polymers are also known in the art as polyethylene oxide (PEO) polymers and thus the terms PEG and PEO as used herein are intended to be equivalent. Numerous other suitable spacers (also known as linkers) are well known in the art, non-limiting examples of which include other polyalkylene glycols, polyesters and polyalkylene amines. Moreover, a wide variety of spacers linked on one end to a reactive moiety and on the other end to a biotin group are commercially available (EZ-Link Biotin reagents available from Pierce Chemical Co., Rockford, Ill., USA) and can be used in the preparation of the Tie2 binding peptide monomers used with the methods and uses described herein. Non-limiting examples of commercially available reagents of the structure: reactive moiety-spacer-biotin include:
Sulfhydryl Reactive Reagents:
EZ-Link Biotin-BMCC (1-Biotinamido-4-(4'-[maleimidoethyl-cyclohexane]-carboxamido)butane)
EZ-Link Biotin-HPDP (N-(6-(Biotinamido)hexyl)-3'-(2'-pyridyldithio)-propionamide
EZ-Link Iodoacetyl-LC-Biotin (N-iodoacetyl-N-biotinyl-hexylenediamine)
EZ-Link Iodoacetyl-$PEO_2$ Biotin ((+)-Biotinyl-iodoacetamidyl-3,6-dioxaoctanediamine)
EZ-Link Maleimide $PEO_n$-Biotin (n=2 or 11)
Amine Reactive Reagents:
EZ-Link NHS-$PEO_n$-Biotin (n=4 or 12)
EZ-Link NHS-SS-Biotin (succinimidyl 2-(biotinamido)-ethyl-1,3'-dithiopropionate)
EZ-Link Sulfo-NHS-LC-Biotin (Sulfosuccinimidyl-6-(biotinamido) hexanoate)
EZ-Link TFP-$PEO_3$-Biotin (Tetrafluorophenyl Ester $PEO_3$—biotin)
Carboxyl Reactive Reagents:
EZ-Link 5-(Biotinamido)pentylamine
EZ-Link Amine-$PEO_2$-Biotin Labeling Reagent ((+)-Biotinyl-3,6-dioxaoctanediamine)
EZ-Link Amine-$PEO_3$-Biotin Labeling Reagent ((+)-Biotinyl-3,6,9-trioxaundecanediamine)
EZ-Link Biotin PEO-Amine ((+)-Biotinyl-3,6-dioxaoctanediamine)
EZ-Link Biotin-PEO-LC-Amine ((+)-Biotinyl-3,6,9-trioxaundecanediamine)

Furthermore, a branched arm spacer can be linked to multiple copies of the Tie2 binding peptide as a means to multimerize the peptide. Non-limiting examples include 2 and 4 armed activated branched PEG spacers, although spacers with more arms, such as 8 or 12 armed activated branched PEG spacers also can be used. Branched activated PEG spacers (e.g., activated with maleimide) are commercially available (e.g., NOF Corporation, Tokyo, Japan).

In an embodiment, the Tie2 binding peptide monomer comprises a structure: A-B-C, wherein A comprises a Tie2 binding peptide, B comprises a spacer and C comprises a multimerizing group, wherein C has affinity for D, a multimer agent comprising multiple binding sites for C. In one embodiment, the multimer agent D has four binding sites for the multimerizing group C such that a tetramer is formed when four Tie2 binding peptide monomers, A-B-C, interact with the multimer agent D. In an embodiment, the multimerizing group, C, for use in creating tetramers is a biotin group. Optional multimer agents, D, for use in creating tetramers are avidin, streptavidin and neutravidin. It is well known in the art that avidin, streptavidin and neutravidin have four binding sites for biotin and that biotin binds with high affinity to each of avidin, streptavidin and neutravidin. An optional spacer, B, for use in a monomer of the structure A-B-C is a polyethylene glycol (PEG) spacer.

In another embodiment, the Tie2 binding peptide monomer comprises a structure: A-B, wherein A comprises a Tie2 binding peptide and B comprises a spacer, wherein the multimeric form is created by covalent linkage of multiple Tie2 binding peptide monomers via the spacer B. An optional spacer, B, for use in a monomer of the structure A-B is a polyethylene glycol (PEG) spacer.

In yet another embodiment, the Tie2 binding peptide monomer comprises a structure: A-B-C, wherein:
A comprises a Tie2 binding peptide selected from a T7 peptide and a GA3 peptide;
B comprises a polyethylene glycol spacer; and
C comprises a biotin group,
wherein four copies of A-B-C are associated with a tetramer agent, D, to create the tetramer form, the tetramer agent, D, being selected from the group consisting of avidin, streptavidin and neutravidin. A specific example of this embodiment is a compound in which A comprises a T7 peptide, B comprises a polyethylene glycol spacer and C comprises a biotin group, and wherein the tetramer agent D comprises avidin.

In yet another embodiment, the Tie2 binding peptide monomer comprises a structure A-B-C, wherein:
A comprises a Tie2 binding peptide;
B comprises a spacer; and
C comprises a multimerizing group.
Optionally, the Tie2 binding peptide, A, comprises a T7 peptide or a GA3 peptide. Alternatively, the Tie2 binding peptide can comprise, for example, a T8 peptide, a T6 peptide or a T4 peptide. In an embodiment, the spacer, B, comprises a polyethylene glycol spacer. In another embodiment, the multimerizing group, C, comprises a biotin group.

In yet a further embodiment, the multimeric form for use in the methods and uses described herein comprises a peptide dimer, comprising: (a) a first peptide chain; (b) a second peptide chain; and (c) a linking moiety connecting said first and second peptide chains, wherein said peptide dimer binds to and activates the Tie2 receptor. Optionally, the first peptide chain is a T7 peptide and/or the second peptide chain is a T7 peptide. In an embodiment, both the first and second peptide chains are T7 peptides. Alternatively, the first and second peptide chains independently can be selected from the group consisting of a T7 peptide, a GA3 peptide, a T4 peptide, a T6 peptide and a T8 peptide. In an embodiment, the first and second peptide chains are both the same type of peptide chain. Additional Tie2 binding peptides that can be used are described in further detail above.

Optionally, the linking moiety comprises one or more water soluble polymers covalently bound to the first peptide chain and the second peptide chain. In one embodiment, the one or more water soluble polymers are linear polymers. Optionally, the water soluble polymer is a polyethylene glycol (PEG) (e.g., a linear PEG molecule). The PEG can have a molecular weight of less than about 50,000 Daltons. In one embodiment, the linear PEG has a molecular weight in the range of about 3,000 Daltons to about 20,000 Daltons. In various embodiments, the linear PEG has a molecular weight of about 3,000 Daltons, about 3,400 Daltons, about 5,000 Daltons or about 10,000 Daltons. It is understood that in a given preparation of PEG, the molecular weights will typically vary among individual molecules. Some molecules will weigh more, and some less, than the stated molecular weight. Such variation is generally reflected by use of the word "about" to describe the molecular weights of the PEG molecules.

In another embodiment, the multimeric form comprises dimers utilizing a linear PEG linker having a molecular weight less than about 20,000 Da, or having a molecular weight in the range of about 3,000 Daltons to about 10,000 Da.

In another embodiment, the multimeric form comprises a peptide tetramer, comprising: (a) a first peptide chain; (b) a second peptide chain; (c) a third peptide chain; (d) a fourth peptide chain; and (e) a linking moiety connecting said first, second, third and fourth peptide chains, wherein said peptide tetramer binds to and activates the Tie2 receptor. In one embodiment, the first, second, third and fourth peptide chains are T7 peptides. Alternatively, the first, second, third and fourth peptide chains independently can be selected from the group consisting of a T7 peptide, a GA3 peptide, a T4 peptide, a T6 peptide and a T8 peptide, and optionally the first, second, third and fourth peptide chains are all the same type of peptide chain. Additional Tie2 binding peptides that can be used are described in further detail above.

In such an embodiment, the linking moiety comprises one or more water soluble polymers covalently bound to the first, second, third and fourth peptide chains. In one embodiment, the one or more water soluble polymers are branched chain polymers, such as a polyethylene glycol (PEG) (e.g., a branched chain PEG molecule). Optionally, the branched PEG has a molecular weight in the range of about 3,000 Daltons to about 50,000 Daltons. In various embodiments, the branched PEG has a molecular weight of about 3,000 Daltons, about 3,400 Daltons, about 5,000 Daltons, about 10,000 Daltons, about 20,000 Daltons, about 25,000 Daltons, about 30,000 Daltons, or about 40,000 Daltons. It is understood that in a given preparation of PEG, the molecular weights will typically vary among individual molecules. Some molecules will weigh more, and some less, than the stated molecular weight. Such variation is generally reflected by use of the word "about" to describe the molecular weights of the PEG molecules.

In the PEG-containing dimers, a single, optionally linear, PEG moiety is simultaneously attached to the termini (e.g., the N-termini) of both peptide chains of the peptide dimer. In the PEG-containing tetramers, a single, branched chain PEG moiety is simultaneously attached to the termini of the four peptide chains of the peptide tetramer. To prepare the PEG-containing dimeric and tetrameric compounds described above, Tie2 binding peptides can be reacted with activated PEG linkers (e.g., PEG dimaleimide for preparation of dimers, PEG tetramaleimide for preparation of tetramer. Such activated PEG linkers (linear or branched chain) are commercially available (e.g., from NOF America Corporation).

In addition to the dimers and tetramers described above, other multimeric forms comprising two or more Tie2 binding peptides linked by a linking moiety can be used, such as those containing three, five, six, seven, eight, nine, ten, eleven or twelve Tie2 binding peptides covalently linked to a linking moiety, optionally a branched linking moiety, such as a branched chain PEG molecule. Such alternative multimeric forms can be prepared as described for the dimers and tetramers, using linker moieties having the appropriate number of reactive ends (e.g., six reactive ends for a multimer containing six peptide chains) and the appropriate ratio of peptide to linker (e.g., 6:1 for a multimer containing six peptide chains).

Alternative water soluble polymer linkers include, but are not limited to, copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), poly(n-vinyl pyrrolidone)polyethylene glycol, propropylene glycol homopolymers, polypropylene oxide/ethylene oxide copolymers, and polyoxyethylated polyols. For peptide dimers, the polymer linker can have a molecular weight of less than 20,000 Da. In one embodiment, the molecular weight is about 10,000 Da. For peptide tetramers, the polymer linker has a molecular weight of about 20,000 Da.

Other types of linking moieties known in the art can be used to join the peptide chains in the multimers (e.g., two peptide chains in the dimer, four peptide chains in the tetramer). Non-limiting examples of additional suitable linker moieties that can be used to join multiple peptide chains to form multimers include those described in US Patent Application Publication Nos. 2007/0104704 and US Publication 2007/0027074, the entire contents of both of which are expressly incorporated herein by reference.

The above disclosure generally describes the present disclosure. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1

Materials and Methods

Generation, Genotyping and Treatment of Transgenic Mice

Briefly, construction of the driver transgene, pTek-tTA, and the responder transgenes, pTetOS-Tek, pTetos-Ang1, and pTetos-Ang2 have been described previously. All transgenic lines were maintained and genotyped as previously described (Voskas et al. (2005) Am. J. Pathol. 166(3):843-855, Ward et al. (2004) Am. J. Pathol. 165(3):889-899, Bureau et al. (2006) Am. J. Physiol. Heart Circ. Physiol. 291(2):H948-965). Males were housed with a single female for 14 to 20 days and then separated into individual cages. CD1 mice (an outbred mouse line) were maintained in a barrier facility. All adult mice used in these studies were 2 to 6 months old.

Morphological, Histochemical and Immunohistochemical Analysis

Mouse skin tissue was fixed in 4% paraformaldehyde (Sigma, St. Louis, Mo.) for 16 hours at 4 degrees Celsius, and transferred to 70% ethanol. Tissues were subsequently paraffin embedded and sectioned at 4 μM on SuperFrost glass slides. Tissue slides were stained for hematoxylin and eosin using standard techniques. For immunohistochemistry, anti-E-Selectin (rat; Pharmingen, La Jolla, Calif.), anti-VCAM1 (rat; Pharmingen), anti-ICAM1 (Hamster; Pharmingen, La Jolla, Calif.), primary antibodies were detected using biotinylated secondary antibodies as described in the Vectastain Elite ABC kit (Vector Laboratories, Burlingame, Calif.). Slides were processed and counterstained with methyl green using standard techniques. Slides were analyzed and photos were processed using a Leica compound light microscope coupled to a Leica DFC300FX camera (Wetzlar, Germany). Skin tissue was taken (biopsy) at day 0, prior to initiation of treatment and at 30 days. Gross phenotypic examination was conducted and mice were photographed in a standard format using a Digital Canon Eos Rebel.

Methocult Colony Assay

Bone marrow was flushed from the femur bones of two month old CD1 mice and was suspended in Iscove's Modified Dulbecco's Media (Sigma, St. Louis, Mo.) at a concentration of $1 \times 10^5$ per ml. Cells were thoroughly suspended in methocellulose M3434 media (Stem Cell Technologies, Vancouver, BC) such that $1 \times 10^4$ cells per 35 mm tissue culture dish were dispensed. Prior to dispensing into the tissue culture dishes either vehicle (PBS) or Vasculotide 1 ng/ml or 10 ng/ml was mixed in. Plates were placed in an incubator at 37° C., 5% $CO_2$ for 7 days without replenishment of vehicle or Vasculotide. After 7 days the plates were enumerated for CFU-G.

Blood Collection and FACs Analysis

Blood was collected from all mice on day 0 (prior to treatment) and day 30 (after 30 days of treatment). On day 0, approximately 50 μl was collected via tail vein puncture into a lithium heparin micro tube. Day 30 blood was collected via cardiac puncture into a lithium heparin micro tube. Both blood samples were prepared for storage and subsequent analysis using Phosflow Lyse/Fix Buffer (BD Biosciences, Franklin Lakes, N.J.), according to manufacturers instructions. Cells were stained for IgE versus free FITC and characteristic populations of basophils and eosinophils were identified.

Drug Preparation (Vasculotide) and Analysis

Modified T7 peptide (CHHHRHSF) (SEQ ID NO:2) was reacted at room temperature with a 10 kDa tetrameric polyethylene glycol-maleimide (NOF corporation, Japan) in a 12:1 molar ratio (w/w) for 4 hrs suspended in phosphate buffered saline (PBS) (Sigma, St. Louis, Mo.) pH 6.8. Reactants were dialysed in a 7,000 Da molecular weight dialysis cassette (Slide-A-Lyzer, Thermo Scientific, Rockford, Ill.). Dialysis was with PBS, pH 7.4 initially (2 exchanges at 800× volume, every 4 hours) and then 6 exchanges of double distilled water over a 48 hour period (6 exchanges at 800× volume). Dialysed product was frozen at −80 degrees Celsius and then lyophilized. The dried product was resuspended in sterile PBS, pH 7.4. A small portion of the product was analysed by MALDI TOF to determine the efficiency of T7 peptide conjugation to the 10 kDa tetrameric polyethylene glycol-maleimide.

Drug Treatments

Normal and double transgenic (pTek-tTA:pTetOS-Tek) CD1 mice were injected intra peritoneally with either sterile PBS, pH 7.4 (vehicle) or Vasculotide (40 μg/kg) every three days for the period of 30 days. Mice were observed closely during this period for phenotypic resolution and/or any potential ill effects.

Cytometric Bead Array Analysis

Plasma was collected in lithium/heparin microtubes from all mice following 30 days of treatment with Vasculotide or vehicle. Plasma was diluted 1:8 in sample diluent (BD Biosciences, Franklin Lakes, N.J.). A multiplex analysis of 12 different mouse cytokines was examined according to manufacturer's instructions. Analysis and cytokine/chemokine quantification was performed using the manufacturers FCAP software package (BD Biosciences, Franklin Lakes, N.J.).

Antibodies for Western Blotting and Immunoprecipitation

The following commercially available antibodies were used: monoclonal anti-Tie2 (Phaminogen), polyclonal anti-Tie2 (Santa Cruz Biotechnology) and monoclonal anti-pY (clone 4G10, Upstate Biotechnology). Lung lysates were prepared and immunoprecipitated in full RIPA buffer (50 mM Tris-HCl, pH 7.4, 150 mM NaCl, 1 mM PMSF, 1 mM EDTA, 5 μg/ml Aprotinin 5 μg/ml Leupeptin, 1% Triton x-100, 1% Sodium deoxycholate, 0.1% SDS). Proteins were resolved in 10% PAGE according to Laemlli and transferred to PVDF membrane for subsequent antibody probing.

Eotaxin Quantification (ELISA)

Blood was collected from mice as previously described. Separated plasma was diluted 1:4 in calibrator diluent according to manufacturer's specifications (R&D Biosystems, Minneapolis, Minn. USA). All aspects of the assay were conducted according to manufacturer's directions. Quantification of plasma eotaxin concentrations was performed by linear regression analysis from assessment of defined amounts of eotaxin standard.

Results:

Vasculotide Activates Tie2 In Vivo

Purified Vasculotide was examined for its ability to activate the Tie2 receptor tyrosine kinase in CD1 mice (FIG. 1A). Three mice per group were injected intraperitoneally (IP) with either Vasculotide (500 ng-12.5 μg) or vehicle (PBS) control. After one hour, mice were sacrificed and lung homogenates were prepared for immunoblot analysis. A dose of 500 ng/25-30 g mouse of Vasculotide activated Tie2 optimally (see pY Tie2, upper panel) in CD1 mice after 1 hour in circulation while higher doses appeared to have reduced receptor-activating activity. This effect is particularly evident when total protein loading is accounted for (see pan Tie2, lower panel). While this may seem somewhat paradoxical, this phenomenon has also been reported by others while investigating the effect of Ang1 on Tie2 activation (Brkovic et al. (2007) J. Leukoc. Biol. 81(4), 1093-1101), Sturn et al. (2005) Microcirculation 12(5), 393-403, Murdoch et al. (2007) J Immunol 178(11), 7405-7411, van der Geer et al. (1994) Ann. Rev. Cell Biol. 10, 251-337, Gruber et al. (1995) Blood 86(7), 2488-2493, Maliba et al. (2008) J. Leukoc. Biol. 83(2), 352-360, and Van Slyke et al. (2009) Tissue Eng. Part A 15(6), 1269-1280).

Assessment of Vasculotide-Dependent Tie2 Activation Kinetics

Figure 1B:
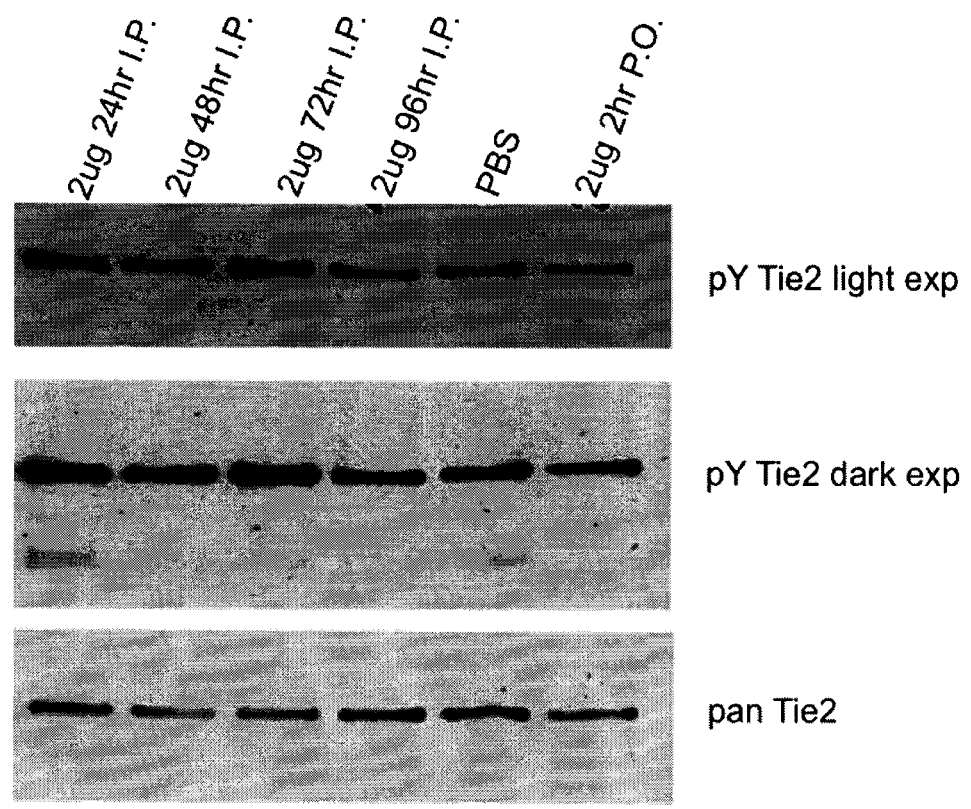
FIG. 1B shows Vasculotide-driven Tie2 receptor activation in vivo. Tie2 activation (pY Tie2) was quantified at various times following intraperitoneal injection (I.P.) or gavage (P.O.) of Vasc-PEG into CD1 mice. Lysates were extracted from the lungs and Tie2 phosphorylation analysis performed on pooled lysates from three animals subjected to immunoprecipitation. Increased Tie2 phosphorylation is apparent for at least 72 hrs following I.P. injection.

To assess the duration of Tie2 activation following Vasculotide administration, three mice per time point were injected with 2 μg intraperitoneally (I.P.) or by gavage (P.O.). Lung lysates were prepared from each of the mice at the indicated times following initial dosing (FIG. 1B). Equal quantities of protein from each group were pooled and immunoprecipitated for Tie2 to establish an average Tie2 activation for each group. Activation of Tie2 (see pY Tie2, upper panels) was evident at time points ranging from 24-72 hours in the I.P. injected mice. By 96 hours post injection, the Tie2 receptor phosphorylation had returned to basal (PBS stimulated) levels. Assessment of the oral availability of Vasculotide did not yield increased activation of Tie2 phosphorylation two hours post gavage. These results suggest that Vasculotide, in its current formulation, is not compatible with oral delivery but is deliverable intraperitoneally.

Detection of Circulating Vasculotide in Mouse Plasma

Figure 1C:
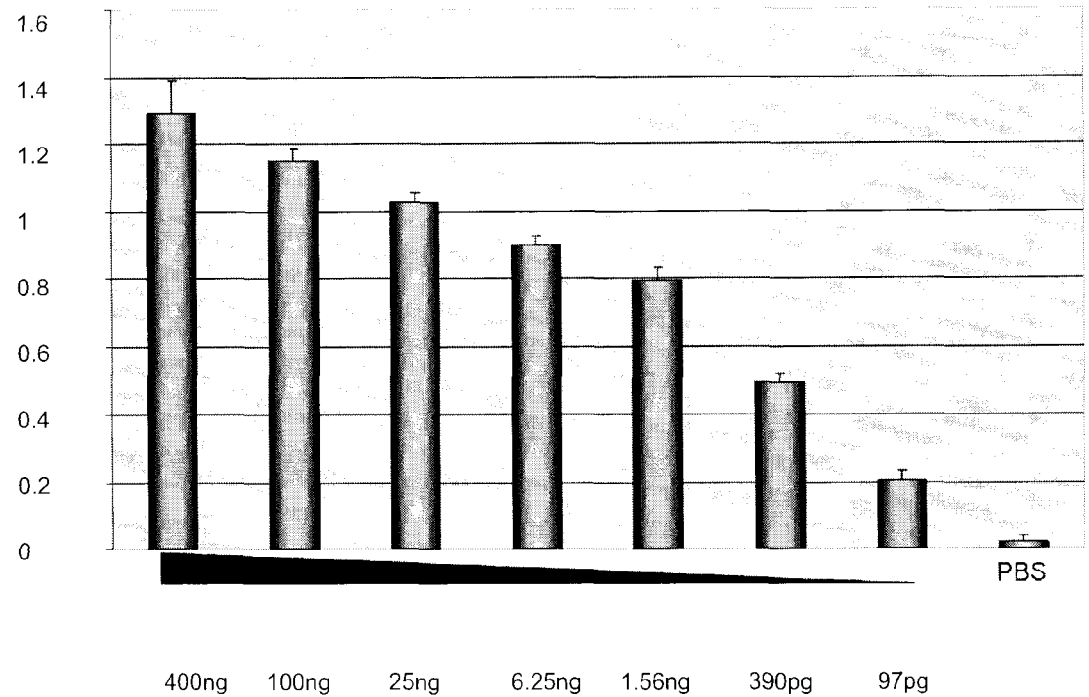
FIG. 1C shows detection and quantification of Vasculotide by ELISA. A typical standard curve is shown in which a defined amount of compound is spiked into diluted mouse plasma. PBS is used as a negative control. Vasculotide concentrations examined ranged from 97 pg to 400 ng. Concentrations of Vasculotide falling within this range displayed a high degree of linearity.

Several monoclonal antibodies have been raised against the modified T7 peptide. These antibodies have been extensively validated and used to develop an ELISA which is capable of measuring picogram quantities of Vasculotide in mouse plasma or serum. There is an excellent linear relationship between ELISA signal and Vasculotide concentration with little interference from mouse plasma/serum proteins (FIG. 1C).

Figure 1D:
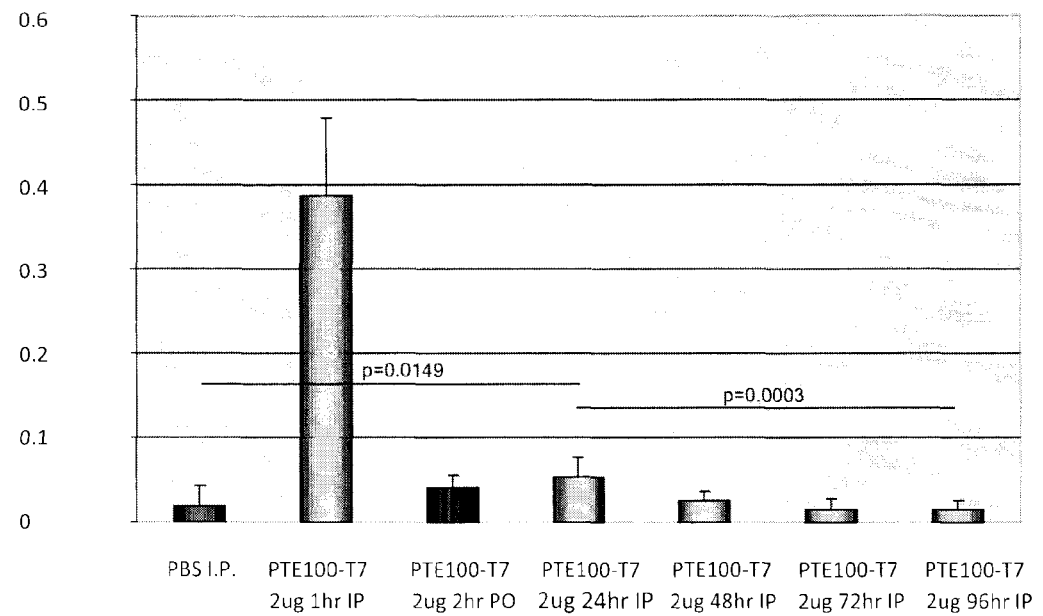
FIG. 1D shows results of Vasculotide-specific ELISA to assess Vasc-PEG persistence in circulation. Circulating Vasc-PEG (plasma) was quantified at various times following intraperitoneal injection (I.P.) or gavage (P.O.) into CD1 mice. At 24 hours post injection, a statistically detectable level of Vasc-PEG (determined by unpaired student t-test) was observed in the plasma (compare PBS to 24 hrs or 24 hrs to 96 hrs). Oral delivery did not result in any detectable levels of Vasc-PEG when compared to PBS.

The developed ELISA was used to track circulating levels of Vasculotide in the plasma of mice over time. Results showed that despite activation of Tie2 at 72 hours following a 2 µg dose of Vasculotide detectable by immunoblot analysis (FIG. 1B), the ELISA is only capable of detecting significant ($p=0.0149$, PBS vs Vasc) levels of circulating Vasculotide up to 24 hours (FIG. 1D). The incongruence of these findings is likely due to a paucity of sensitivity in the ELISA-based detection of Vasculotide. Furthermore, these findings suggest that minute quantities of Vasculotide may be all that is required to drive sustained Tie2 activation. Consistent with the lack of Tie2 activation noted in mice that received 2 µg of Vasculotide P.O., there were no significant levels of Vasculotide detectable in the plasma of these mice.

Vasculotide Decreases the Proliferation and/or Differentiation of CFU-G

Figure 2:
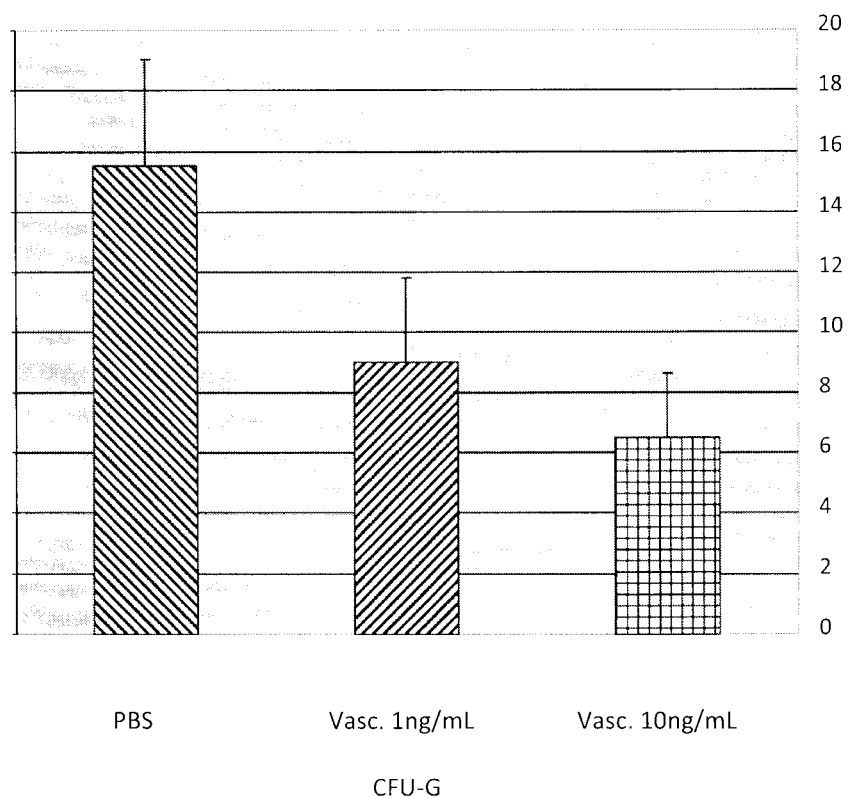
FIG. 2 shows inhibition of cellular proliferation and/or differentiation by Vasculotide in vitro. Dissociated bone marrow from CD1 mice was cultured in Methocult M3434 media for 7 days. Hematopoietic colonies (CFU-G) were then counted. A dose dependent, statistically significant reduction in CFU-G numbers was noted in response to Vasculotide treatment.

Angiopoietin 1 has been shown to provide quiescence and pro-survival signals to stem cells of the bone marrow (Lee et al. (2008) J. Radiat. Res. (Tokyo) 49(3), 313-320, Kim et al. (2008) FEBS Lett. 582(23-24), 3509-3514, and Gomei et al. (2010) Exp. Hematol. 38(2), 82-89). Using an ex vivo model of bone marrow proliferation and differentiation (methocult), the influence of Vasculotide on bone marrow extracted from the femurs of normal CD1 mice was observed. Bone marrow was disaggregated and resuspended in methocult M3434 media plus Vasculotide (Vasc 1 ng/ml or 10 ng/ml) or control (PBS). Enumeration of colonies at the 7 day time point revealed a statistically significant, dose-dependent reduction in total CFU-G as determined by gross appearance in duplicate plates treated with Vasculotide (FIG. 2). All other populations of cells were statistically indistinguishable from PBS control plates.

Figure 3A:
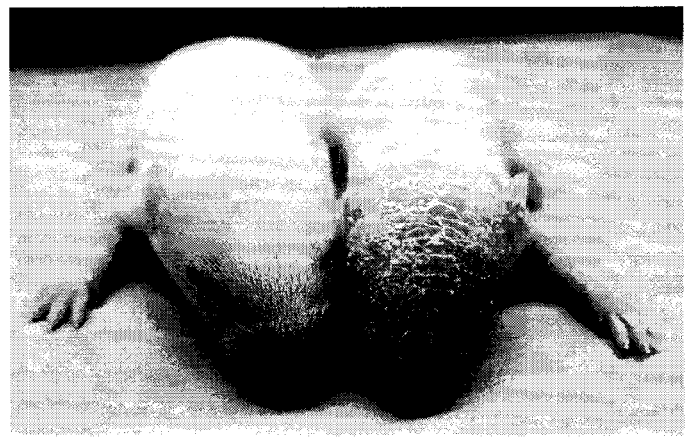
FIG. 3A shows gross phenotypic appearance of neonatal wild-type (left) and pTek-tTA:pTetOS-Tek Atopic dermatitis (AT Derm) mice (right). Note the scaly skin, delayed fur growth and slightly reduced size of the transgenic mouse compared to wild-type littermate.
Figure 3B:
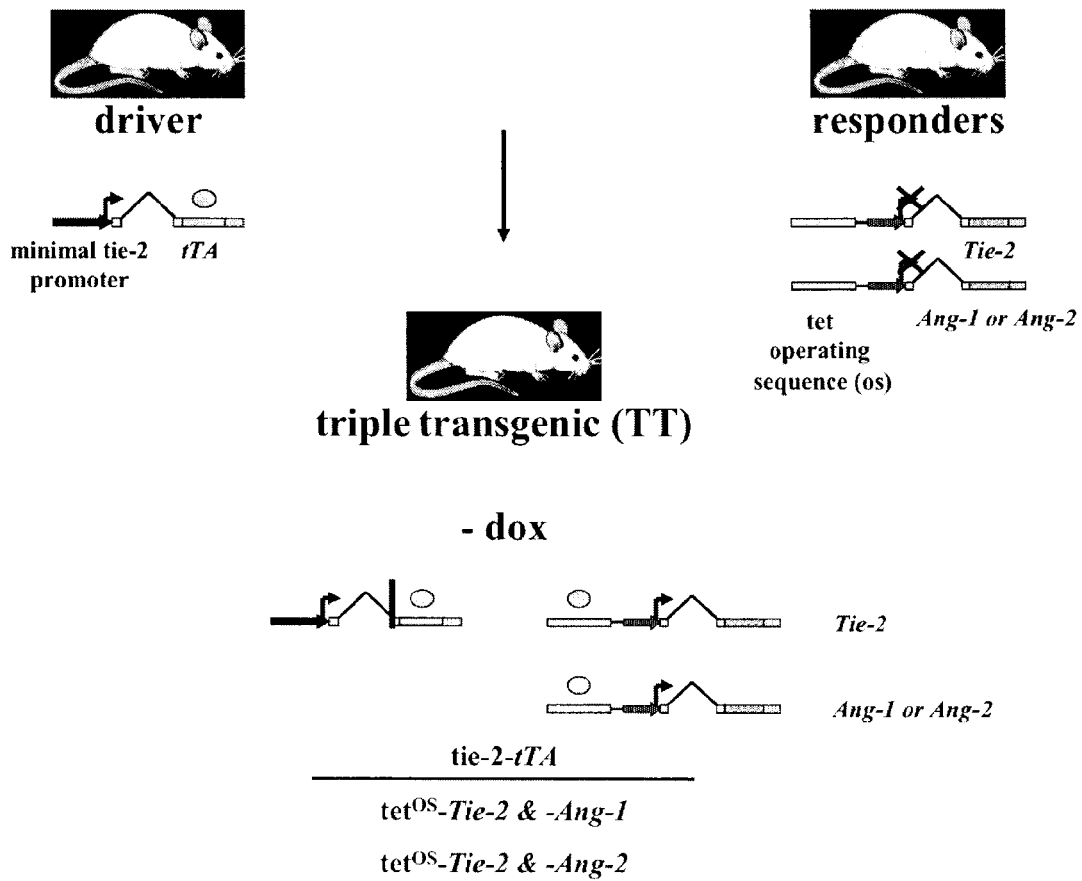
FIG. 3B is a schematic of transgenic mouse breeding approaches. Schema of the four transgenes used in these studies to produce the driver line (top left, minimal Tie2 promoter—tTa) and the responder lines (top right, tetOS-Tie2, tetOS-Ang1, and tetOS-Ang2) are indicated. Mice express the responder transgene only when double transgenic for the driver and responder or triple transgenic for the driver and two responder genes (lower schema). Expression of the responder genes can be silenced through addition of doxycycline to the drinking water.

Ang1, Ang2 and Vasculotide Modulate an Inflammatory Skin Disease Resembling Human Atopic Dermatitis/Psoriasis-Gross Phenotypic Observations The present inventors have previously shown that enforced overexpression of the Tie2 receptor in the vasculature results in an inflammatory skin phenotype in mice (FIG. 3A) that is consistent with many hallmarks of human atopic dermatitis/psoriasis (Voskas et al. (2005) Am. J. Pathol. 166(3), 843-855, Voskas et al. (2009) J. Leukoc. Biol. 84(1), 59-67). Importantly, an improvement in this phenotype was observed following treatment with classic anti-psoriasis interventions such as cyclosporine A and targeted ablation of T-cells (Voskas et al. (2005) Am. J. Pathol. 166(3), 843-855, Voskas et al. (2009) J. Leukoc. Biol. 84(1), 59-67) suggesting that this transgenic model shares many common elements with the human condition. Using common mouse transgenic approaches, a system was devised in which the impact of enforced expression of Ang1 or Ang2 could be assessed in this mouse model of inflammatory skin disease. This is the first such system where the implications of Ang1 or Ang2 expression can be simultaneously addressed in a single pathological state. A schematic of the genetic crosses is provided in FIG. 3B. Atopic dermatitis (AT derm) mice (pTek-tTA: pTetOS-Tek) engineered to overexpress Ang1 (pTetOS-Ang1) in the vasculature displayed a dramatic amelioration of disease. This was marked by a gross reduction in snout, conjunctiva, ear and paw erythema (FIGS. 3C-E). Additionally, there was a marked reduction in micro-haemorrhages of the ears, and a loss of scaly plaque on the tail (FIGS. 3C-E). Histologically, the triple transgenic Ang1 mice displayed a resolution of epidermal hyperplasia and a reduction in dermal leukocyte infiltration.

Figure 4:
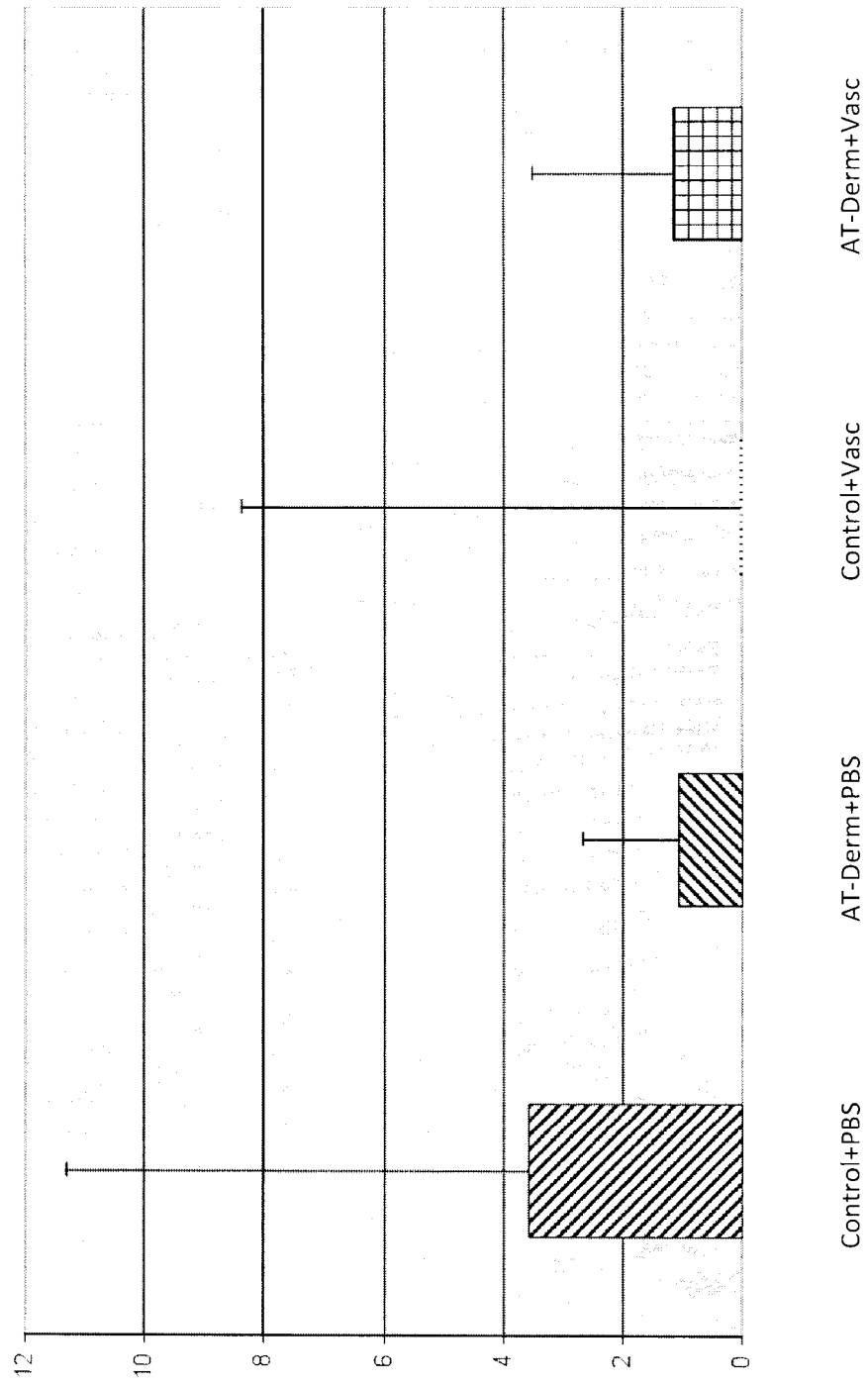
FIG. 4 shows the effects of Vasculotide treatment on mouse body weight. Following a 30-day treatment with Vasculotide, body weight was shown to be comparable to control mice. Mice were weighed at day zero and day 30 of the study. Percent change in body weight during 30-day treatment is shown. There was no statistically detectable alteration in body weight of mice receiving Vasculotide (40 μg/kg every 3 days) compared to vehicle treated mice.

In contrast to the effects of Ang1 overexpression in the AT derm mice, Ang2 overexpression exacerbated all of the noted phenotypic hallmarks (FIGS. 3C-E). The results of the Ang1 and Ang2 triple transgenic AT derm mouse studies served an important role in evaluating the therapeutic properties of Vasculotide in modulating Tie2 activity. Double transgenic AT derm mice (pTek-tTA:pTetOS-Tek), and their single transgenic or wild-type littermates were given Vasculotide (40 µg/kg) or PBS every three days for the period of 30 days. Mice were weighed prior to the study and at the end of the study to track potential toxicity issues that may result in weight loss or a delay in weight gain. Results showed no statistically significant alteration in the weight of mice treated with Vasculotide or vehicle control (PBS) (FIG. 4).

After the third dose of Vasculotide (9 days), a reduction in erythema was noted in the AT derm mice by two independent observers while no overt effects were noted in the single transgenic or wild-type litter mates receiving Vasculotide. Upon completion of the 30 day trial, mice were photographed to capture gross phenotypic changes. AT derm mice that had received Vasculotide displayed complete or almost complete resolution of erythema, micro-haemorrhages of the ears, and scaly plaque formation on the tail (FIGS. 5D, F). The degree of resolution of the phenotype post-treatment did not seem to correspond to the severity of the phenotype upon initiation (FIG. 5D shows the effects of Vasculotide on the AT-Derm: moderate phenotype while FIG. 5F shows the effects of Vasculotide on the AT-Derm: severe phenotype).

Figure 6:
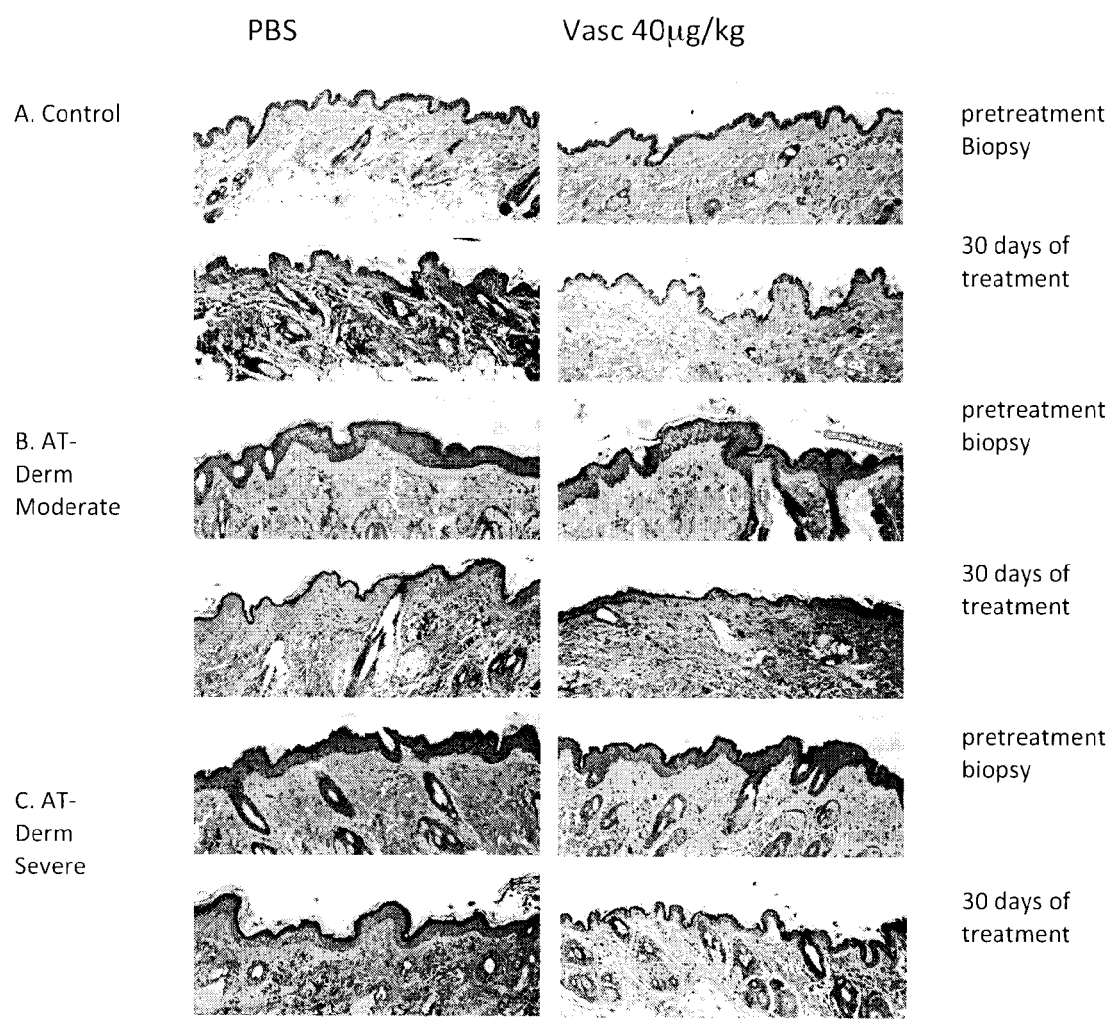
FIG. 6 shows the effects of Vasculotide treatment on epidermal hyperplasia and immune cell infiltrate in a murine model of atopic dermatitis. Vasculotide treatment was shown to resolve atopic dermatitis-related epidermal hyperplasia and to reduce immune cell infiltrate in the dermis. Skin tissue samples were obtained both before (pre-treatment biopsy) and following treatment (30 days treatment) from wild-type (Control, A), moderate phenotype (AT-Derm: Moderate, B) and severe phenotype (AT-Derm: Severe, C) mice treated with either PBS (PBS) or Vasculotide (Vasc 40 mg/kg). Tissues were subjected to hematoxylin and eosin staining, revealing a marked reduction in both epidermal hyperplasia and immune cell infiltrate in treated tissues. Stained pretreatment biopsies illustrate the severity of the phenotype. Corresponding post-treatment samples were obtained from the same mouse and are shown for consistency.

Histological and Immunohistological Examination of Vasculotide-Treated AT Derm Mice Skin biopsies were taken from all mice prior to initiation of the study and at the end of the study to track epidermal and dermal changes in response to Vasculotide. AT derm mice treated with Vasculotide displayed a dramatic reduction in epidermal hyperplasia and infiltration of leukocytes as revealed by H&E staining of tissues (FIG. 6; compare PBS treated to Vasc treated). Thin sections of skin tissue were H&E stained both prior to and following treatment with one of PBS or Vasculotide. Staining revealed a marked reduction in both epidermal hyperplasia and immune cell infiltrate in tissues treated with Vasculotide.

Figure 7A:
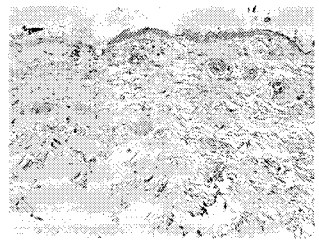
FIG. 7 shows the effect of Vasculotide on the expression of E-selectin, a pro-inflammatory endothelial cell adhesion protein, in the skin and underlying muscle layers. Immunohistochemistry was performed on tissues taken from wild-type (Control) and atopic dermatitis (AT-Derm: Severe) mice and revealed a profound upregulation of E-selectin (C,G) compared to wild-type controls (A,E). AT-Derm: Severe mice treated with Vasculotide at a dose of 40 µg/kg every 3 days for 30 days (D,H) showed a dramatic reduction in E-selectin expression. E-selectin expression in AT-Derm: Severe mice treated with Vasculotide (D,H) was indistinguishable from expression in wild-type animals treated with Vasculotide (B,F) or PBS (A,E).
Figure 7B:
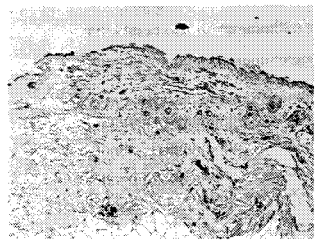
Figure 7C:
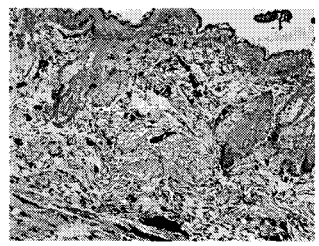
Figure 7D:
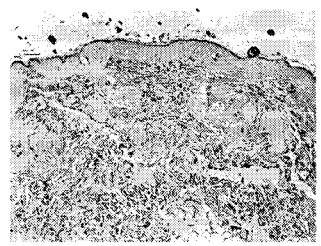
Figure 7E:
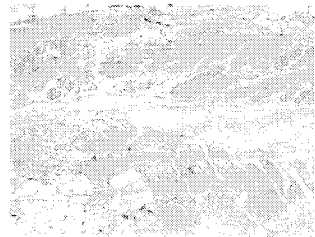
Figure 7F:
Figure 7G:
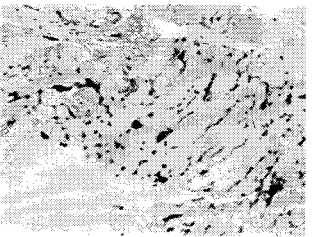
Figure 7H:
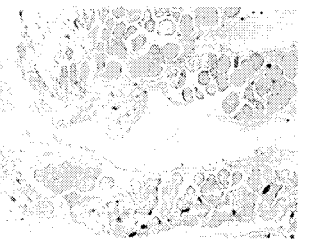
Figure 8A:
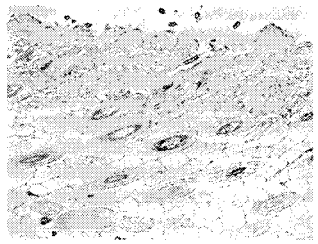
FIG. 8 shows the effect of Vasculotide on the expression of ICAM1, a pro-inflammatory endothelial cell adhesion protein, in the skin and underlying muscle layers. Similar to results obtained for E-selectin, ICAM1 expression was upregulated in AT-Derm: Severe animals (C,G) compared to wild-type mice (A,E). Treatment of the AT-Derm: Severe mice with Vasculotide at a dose of 40 µg/kg every 3 days for 30 days (D,H) showed a dramatic reduction in ICAM1 expression. ICAM1 expression in AT-Derm: Severe mice treated with Vasculotide (D,H) was indistinguishable from expression in wild-type animals treated with Vasculotide (B,F) or PBS (A,E).
Figure 8B:
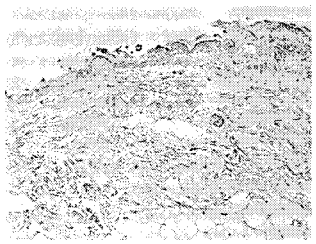
Figure 8C:
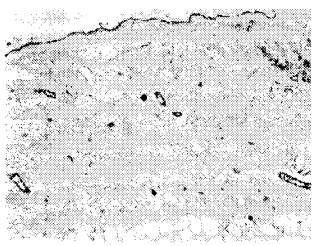
Figure 8D:
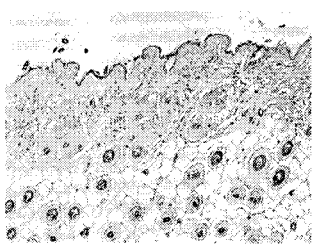
Figure 8E:
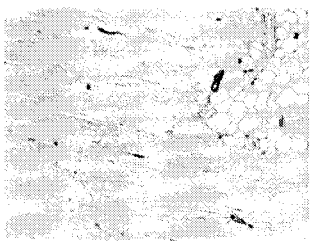
Figure 8F:
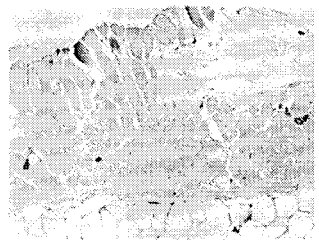
Figure 8G:
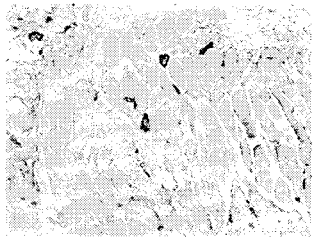
Figure 8H:
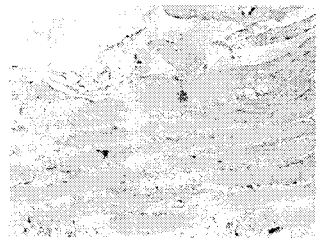
Figure 9A:
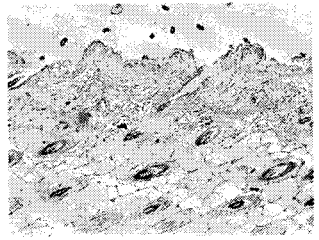
FIG. 9 shows the effect of Vasculotide on the expression of VCAM1, a pro-inflammatory endothelial cell adhesion protein, in the skin and underlying muscle layers. Similar to results obtained for E-selectin and ICAM1, VCAM1 expression was upregulated in AT-Derm: Severe animals (C,G) compared to wild-type mice (A,E). Treatment of the AT-Derm: Severe mice with Vasculotide at a dose of 40 µg/kg every 3 days for 30 days (D,H) showed a dramatic reduction in VCAM1 expression. VCAM1 expression in AT-Derm: Severe mice treated with Vasculotide (D,H) was indistinguishable from expression in wild-type animals treated with Vasculotide (B,F) or PBS (A,E).
Figure 9B:
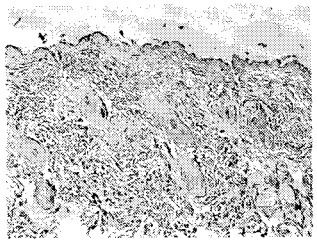
Figure 9C:
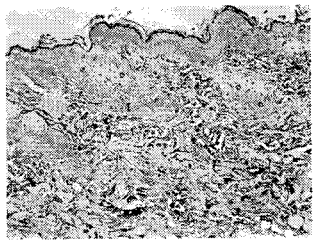
Figure 9D:
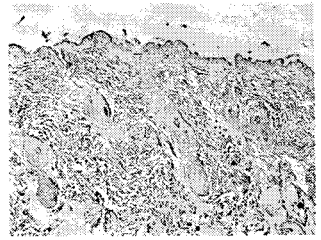
Figure 9E:
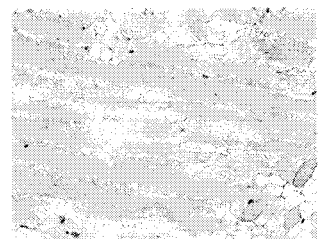
Figure 9F:
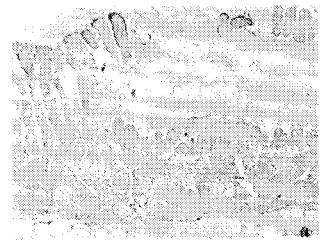
Figure 9G:
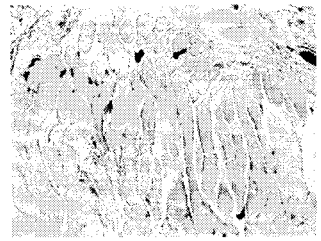
Figure 9H:
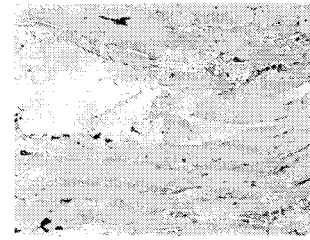

It has been suggested that the mechanism for generation of tissue eosinophilia is via upregulation of VCAM-1 (Bochner et al. (1995) J. Immunol. 154, 799-803, Adamko et al. (2004) Curr. Allergy Asthma Rep. 4, 149-158). Paraffin embedded thin sections were stained for markers of activated and/or inflamed endothelium including E-selectin (FIG. 7A-H), ICAM1 (FIG. 8A-H) and VCAM1 (FIG. 9A-H). Strikingly, AT derm mice displayed a high degree of positive staining for these markers (FIGS. 7C and G, FIGS. 8C and G, and FIGS. 9C and G) while those mice treated with Vasculotide display very low or absent levels of positive staining (FIGS. 7D and H, FIGS. 8D and H, and FIGS. 9D and H). These results suggest Vasculotide possesses robust anti-inflammatory properties on the vasculature of afflicted mice (FIGS. 7D, 8D and 9D). Examination of deeper tissue, the underlying skeletal muscle layer, demonstrated that the anti-inflammatory properties of Vasculotide identified in the skin are not restricted to the dermal layers (FIGS. 7H, 8H and 9H).

Figure 10:
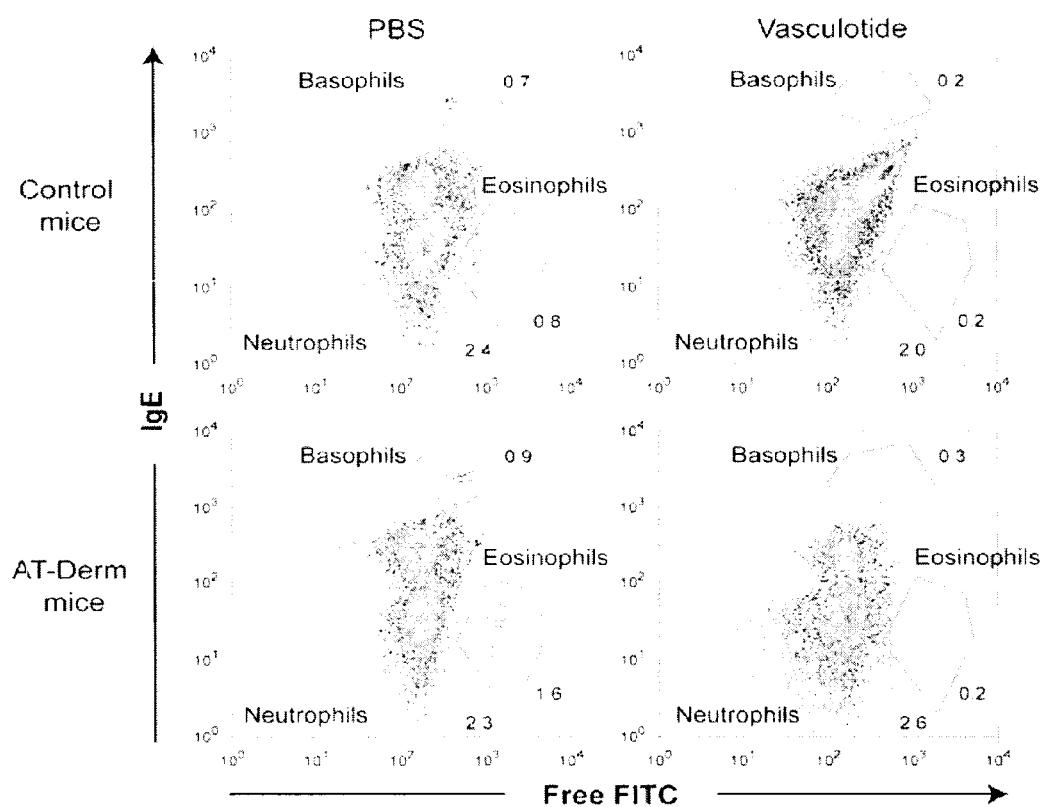
FIG. 10 shows the effects of Vasculotide treatment on the number of circulating eosinophils and basophils in wild-type (Control) and AT-Derm mice. Peripheral blood was drawn from normal CD-1 mice (Control) and atopic dermatitis mice (AT-Derm) treated with either vehicle (PBS) or Vasculotide for 30 days. Blood was processed for FACS analysis for surface IgE and FITC absorption. Decreased numbers of basophils and eosinophils were observed in Vasculotide treated control and AT-Derm mice compared to PBS-treated mice. No effects were observed with respect to neutrophils.

A central role for eosinophils has been identified in atopic conditions (Denburg and Keith (2008) Chest 134(5), 1037-1043, Hogan et al. (2008) Clin. Exp. Allergy 38(5), 709-750, Rothenberg and Hogan (2006) Ann. Rev. Immunol. 24, 147-174, Gauvreau et al. (2009) Clin. Exp. Allergy 39(9), 1297-1306). Previously, double transgenic AT derm mice were observed to present with grossly increased eosinophil numbers, both in the systemic circulation and as dermal infiltrates (Voskas et al. (2005) Am. J. Pathol. 166(3), 843-855, Voskas et al. (2008) J. Leukoc. Biol. 84(1), 59-67). In addition, morphological differences have been observed between circulating eosinophils and tissue-dwelling eosinophils (Malm-Erjefält et al. (2005) Clin. Exp. Allergy 35, 1334-1340). In response to an inflammatory stimulus, circulating blood eosinophils interact with endothelial cells initially then enter the tissue. Eosinophils must be activated by chemoattractant molecules such as chemokines prior to entry into tissue (Teixeira et al. (1995) Trends Pharmacol. Sci. 16, 418-423; Teixeira et al. (1997) Blood 89, 4566-4573). There are additional factors that control the accumulation of eosinophils in vivo, including their release from the bone marrow and circulation in blood (Teixeira et al. (1995) Trends Pharmacol. Sci. 16:418-423). Clinical trials have demonstrated differential effects of anti-IL5 antibody treatment on blood eosinophilia and tissue eosinophilia suggesting that distinct mechanisms control the relative number of these cells in specific compartments (Menzies-Gow et al. (2003) J. Allergy Clin. Immunol. 111, 714-719, Leckie et al. (2000) Lancet 356, 2144-2148, Flood-Page et al. (2003) Am. J. Respir. Crit. Care Med. 167, 199-204). Additional studies have suggested roles for IL-4 and IL-13 in the generation of blood eosinophilia and the entrance of eosinophils into tissue (Webb et al. (2000) J. Immunol. 165, 108-113, Bochner et al. (1995) J. Immunol. 154, 799-803, and Matsukura et al. (2001) Am. J. Respir. Cell Mol. Biol. 24, 755:761). These observations led to the examination of the potential for Vasculotide to improve the AT derm phenotype by reducing the level of circulating eosinophils. This would also be consistent with results shown in FIG. 2 in which a Vasculotide-dependent reduction in CFU-G was observed in CD1 bone marrow in an ex vivo methocult assay. After 30 days of treatment, blood, spleen, lymph nodes and bone marrow were collected from each mouse and a comprehensive FACS analysis was conducted to examine numbers of T cells (CD4/CD8), B cells, monocytes, stem cells, eosinophils, basophils, neutrophils, and macrophages. Of the cell populations examined, a marked reduction in basophil (FIG. 10) and eosinophil numbers were observed in the peripheral blood. Interestingly, noted reductions in both basophils and eosinophils occurred irrespective of disease state (AT derm vs. wild-type) suggesting that Vasculotide reduces the circulating numbers of these cells regardless of the inflammatory state. Of note, the number of granulocytes in the bone marrow of AT derm and wild-type mice, treated with Vasculotide or untreated, were unchanged. Without wishing to be bound by any one theory, this finding points to the potential that Vasculotide is modulating the differentiation, proliferation and/or the release of these cell populations from the bone marrow into the peripheral circulation. Consistent with this observation, the common CFU-G has been shown to express the defined target of Vasculotide, Tie2 (Gupta et al. (2006) Blood 107(5):1837-1846).

Figure 11B:
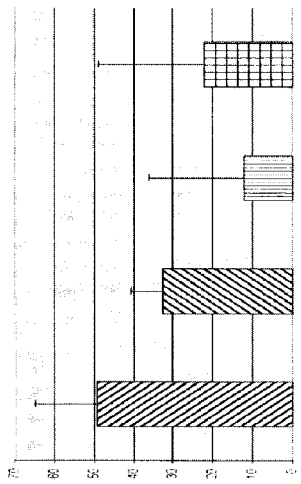
FIG. 11 shows the effects Vasculotide treatment on the circulating levels of a panel of cytokines and chemokines. Plasma was collected from all mice following 30 days of treatment with Vasculotide or PBS. Cytometric bead array (CBA) analysis was conducted on twelve analytes: IL-17 (A), MIG (B), IL12/IL23 (p40) (C), IL-9 (D), MIP-1a (E), MIP-1b (F), RANTES (G), TNF-α (H), IL-1β (I), IL-5 (J), IL-13 (K), and MCP-1 (L). Statistically significant results (unpaired student t-test were p=<0.05) are indicated on each graph.
Figure 11D:
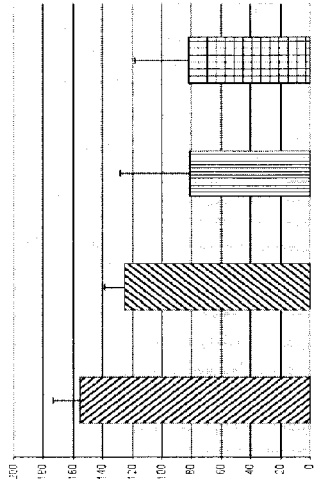
Figure 11A:
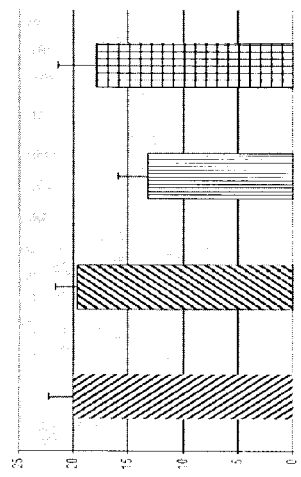
Figure 11C:
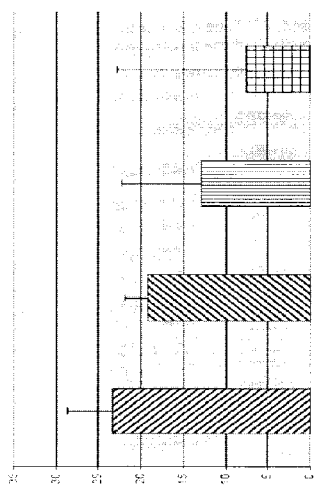
Figure 11E:
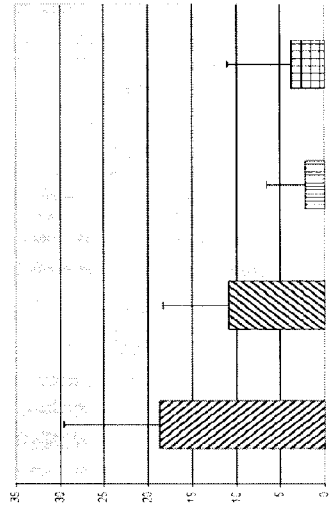
Figure 11F:
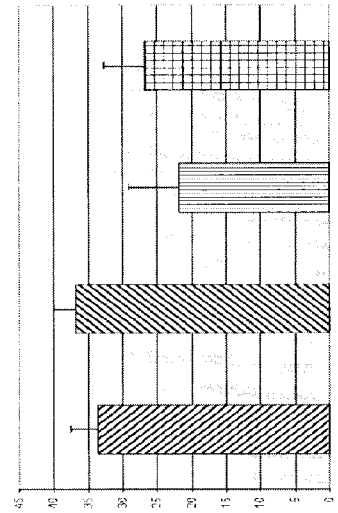
Figure 11G:
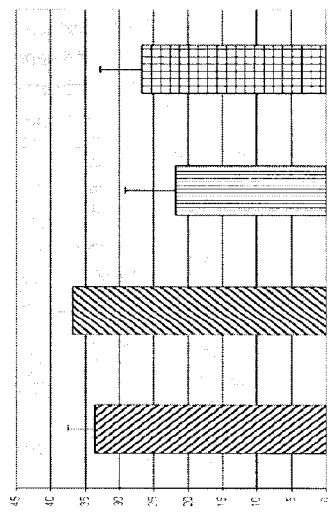
Figure 11H:
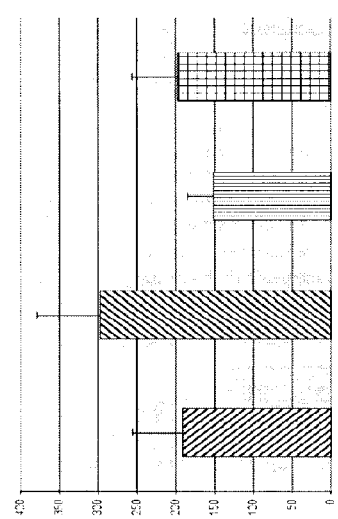
Figure 11J:
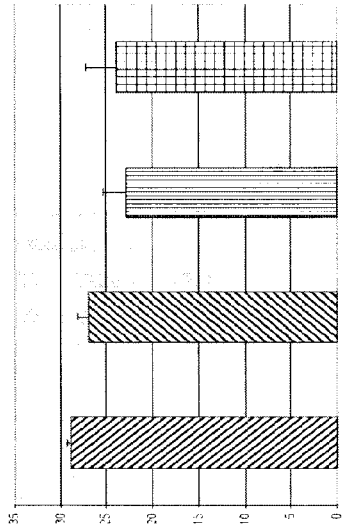
Figure 11L:
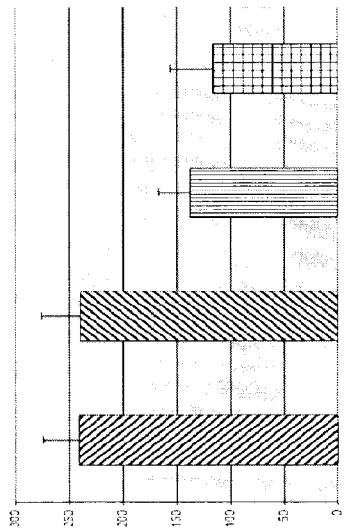
Figure 11I:
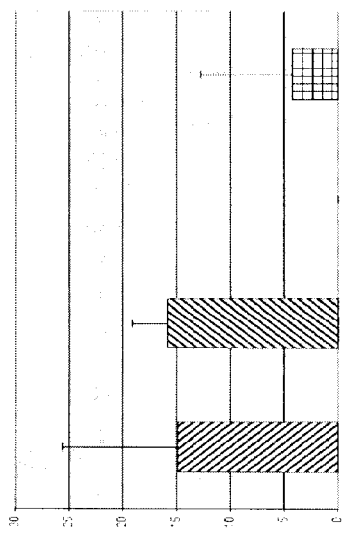
Figure 11K:
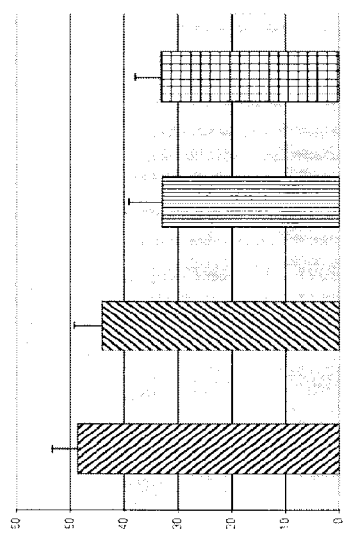

Cytokine/Chemokine Analysis of Vasculotide-Treated AT Derm and Wild-Type Littermates Blood taken from all animals at the completion of the study was used to examine the levels of various pro-inflammatory cytokines/chemokines. Clarified plasma was analysed via cytometric bead array (BD Bioscience) for 12 different cytokines/chemokines. Results are shown in FIG. 11. In wild-type (or single transgenic) mice, a statistically significant decrease in the following analytes were observed post-Vasculotide treatment: IL-17, p=0.0492 (FIG. 11A); MIG, p=0.0117 (FIG. 11B); IL-12/IL-23 p40, p=0.0494, (FIG. 11C); IL-9, p=0.0079 (FIG. 11D); MIP1a, p=0.0473 (FIG. 11E); MIP1b, p=0.003 (FIG. 11F); TNF-α, p=0.0309 (FIG. 11H); IL-5, p=0.0027 (FIG. 11J); IL-13, p=0.0027 (FIG. 11K); MCP1, p=0.0116 (FIG. 11L). Reductions were also observed in wild-type (or single transgenic) compared to AT Derm mice treated with PBS for the following: IL-9, p=0.0227 (FIG. 11D) and MIP1b, p=0.0144 (FIG. 11F). AT derm mice treated with Vasculotide displayed a reduction in IL-1β, p=0.0492 (FIG. 11I) when compared to PBS-treated AT derm mice.

Figure 12:
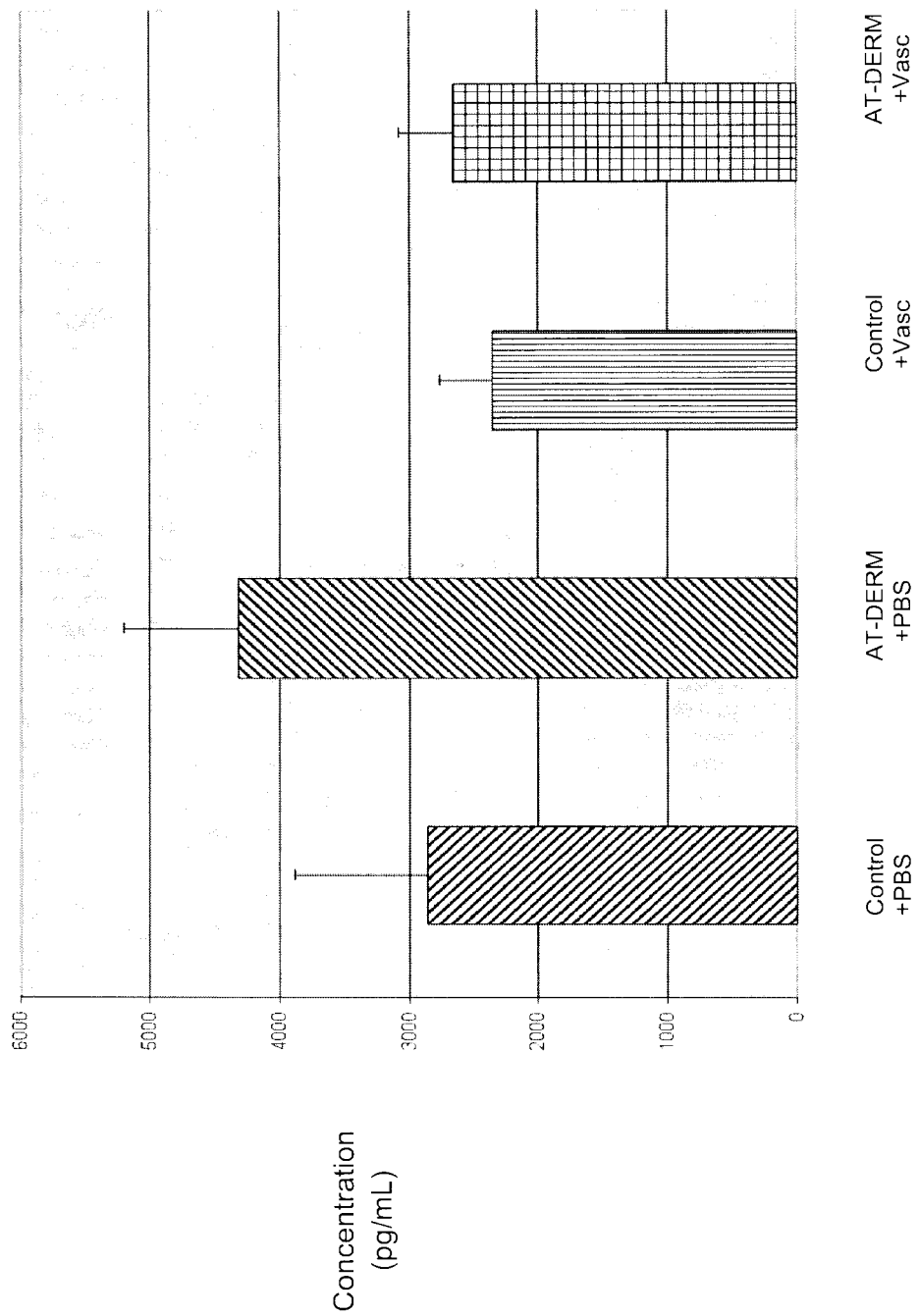
FIG. 12 shows the effects of Vasculotide treatment on eotaxin levels in wild-type (Control) and AT-Derm mice determined by ELISA. AT-Derm mice treated with Vasculotide showed a statistically significant decrease in eotaxin levels compared to PBS treated AT-Derm mice (p=0.0208, unpaired student t-test).

Vasculotide Reduces the Level of Circulating Eotaxin in Wild Type and at Derm Mice All mouse plasma was analysed for eotaxin 1-3 levels by way of ELISA (R&D Biosystems, Minneapolis, Minn. USA). PBS-treated mice in the AT Derm group had non-statistically elevated eotaxin levels when compared to normal control mice treated with PBS (FIG. 12). The cohort of AT Derm mice that were treated with Vasculotide showed a statistically significant (p=0.0208, unpaired student t-test) decrease compared to PBS treated AT Derm mice (FIG. 12).

Example 2

Effects of Vasculotide Treatment in Acute and Chronic Models Asthma

Figure 13A:
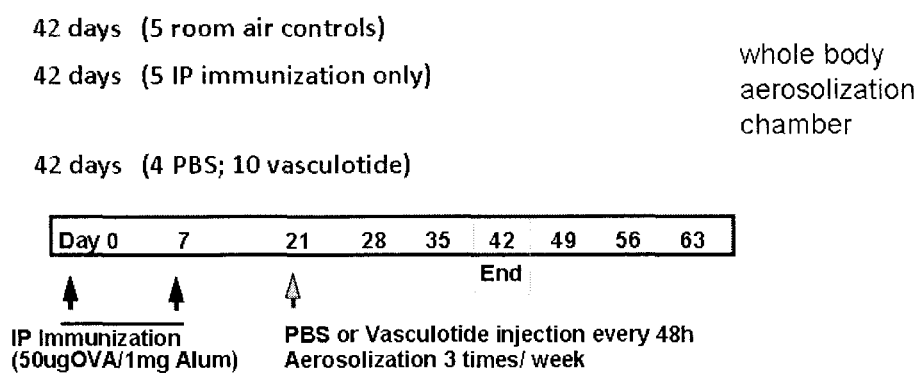
FIGS. 13A and 13B show schematics of treatment paradigms in a chronic allergen challenge model. Eight week old female Balb/c mice were sensitized to ovalbumin (Ova) by intraperitoneal (IP) systemic injection of Ova in the presence of aluminum hydroxide $(Al(OH)_3)$ (Alum). Post-sensitization, mice were challenged with Ova delivered in a full body aerosolization chamber three times a week starting on day 21. Vasculotide or saline vehicle (PBS) was delivered to the mice via IP injections every 2 days, starting at day 21. Room air control mice did not receive sensitization or aerosolization procedures, while the IP immunization group received 2 IP injections of Ova (day 0 and 7) in the presence of aluminum hydroxide $(Al(OH)_3)$ (Alum) with no subsequent aerosolization exposure to Ova.
Figure 13B:
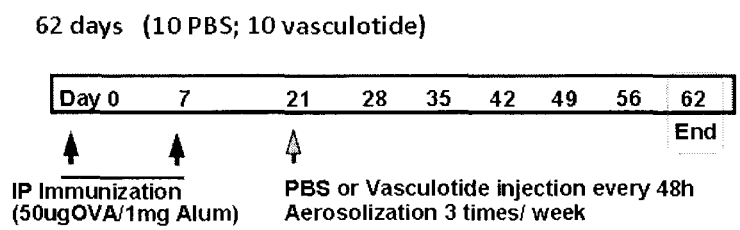

Material and Methods
Induction of Experimental Allergic Asthma:
(Chronic asthma model) Seven week old female Balb/c mice were injected intraperitoneally (IP) with 20 µg of chicken ovalbumin (OVA) absorbed with 1 mg aluminum hydroxide, an adjuvant known to promote the development of a Th2 response by the immune system, on day 0 (denoted by first day injection) and day 7. Full body inhaled exposure to OVA was initiated at day 21. Briefly, these treatments utilized an InExpose full body aerosol chamber (Scireq, Montreal, Canada) where a 1% OVA solution, suspended in PBS, pH 7.45, was nebulized at 0.2 mL/min with a filtered room air flow rate of 2400 mL/min for a total period of 30 minutes, 3 times a week for either 42 (FIG. 13A) or 62 days (FIG. 13B). (Acute asthma model) Seven week old female Balb/c mice were injected intraperitoneally with 50 µg of chicken OVA absorbed with 1 mg aluminum hydroxide on day 0 (denoted by first day injection) and day 7. Aqueous OVA (100 mg in PBS) was delivered intranasally daily from day 20 to day 24 (FIG. 2), Vasculotide or saline vehicle (control, PBS) was delivered to the mice via IP injections.

Blood Collection:
Blood was collected from the left ventricle of anaesthetized mice into heparinized 1 cc syringes. Following collection, blood was placed into Li-heparin microtubes. Subsequently, the tubes were centrifuged at 3000 RPM for 15 minutes at 4° C. Plasma was collected from the top of the samples and frozen at −80° C. for later analysis. The remaining buffy coat and red blood cells were lysed then fixed in 1× lyse/fix buffer (BD Biosciences, Mississauga, Canada) according to manufacturer's instructions.

Bronchial Alveolar Lavage:

Twenty-four hours after last aerosol exposure and immediately following exsanguinations, tissue was dissected from neck to expose trachea. A small lateral incision was made in the trachea to allow passage of 23 gauge lavage catheter into trachea. The catheter, attached to a 3 cc syringe containing warmed Hanks buffer, was carefully passed into the lumen of the trachea. A suture was secured around the trachea with a knot to secure the catheter in place. Buffer (1 cc) was injected slowly into the lungs and fully aspirated three times. The volume of recovered buffer was recorded for each animal to facilitate calculation of BAL infiltrate.

Cytometic Bead Array:

Analysis of plasma samples generated for the asthma study was the same as that outlined for the atopic dermatitis study with one small modification. Plasma from mice used in the asthma study was diluted 1:4 instead of 1:8 for the atopic dermatitis samples.

FACS Analysis of Leukocyte Populations:

(BAL analysis) Collected BAL fluid was centrifuged at 1000 RPM for 10 minutes at 4° C. BAL fluid was removed and collected for subsequent CBA analysis. The BAL cell pellet was lysed/fixed in 1× lyse/fix buffer according to manufacturer's instructions (BD Biosciences, Mississauga, Canada). The total number of cells contained in each sample was determined by flow cytometry using flow-set beads (Count Bright Beads, Invitrogen), to facilitate sample volume and cell count calculations. A total of 7000 beads were counted for each sample. Flow cytometry analysis was gated on FSC/SSC to eliminate debris and dead cells. Differential cell count analysis was also performed by FACS where surface marker antibodies were used as follows: eosinophils ($SSC^{hi}$ FITCmed $Ige^{med}$), neutrophils ($SSC^{med}$ $FITC^{hi}$ $Ige^{med}$), monocytes ($SSC^{med}$ $CD11b^+$ $CD115^+$) and lymphocytes ($SSC^{lo}$ and $CD4^+$ or $CD8^+$). In addition to monocyte markers ($SSC^{med}$ $CD11b^+$ $CD115^+$), these cell populations were further characterized using antibodies specific for Tie2, TLR4, and Ly6C. $Ly6C^{low}$ and $Ly6C^{high}$ further define monocytes as classical, resident monocytes or inflammatory monocytes, respectively. Identified neutrophils were further labelled with antibodies to Tie2 and TLR4. All cell suspensions were incubated with purified anti-CD16/CD32 mAb (BD Biosciences, Mississauga, ON, Canada) to block non-specific background caused by Fc receptors, followed by incubation with the specific antibodies. Cells were incubated at 4° C. for 30 min with optimal dilution of antibodies experimentally determined previously. Data acquisition was performed using a FACS LSR11 flow cytometer (BD Biosciences, Mississauga, ON, Canada), and analysis was performed using FlowJo software (Tree Star, Inc., Ashland, Oreg.).

(Peripheral Blood Analysis)

Peripheral blood was prepared for FACS analysis by lysing then fixing in 1× lyse/fix buffer according to manufacturer's instructions (BD Biosciences, Mississauga, Canada). The total number of mononuclear cells was obtained by FACS in the same manner as was the case for BAL enumeration.

Quantification of Fibrosis:

Lungs were fixed in 4% paraformaldehyde for 16 hours and then transferred to 70% ethanol. Thin sections (5 µm) were cut from paraffin-embedded tissue according to standard laboratory practice. Slides were stained with Masson's trichrome and were examined by light microscopy (Leica DM LB2 compound microscope). A total of 5 random fields of view for each sample (n=8-10) were photographed. Blinded quantification of blue collagen fibers was performed using NIH ImageJ software and a specific Masson's trichrome macro. Data was reported according to the percent blue positive staining area for a given microscopic field of view.

Results

Figure 14:
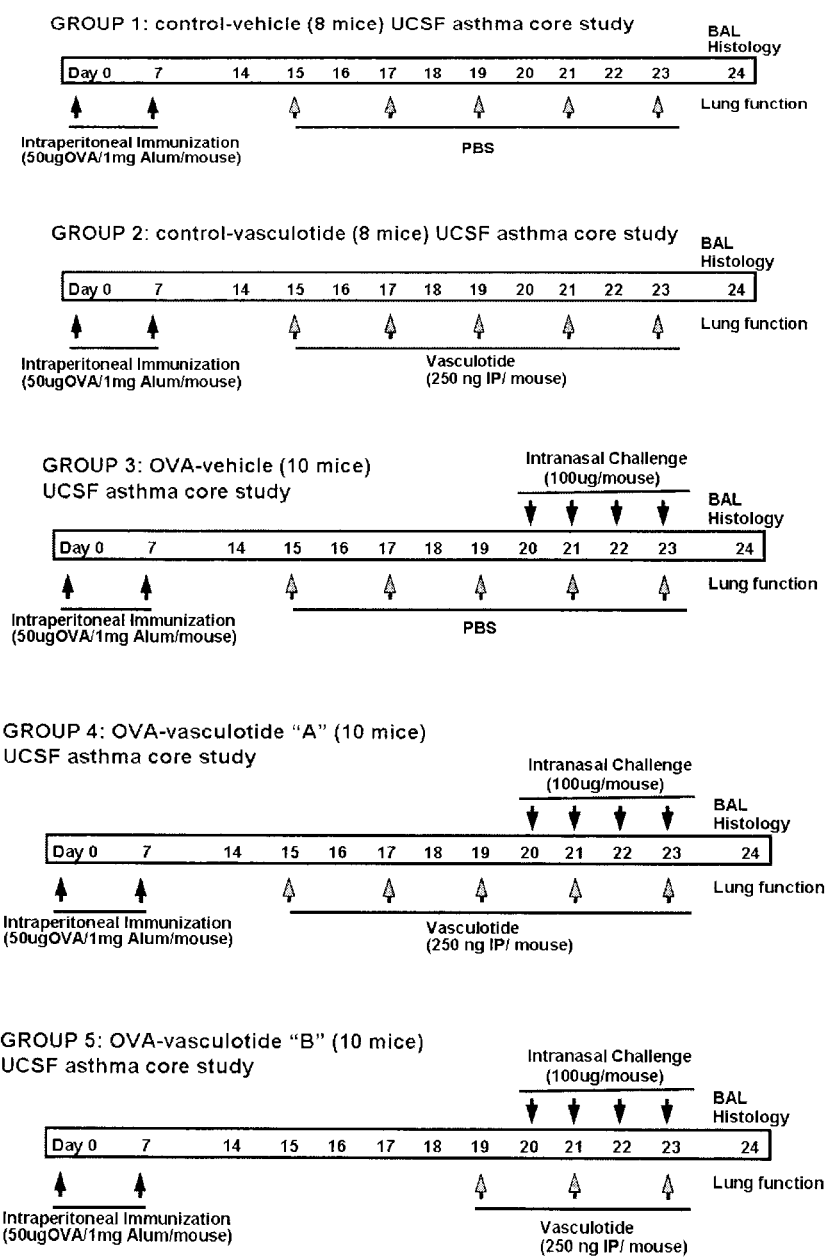
FIG. 14 shows schematics of treatment paradigms in acute allergen challenge models. Post-sensitization (days 0 and 7) mice were challenged intranasally with one of either PBS (vehicle control, groups 1 and 2, no asthma) or PBS-Ova solution every day from day 20 to day 24 (groups 3, 4, 5). Two separate regimens of Vasculotide or PBS administration via IP injections were followed: 1) five injections, starting on Day 15 and repeated every second day up to day 24 (groups 3 and 4); and 2) the same sequence as in 1) but initiated on day 19 for a total of 3 treatments (group 5).

Several mouse models have been developed that recapitulate specific clinically relevant features of asthma. Acute and chronic allergen challenge models have been extensively used to investigate key questions relating to the pathogenesis of asthma and potential approaches to novel therapies. To compare and contrast the results from these different models, female Balb/c mice challenged with Ova, an allergen known to induce a robust pulmonary allergic reaction in mice, were used in both acute and chronic experimental paradigms (FIGS. 13 and 14).

Outcome—Acute Asthma Model:

The acute allergen challenge model reproduced many key features of clinical asthma by inducing an extremely quick and robust allergic response in female Balb/c mice challenged with Ova intranasally. This response is characterized by high serum IgE levels, pulmonary airway inflammation marked by infiltration of immune cells, goblet cell hyperplasia, changes in cytokine production, airway epithelial cell hypertrophy, and airway hyperresponsiveness (AHR) to specific stimuli.

Outcome—Chronic Asthma Model:

The chronic allergen challenge models used, which involved nebulization of Ova following initial sensitization, reproduced similar features of clinical asthma including a Th2-dependent allergic inflammatory response characterized by increased eosinophils in the pulmonary airway mucosa, and evidence of more permanent changes in the lung tissue commonly referred to as "tissue remodeling". For these experiments, female Balb/c mice were challenged with nebulized Ova at day 42 or day 62. This model is thought to better recapitulate and follow the development of these long-term remodeling effects on tissues.

Impact of Vasculotide

Figure 15:
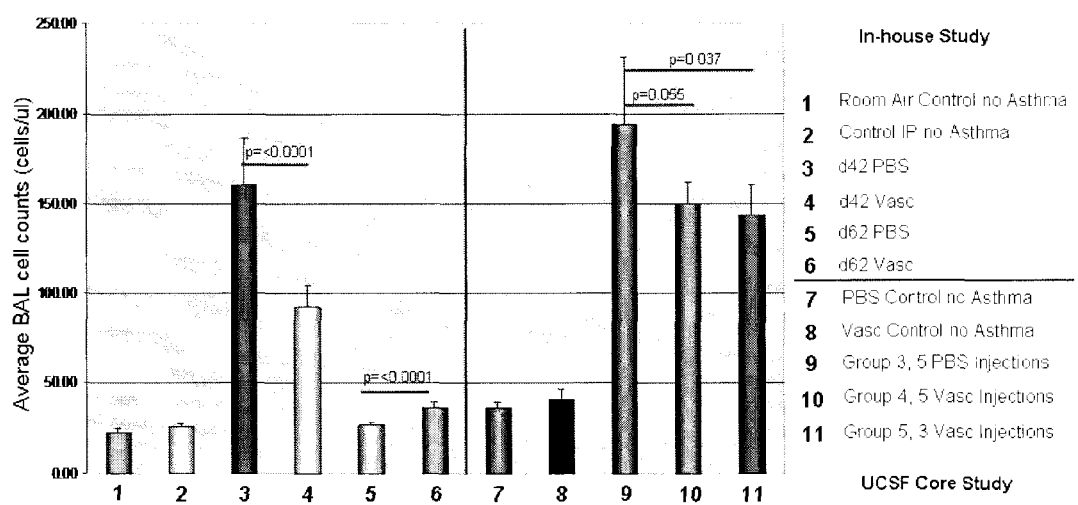
FIG. 15 shows reduction in lung inflammation in asthmatic mice treated with Vasculotide. The total number of cells present in the bronchial alveolar lavage (BAL) of mice was enumerated by flow cytometry using flow-set beads to allow sample volume calculation. Flow cytometry analysis was gated on FSC/SSC to eliminate debris and dead cells. The concentration of cells (cells/ml) was then calculated from the number of microsphere events (7000/sample) counted compared to cell events.

To evaluate the effect of Vasculotide in the setting of established pulmonary inflammation, chronic asthma models lasting 42 and 62 days were performed. Additionally, the inflammatory status of acute asthma models (24 days) treated with Vasculotide was compared and contrasted with those noted for the chronic asthma studies. The effects of Vasculotide administration on several key features of clinical asthma, including airway and systemic inflammation and production of inflammatory mediators, were measured. A detailed analysis, by flow cytometry, of the cellular content of bronchoalveolar lavage (BAL) collected from both acute and chronic asthmatic mice was performed. For each sample, a precise absolute mononuclear cell count was obtained by adding counting beads during flow cytometry analysis. In acute and day 42 (d42) chronic asthma experiments, both intranasal and nebulized. Ova challenges caused a significant increase in BAL cellularity compared to non-asthmatic animal controls (FIG. 15). In contrast, day 62 (d62) chronic asthma mice had low BAL cellularity, reflecting established chronic asthma characterized by low airway inflammation (FIG. 15). Systemic treatment of asthmatic mice with Vasculotide significantly reduced total absolute BAL counts by 25% in acute asthma experiments, and by 45% in the d42 chronic asthma model (FIG. 15). Importantly, Vasculotide treatment in the absence of asthma in mice had no effect on BAL cell numbers (FIG. 15).

Figure 16A:
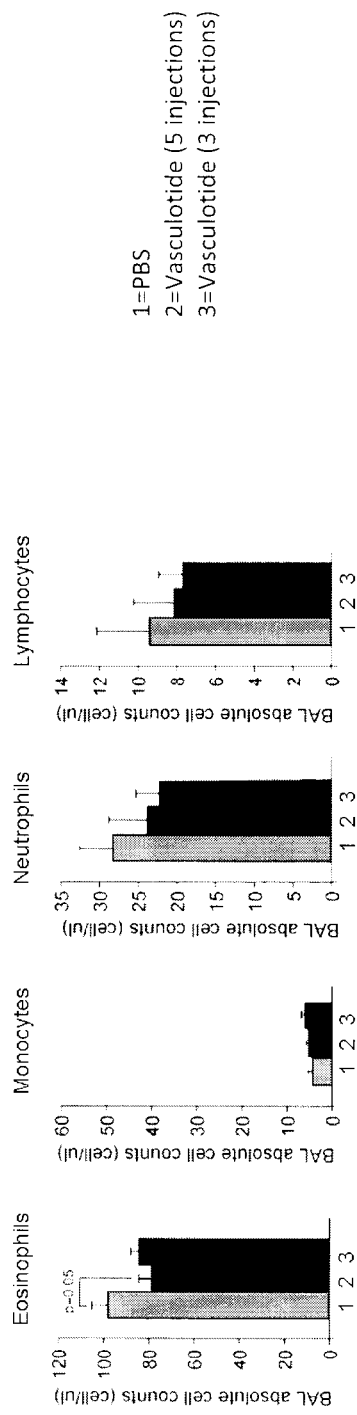
FIG. 16A shows a statistical reduction of eosinophils, with a non-statistical trend towards decreased lymphocytes and neutrophils in the BAL of asthmatic mice treated with Vasculotide in the acute setting (day 24). The differential cell count of the BAL was determined by flow cytometry and counting beads using surface markers to identify: eosinophils (SSChi FITCmed IgEmed), neutrophils (SSCmed FITChi IgEmed), monocytes (SSCmed CD11b+ CD115+) and lymphocytes (SSClo and CD4+ or CD8+). Statistical analysis was performed by way of unpaired students T-test. Differences were deemed significant when p<0.05. B) The same analysis was performed for BAL collected from the chronically asthmatic mice. Cell counts were performed on day 42 and day 62. A statistical reduction in monocytes, eosinophils and lymphocytes was noted in response to Vasculotide treatment. C) Analysis of neutrophil numbers revealed a very small increase in BAL numbers in d62 mice treated with Vsaculotide. PBS was used as a control in all experiments.
Figure 16B:
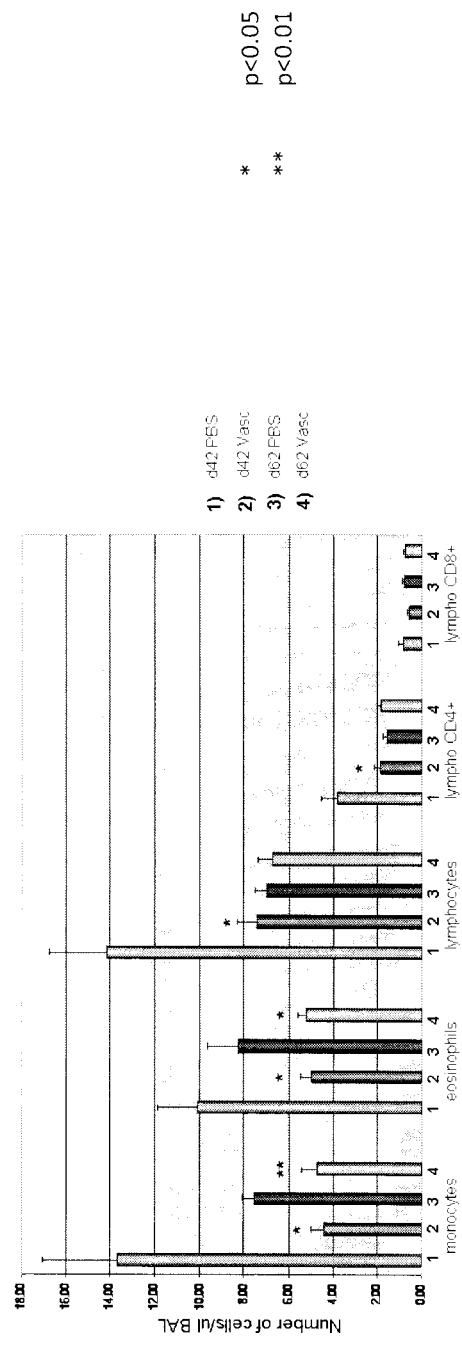
Figure 16C:
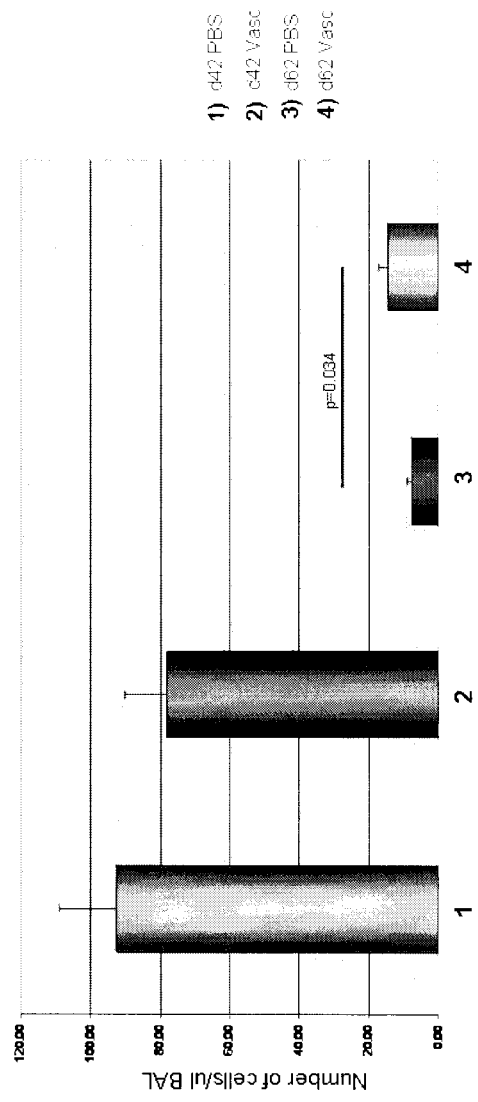
Figure 17:
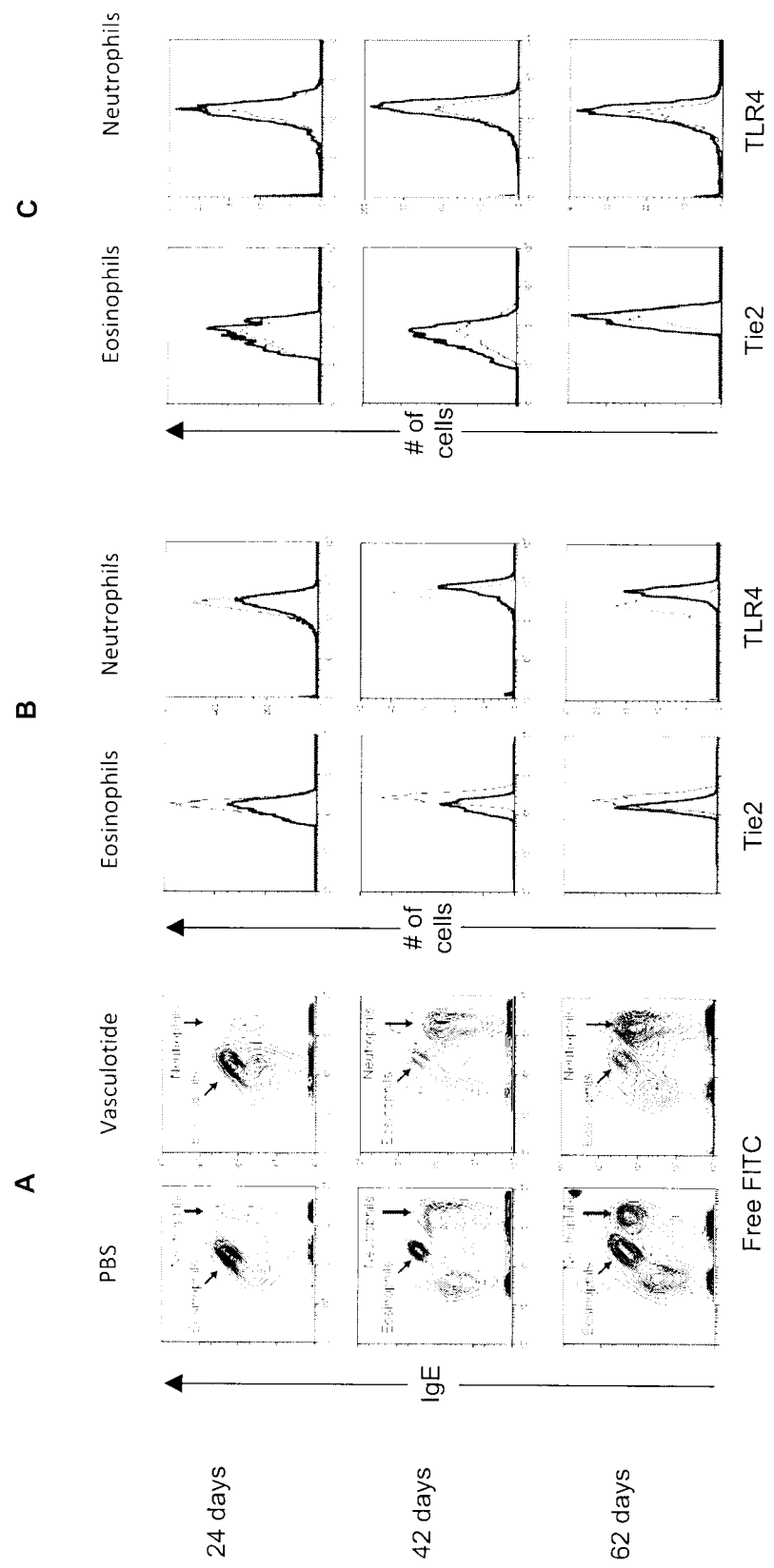
FIG. 17 shows reduction of the number of eosinophils in asthmatic mice treated with Vasculotide. BAL was drawn from acute asthma mice treated with PBS (data in histograms represented by thin line) or Vasculotide (data in histograms represented by thick line) at day 24 and from chronic asthma mice at day 42 or 62. A) Flow cytometry analysis showing the identification of eosinophils and neutrophils based on the differential binding of free FITC and expression of IgE at the cell surface. Flow cytometry histograms showing Tie2 expression at the surface of B) eosinophils (FITCmed IgEmed) and C) neutrophils (FITChi IgEmed). (Center and Right panel) Also indicated is TLR4 expression at the surface of Tie2 expressing eosinophils (FITCmed IgEmed) (B) and neutrophils (FITChi IgEmed) (C).
Figure 18:
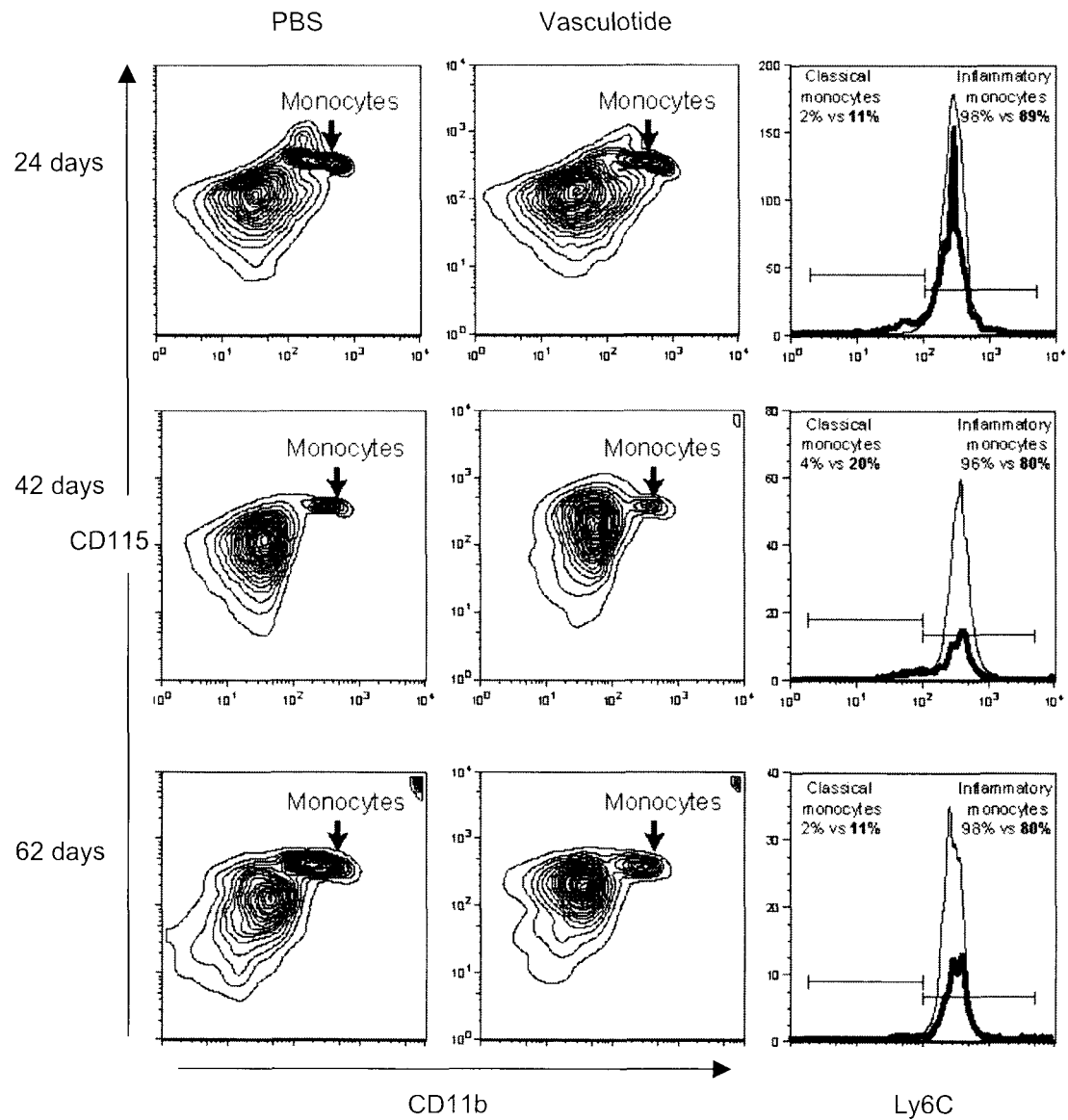
FIG. 18 shows reduction of the number of monocytes in asthmatic mice treated with Vasculotide. BAL was drawn from acute asthma mice treated with PBS (data in histograms represented by thin line) or Vasculotide (data in histograms represented by thick line) at day 24 (d24) and from chronic asthma mice at day 42 (d42) and 62 (d62). Flow cytometry analysis was used to identify monocytes based on the differential expression of CD11b (horizontal axis) and CD115 (vertical axis) at the cell surface. Two subpopulations of monocytes were further distinguished by the differential expression of Ly6C (right panel). Classical resident monocytes (CD11b+ CD115+ Ly6C−) and inflammatory monocytes (CD11b+ CD115+ Ly6C+) were present in the BAL of mice. Inflammatory monocytes were decreased and classical monocytes were increased in all groups that received Vasculotide.

Characterization of BAL cellular content by flow cytometry revealed that increased BAL counts in asthmatic mice were mostly due to infiltration of eosinophils ($SSC^{hi}$ $FITC^{med}$ $IgE^{med}$) or neutrophils ($SSC^{med}$ $FITC^{hi}$ $IgE^{med}$) (FIGS. 16 and 17), and to a lesser extent classical monocytes ($SSC^{med}$ $CD11b^+$ $CD115^+$ $Ly6C^-$) (FIG. 18), inflammatory monocytes ($SSC^{med}$ $CD11b^+$ $CD115^+$ $Ly6C^+$) (FIG. 18) and lymphocytes ($SSC^{lo}$ and $CD4^+$ or $CD8^+$) (FIG. 16B). Treatment of acutely asthmatic mice with Vasculotide only reduced BAL eosinophil absolute counts, and did not affect the number of neutrophils, monocytes, and lymphocytes (FIGS. 16A, 17 and 18). In chronic asthma experiments, Vasculotide significantly decreased BAL eosinophil numbers, as well as monocyte infiltration (FIGS. 16B-C, 17 and 18). At d42, the neutrophil count was unchanged, whereas a slight increase was seen at d62 (FIGS. 16C and 17C). Tie2 is expressed at the surface of eosinophils and neutrophils as shown by a range of mean fluorescence intensity (MFI) of 350-570 and 100-135, respectively (FIGS. 17B and C). The cell surface levels of Tie2 on eosinophils were decreased in d42 chronic asthma animals treated with Vasculotide (MFI 566 PBS vs 205 Vasculotide) (FIG. 17B). Tie2 levels were unchanged in neutrophils (FIG. 17C). Decreased Tie2 receptor expression coincides with a marked increase in Toll-like receptor 4 (TLR4) expression on eosinophils (MFI 166 PBS vs 758 Vasculotide) that is sustained under established chronic asthma conditions (d62 chronic asthma experiments; MFI 118 PBS vs 132 Vasculotide) (FIG. 17B). An increase in TLR4 expression has been associated with an anti-inflammatory response in the lung (Zhao et al. 2010). Treatment of asthmatic mice with Vasculotide also had an effect on monocytes isolated from BAL samples. Whereas the overall number of monocytes was unchanged, significantly fewer inflammatory monocytes ($Ly6C^+$) than classical resident monocytes ($Ly6C^-$) were found in the BAL of acute asthma animals compared to PBS asthmatic controls (FIGS. 16A and 18 (top panel; d24)). In chronic asthma experiments (d42 and d62), this trend was accentuated, with a decreased absolute number of monocytes in the BAL of animals treated with Vasculotide (FIGS. 16B and 18 (d42 and d62)).

Figure 19:
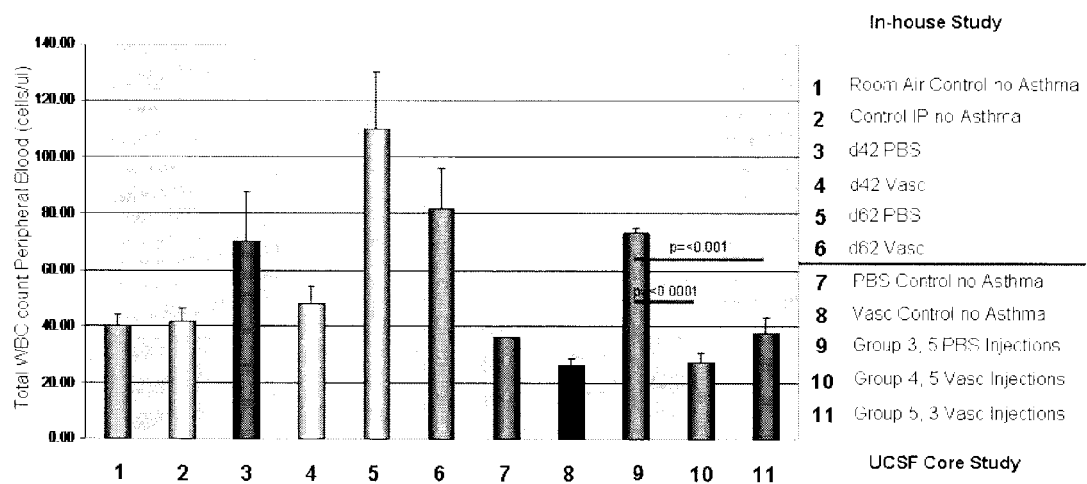
FIG. 19 shows reduction in the number of peripheral blood mononuclear cells (PBMNC) following Vasculotide treatment in murine asthma models. Peripheral blood was drawn from acute asthma mice treated with PBS or Vasculotide at d24 and from chronic asthma mice at d42 or d62. Red blood cells were lysed and mononuclear cells were fixed. The total number of mononuclear cells present in blood of mice was obtained by flow cytometry using flow-set beads to allow sample volume calculation. Flow cytometry analysis was gated on FSC/SSC to eliminate debris and dead cells and was stopped at 5000 beads. The concentration of cells (cells/ml) was then calculated using the number of events recorded. Statistical analysis was performed by way of unpaired student T-test. Differences were deemed significant when $p<0.05$.
Figure 20:
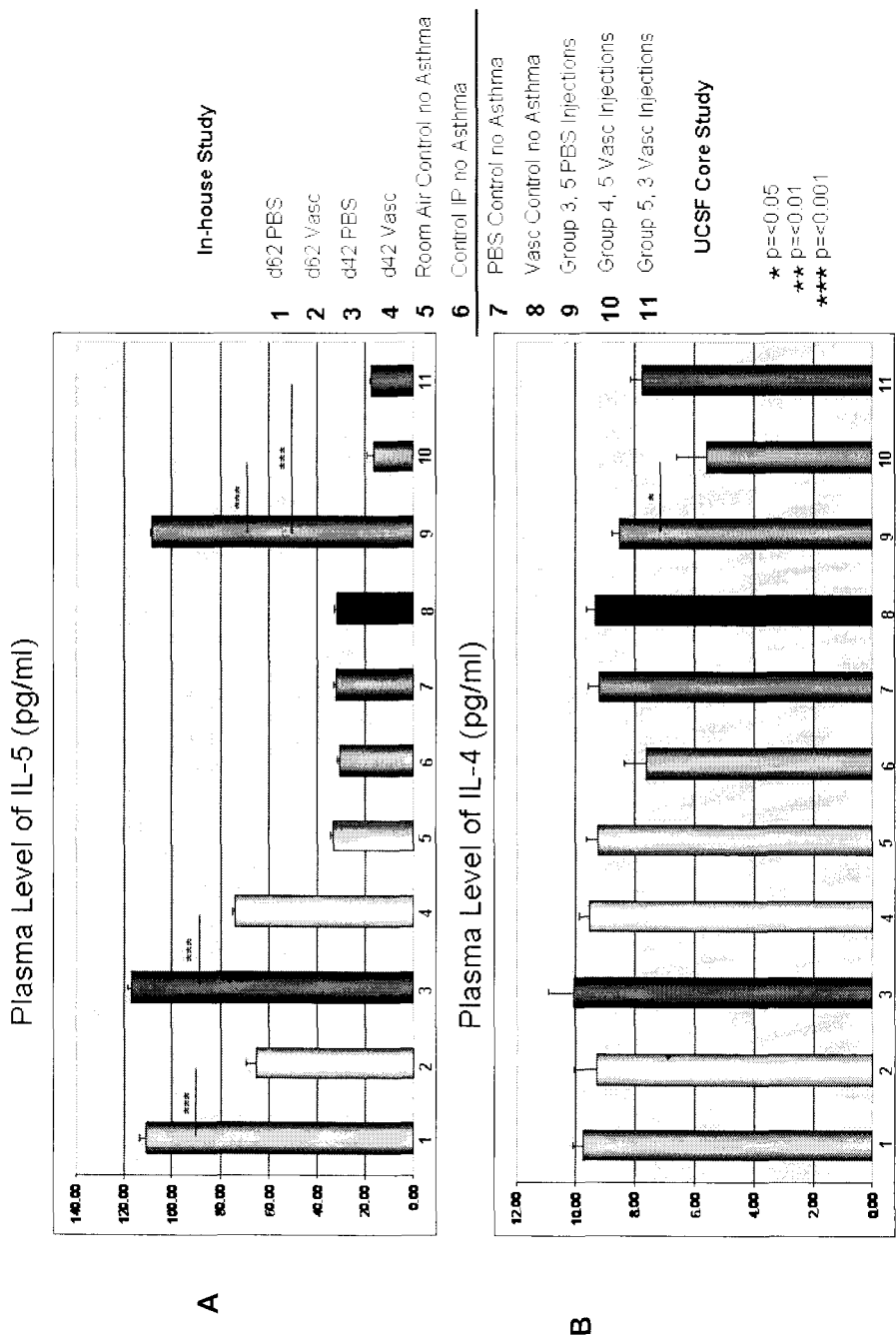
FIG. 20 shows decreases in inflammatory mediator plasma levels following Vasculotide treatment in murine models of asthma. A) IL-5 (pg/ml); B) IL-4 (pg/ml); C) MIP-1a; D) TNF-α; E) MIG; F) MIP-1b; G) RANTES; H) IL-9; I) IL-13; J) MCP-1; K) IL-17; and L) IL-1 β. Plasma was collected from non-asthmatic controls, acute asthma mice at d24 and from chronic asthma mice at d42 or d62. Animals were treated with PBS vehicle or Vasculotide. Cytometric bead array was used to simultaneously and quantitatively measure multiple cytokines/chemokines in a single sample. The exact quantity (μg/ml) of each cytokine/chemokine in plasma was obtained by including serial dilutions of a standard mixture of cytokine/chemokine protein with known concentration. $*p<0.05$ $p<0.01$, $*p<0.001$. ND=none detected.
Figure 20:
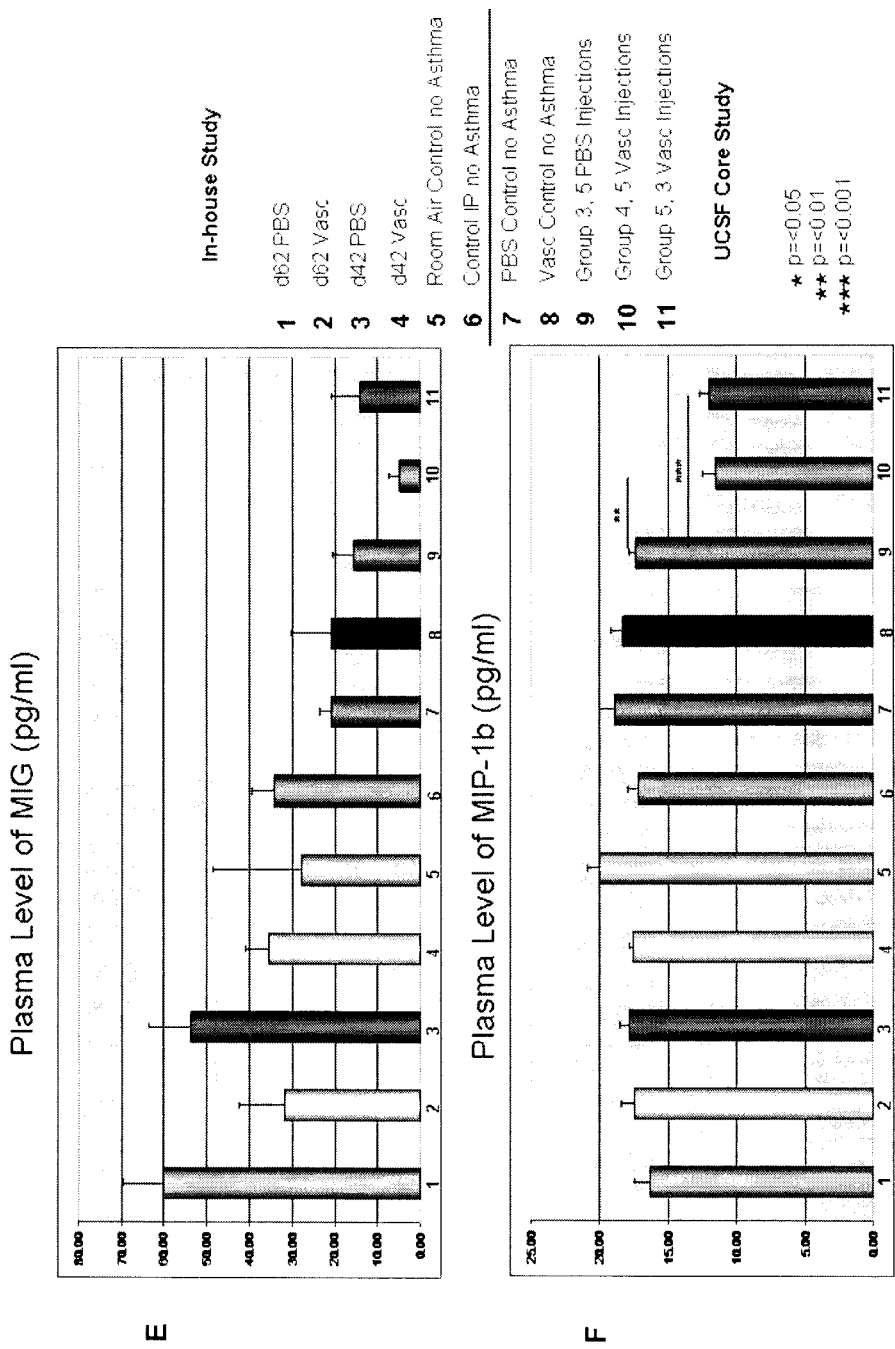
Figure 20:
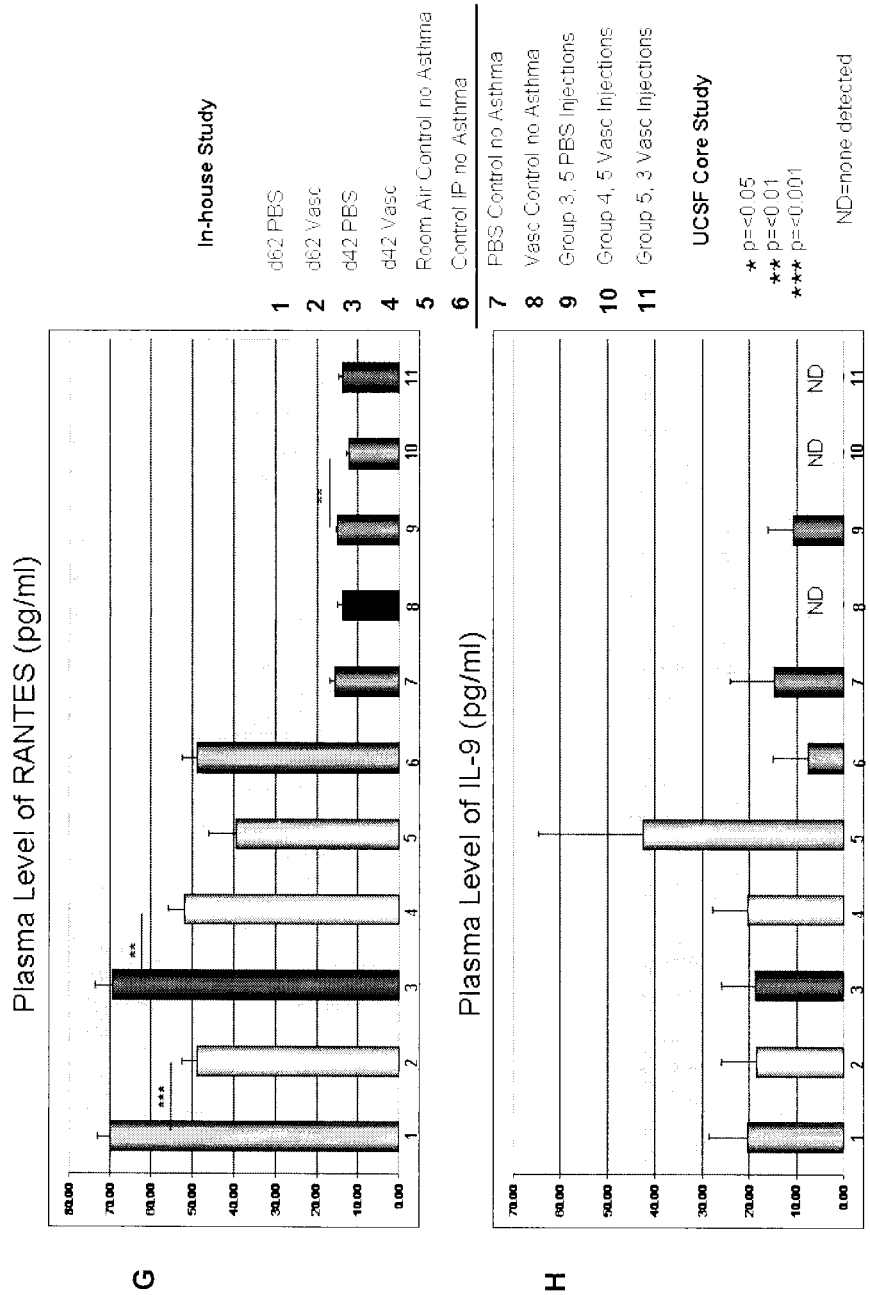
Figure 20:
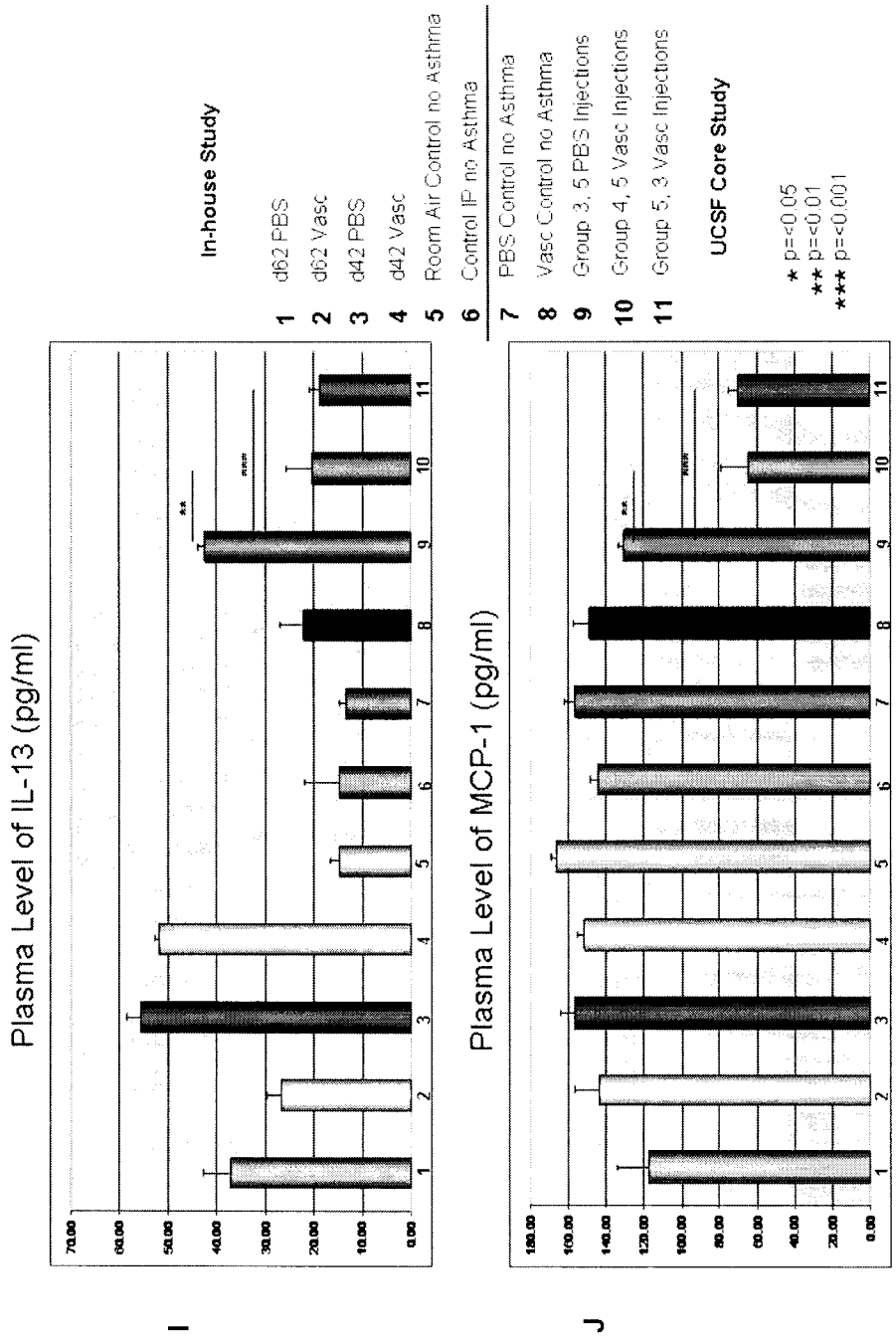
Figure 20:
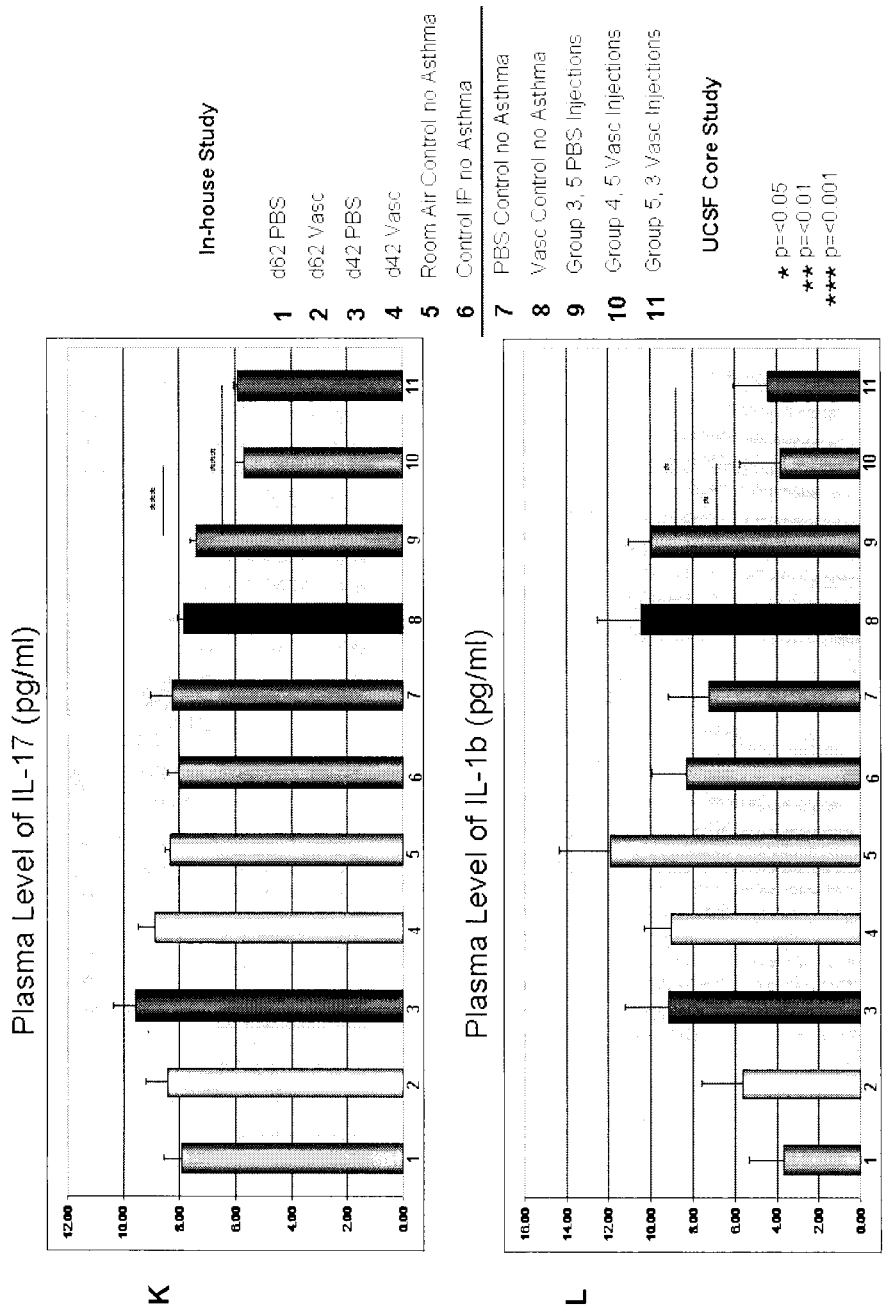

In both acute and chronic asthma models employed, systemic inflammation was associated with an increased number of inflammatory mononuclear cells in the peripheral blood of mice as determined by flow cytometry. Treatment of acute asthmatic mice with Vasculotide prevented a significant increase in the number of peripheral blood cells, maintaining values close to normal non-asthmatic levels (FIG. 19). In chronic asthmatic animals, although there was a clear trend toward a reduction in the absolute number of peripheral blood mononuclear cells, results did not reach significance (FIG. 19). To investigate the possible mechanisms associated with the decreased pulmonary and systemic inflammatory phenotypes observed upon treatment of asthmatic mice with Vasculotide, a cytometric bead array was used to measure plasma levels of 12 different cytokines and chemokines (FIG. 20). Many cytokines directly implicated in the pathogenesis of asthma were decreased in the serum of acute asthmatic mice treated with Vasculotide, including IL-5 (FIG. 20A), IL-4 (FIG. 20B), IL-13 (FIG. 20I), TNF (FIG. 20D), RANTES (FIG. 20O), MCP-1 (FIG. 20J), MIP1α (FIG. 20C), and MIP1β (FIG. 20F). Other cytokines evaluated were MIG (FIG. 20E), IL-9 (FIG. 20H), IL-17 (FIG. 20K), and IL-1β (FIG. 20L). Interestingly, in chronic asthma experiments, sustained effects of Vasculotide on decreasing IL-5, TNF and RANTES only were observed (FIG. 20). These cytokines and chemokines are known to influence eosinophils and other inflammatory cells in asthma (Kim et al. 2010).

Figure 21A:
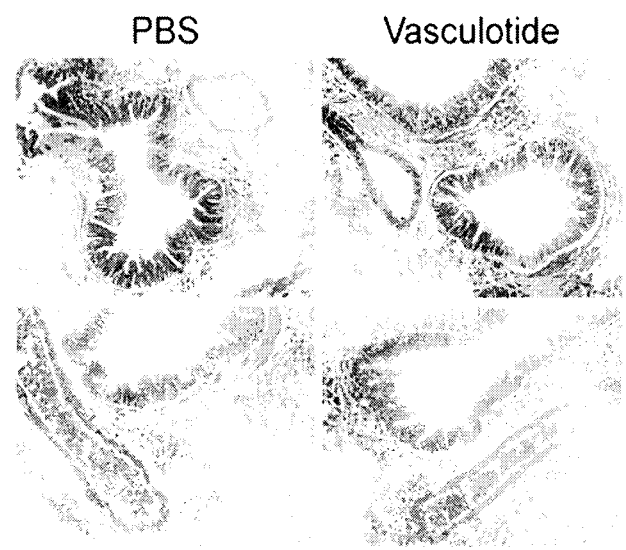
FIG. 21 shows decreased lung fibrosis in d62 chronic asthma mice following Vasculotide treatment. A) Lungs of chronic asthma mice (d62) treated with PBS or Vasculotide were prepared for histology and stained with Masson's Trichrome (n=8-10). Two different representative microscopic fields of view are shown for each of PBS or Vasculotide-treated lungs. Masson's Trichrome produces red keratin or muscle fibers, blue collagen, pink cytoplasm and black cell nuclei. Analysis of blue collagen fibers was performed on 5 separate images from each lung section and quantified using ImageJ software and a Masson's Trichrome macro. All analyses were performed by blinded observer. B) Quantification is presented in table format as the average % area positive blue staining in a given microscope field for each of PBS (control) and Vasculotide treatment.
Figure 21B:
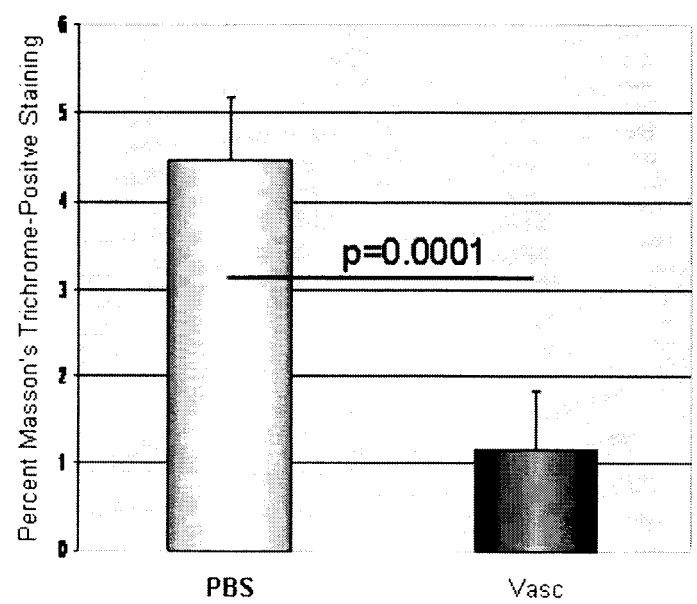

A feature of chronic asthma is lung tissue remodeling. Histological analysis of lung tissue sections taken from d62 chronic asthma animals and stained with Masson's trichrome revealed a considerable amount of collagen deposition in the peribronchiole and perivascular lung areas in PBS-treated asthmatic animals (FIG. 21A). In animals treated with Vasculotide, a marked decrease in collagen deposition was observed (FIG. 21A). The amount of collagen in lung sections was quantified using computer analysis. Results demonstrated a striking 4-fold decrease in collagen deposition, revealing a clear improvement in lung histology in asthmatic animals following treatment with Vasculotide (FIG. 21B).

Discussion

The molecular target for Vasculotide, Tie2, is expressed on key cell types that are thought to play pivotal role(s) in driving the remodeling response of the lung in the asthmatic patient, including: the vascular endothelium, eosinophils, neutrophils and monocytes. Pre-clinical and clinical studies have pointed towards a significant imbalance between Ang1 and its natural antagonist, Ang2, as an important pathophysiological mechanism underlying the development of asthma. An appropriate re-balancing of the Ang1/Tie2 signaling pathway via Vasculotide delivery was shown to have a dramatic impact on many hallmarks of asthma, including systemic inflammatory cytokine and chemokine levels, proliferation of mononuclear cells, and lung fibrosis.

Example 3

In Vitro Modulation of Eosinophil/Basophil Progenitors

Eosinophils/basophils (Eo/B) from mice and humans exhibit several common properties, but also behave somewhat different. Thus, Eo/B from mice and healthy donors are isolated. Eosinophils from the periphery or bone marrow are enriched by magnetic bead sorting using anti CD125 (IL-5Ra) conjugated to magnetic particles. These cells preparations are stimulated with either recombinant Ang1 or Vasculotide and different cellular parameters are measured, including cellular growth, apoptosis, migration and Tie2-specific cellular signaling.

To examine the effect of Vasculotide on Eo/B progenitors, bone marrow colony assays are performed. Human bone marrow preparations are purchased from Stem Cell Technologies (Vancouver, BC) and murine bone marrow are obtained by flushing femurs of normal mice. Non-adherent mononuclear cells are cultured in MethoCult supplemented with IL-5 to optimize for eosinophil/basophil colony formation (Eo/B-CFU). These cultures are treated with Vasculotide at differing concentrations and at different times post plating in MethoCult. The appearance of Eo/B-CFU is measured.

In Vivo Modulation Of Eosinophil/Basophil Progenitors

Eo/Bs and their progenitors are harvested from Vasculotide treated asthmatic animals from the periphery or bone marrow. In order to establish an Eo/B cellular profile treated and non-treated animals are harvested on week 1, 2, 4 and 6 and the number of Eo/Bs in the periphery, bone marrow and progenitors is determined. The number of peripheral and bone marrow eosinophils is determined by flow cytometry analysis using Ly6G, CD11b, IgE and free FITC markers. Eo/B progenitors in the bone marrow are measured by Eo/B-CFU assay.

Preliminary data suggests that Vasculotide impacts the Eo/B progenitors directly.

While the present disclosure has been described with reference to what are presently considered to be the examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

REFERENCES

Adamko D., Lacy P., and Moqbel R. Eosinophil function in allergic inflammation: from bone marrow to tissue response. Curr. Allergy Asthma Rep. 4, 149-158 (2004).

Barrett, N. A. & Austen, K. F. Innate cells and T helper 2 cell immunity in airway inflammation Immunity. 31, 425-437 (2009).

Bochner B. S., Klunk D. A., Sterbinsky S. A., Coffman R. L. and Schleimer R. P. IL-13 selectively induces vascular cell adhesion molecule-1 expression in human endothelial cells. J. Immunol. 154, 799-803 (1995).

Brkovic A, Pelletier M, Girard D, & Sirois M G. Angiopoietin chemotactic activities on neutrophils are regulated by PI-3K activation. J Leukoc Biol 81(4), 1093-1101 (2007).

Bureau W, Van Slyke P, Jones J, Han R N, Ward N L, Stewart D J, & Dumont D J. Chronic systemic delivery of angiopoietin-2 reveals a possible independent angiogenic effect. Am. J. Physiol. Heart Circ. Physiol. 291(2), H948-965 (2006).

Cho, C. H., Kammerer, R. A., Lee, H. J., Yasunaga, K., Kim, K. T., Choi, H. H., Kim, W., Kim, S. H., Park, S. K., Lee, G. M. & Koh, G. Y. Designed angiopoietin-1 variant, COMP-Ang1, protects against radiation-induced endothelial cell apoptosis. Proc. Natl. Acad. Sci. U.S.A 101, 5553-5558 (2004a).

Cho, C. H., Kammerer, R. A., Lee, N. J., Steinmetz, M. O., Ryu, Y. S., Lee, S. H., Yasunaga, K., Kim, K. T., Kim, I., Choi, H. H., Kim, W., Kim, S. H., Park, S. K., Lee, G. M. & Koh, G. Y. COMP-Ang1: a designed angiopoietin-1 variant with nonleaky angiogenic activity. Proc. Natl. Acad. Sci. U.S.A 101, 5547-5552 (2004b).

Denburg, J. A. & Keith, P. K. Eosinophil progenitors in airway diseases: clinical implications. Chest 134, 1037-1043 (2008).

Eichenfield, L. F., Hanifin, J. M., Beck, L. A., Lemanske, R. F., Jr., Sampson, H. A., Weiss, S. T. & Leung, D. Y. Atopic dermatitis and asthma: parallels in the evolution of treatment. Pediatrics. 111, 608-616 (2003).

Flood-Page P. T., Menzies-Gow A. N., Kay A. B. and Robinson D. S. Eosinophil's role remains uncertain as anti-interleukin-5 only partially depletes numbers in asthmatic airway. Am. J. Respir. Crit. Care Med. 167, 199-204 (2003).

Gauvreau, G. M., Ellis, A. K. & Denburg, J. A. Haemopoietic processes in allergic disease: eosinophil/basophil development. Clin. Exp. Allergy 39, 1297-1306 (2009).

Gomei Y, Nakamura Y., Yoshihara H, Hosokawa K, Iwasaki H, Suda T, & Arai F. Functional differences between two Tie2 ligands, angiopoietin-1 and -2, in regulation of adult bone marrow hematopoietic stem cells. Exp Hematol 38(2), 82-89 (2010).

Gruber B. L. Marchese M. J, & Kew R. Angiogenic factors stimulate mast-cell migration. Blood 86(7), 2488-2493 (1995).

Gupta R, Karpatkin S, & Basch R S. Hematopoiesis and stem cell renewal in long-term bone marrow cultures containing catalase. Blood 107(5), 1837-1846 (2006).

Hogan, S. P. Recent advances in eosinophil biology. Int. Arch. Allergy Immunol. 143 Suppl 1, 3-14 (2007).

Hogan S. P., Rosenberg H. F., Moqbel R., Phipps S., Foster P. S., Lacy P., Kay A. B., and Rothenberg M. E. Eosinophils: biological properties and role in health and disease. Clin Exp Allergy. 38(5), 709-750 (2008).

Huse W. D., Sastry L., Iverson S. A., Kang A. S., Alting-Mees M., Burton D. R., Benkovic S. J., and Lerner R. A. Generation of a large combinatorial library of the immunoglobulin repertoire in phage lambda. Science 246:4935, 1275-1282 (1989).

Jacobsen E. A., Taranova A. G., Lee N. A. & Lee J. J. Eosinophils: singularly destructive effector cells or purveyors of immunoregulation? J. Allergy Clin. Immunol. 119, 1313-1320 (2007).

Kaufman R. J., Murtha P., Davies M. V. Translational efficiency of polycistronic mRNAs and their utilization to express heterologous genes in mammalian cells. EMBO J. 6:187-195 (1987).

Kim H, Choi J. Y, Lee J. M, Park Y. S, Suh H, Song H. R, Jo S. A, & Jo I. Dexamethasone increases angiopoietin-1 and quiescent hematopoietic stem cells: a novel mechanism of dexamethasone-induced hematoprotection. FEBS Lett 582 (23-24), 3509-3514 (2008).

Kim, H. Y., DeKruyff, R. H. & Umetsu, D. T. The many paths to asthma: phenotype shaped by innate and adaptive immunity. Nat. Immunol. 11, 577-584 (2010).

Kohler G. and Milstein C. Continuous cultures of fused cells secreting antibody of predefined specificity. Nature 256, 495-497 (1975).

Kozbor and Roder (1983) Immunology Today 4:3, 72-79

Leckie M. J., ten Brinke A., Khan J., Diamant Z., O'Connor B. J., Walls C. M., Mathur A. K., Cowley H. C., Chung K. F., Djukanovic R., Hansel T. T., Holgate S. T., Sterk P. J., and Barnes P. J. Effects of an interleukin-5 blocking monoclonal antibody on eosinophils, airway hyper-responsiveness, and the late asthmatic response. Lancet. 356(9248), 2144-8 (2000).

Lee H. J, Bae S. W, Koh G. Y, & Lee Y. S. COMP-Ang1, angiopoietin-1 variant protects radiation-induced bone marrow damage in C57BL/6 mice. J Radiat Res (Tokyo) 49(3), 313-320 (2008).

Maliba R, Brkovic A, Neagoe P. E, Villeneuve L. R, & Sirois M. G. Angiopoietin-mediated endothelial P-selectin translocation: cell signaling mechanisms. J Leukoc Biol 83(2), 352-360 (2008).

Malm-Erjefält M., Greiff L., Ankerst J., Andersson M., Wallengrana J., Cardell L.-O., Rak S., Persson C. G. A. and Erjefält J S. Circulating eosinophils in asthma, allergic rhinitis, and atopic dermatitis lack morphological signs of degranulation. Clin. Exp. Allergy 35, 1334-1340 (2005).

Matsukura S., Stellato C., Georas S. N., Casolaro V., Plitt J. R., Miura K., Kurosawa S., Schindler U., and Schleimer R. P. Interleukin-13 upregulates eotaxin expression in airway epithelial cells by a STATE-dependent mechanism. Am J Respir Cell Mol. Biol. 24(6), 755-61 (2001).

McCafferty J., Griffiths A. D., Winter G., and Chiswell D. J. Phage antibodies: filamentous phage displaying antibody variable domains. Nature 348, 552-555 (1989).

Menzies-Gow A., Flood-Page P., Sehmi R., Burman J., Hamid Q., Robinson D. S., Kay A. B., and Denburg J. Anti-IL-5 (mepolizumab) therapy induces bone marrow eosinophil maturational arrest and decreases eosinophil progenitors in the bronchial mucosa of atopic asthmatics. J Allergy Clin Immunol. 111(4), 714-9 (2003).

Morgan et al. *Ann. Reports Med. Chem.* 24, 243-252 (1989).

Morrison S. L., Johnson M. J., Herzenberg L. A., Oi V. T. Chimeric human antibody molecules: mouse antigen-binding domains with human constant region domains. Proc. Natl. Acad. Sci. 81:21, 6851-6855 (1984).

Murdoch C, Tazzyman S, Webster S, & Lewis C. E. Expression of Tie-2 by human monocytes and their responses to angiopoietin-2. J Immunol 178(11):7405-7411 (2007).

Nielsen P E, Egholm M, Berg R H, Buchardt O, Sequence-selective recognition of DNA by strand displacement with a thymine-substituted polyamide. Science 254(5037), 1497-500 (1991).

Olsson L. and Kaplan H. S. Human—human monoclonal antibody-producing hybridomas: technical aspects. Methods in Enzymol. 92, 3-16 (1983).

Procopio, W. N., Pelavin, P. I., Lee, W. M. & Yielding, N. M. Angiopoietin-1 and -2 coiled coil domains mediate distinct homo-oligomerization patterns, but fibrinogen-like domains mediate ligand activity. J. Biol. Chem. 274, 30196-30201 (1999).

Raap, U. & Wardlaw, A. J. A new paradigm of eosinophil granulocytes: neuroimmune interactions. Exp. Dermatol. 17, 731-738 (2008).

Rothenberg, M. E. & Hogan, S. P. The eosinophil. Annu. Rev. Immunol. 24, 147-174 (2006).

Rothenberg, M. E. Eosinophils: biological properties and role in health and disease. Clin. Exp. Allergy 38, 709-750 (2008).

Schroeder, J. T. Basophils beyond effector cells of allergic inflammation. Adv. Immunol. 101, 123-61, (2009).

Seed, B. An LFA-3 cDNA encodes a phospholipid-linked membrane protein homologous to its receptor CD2. Nature 329(6142), 840-2 (1987).

Simon R. J., Kania R. S., Zuckermann R. N., Huebner V. D., Jewell D. A., Banville S., Ng S, Wang L., Rosenberg S., Marlowe C. K. Peptoids: a modular approach to drug discovery. Proc. Natl. Acad. Sci. 89, 9367-9371 (1992).

Sturn D. H, Feistritzer C., Mosheimer B, A., Djanani A., Bijuklic K., Patsch J, R, & Wiedermann C. J. Angiopoietin affects neutrophil migration. Microcirculation 12(5), 393-403 (2005), Takeda S., Naito T., Hama K., Noma T., Honjo T. Construction of chimaeric processed immunoglobulin genes containing mouse variable and human constant region sequences. Nature 314, 452-454 (1985).

Teixeira M. M., Williams T. J., and Hellewell P. G. Mechanisms and pharmacological modulation of eosniophil accumulation in vivo. Trends Pharmacol. Sci. 16, 418-423 (1995).

Teixeira M. M., Giembycz M. A., Lindsay M. A. and Hellewell P. G. Pertussis toxin reveals distinct early signaling events in platelet-activating factor-, leukotriene B4-, and C5a-induced eosinophil homotypic aggregation in vitro and recruitment in vivo. Blood 89, 4566-4573 (1997).

Teng N. N., Lam K. S., Calvo Riera F., Kaplan H. S. Construction and testing of mouse—human heteromyelomas for human monoclonal antibody production. Proc. Natl. Acad. Sci. 80:23, 7308-7312 (1983).

Tournaire R, Simon M. P, Ie Noble F., Eichmann A., England P, & Pouysségur J. A short synthetic peptide inhibits signal transduction, migration and angiogenesis mediated by Tie2 receptor. *EMBO Reports* 5, 262-267 (2004).

Tsigkos, S., Koutsilieris, M. & Papapetropoulos, A. Angiopoietins in angiogenesis and beyond. Expert Opin. Investig. Drugs. 12, 933-941 (2003).

van der Geer P, Hunter T, Lindberg R A. Receptor protein-tyrosine kinases and their signal transduction pathways. Ann Rev Cell Biol 10, 251-337 (1994).

VanSlyke, P., Alami, J. M. D., Kuliszewski, M. A., Leong-Poi, H., Sefton, M. & Dumont, D. J. Acceleration of diabetic wound healing by an angiopoietin eptidemimetic. eptide mimetic. Tissue Eng Part A 15(6), 1269-1280 (2009).

Voskas D, Jones N, Van Slyke P, Sturk C, Chang W, Haninec A, Babichev Y. O, Tran J, Master Z, Chen S, Ward N, Cruz M, Jones J, Kerbel R. S, Jothy S, Dagnino L, Arbiser J, Klement G, & Dumont D. J. A cyclosporine-sensitive psoriasis-like disease produced in Tie2 transgenic mice. Am J Pathol 166(3), 843-855 (2005).

Voskas D, Babichev Y, Ling L. S, Alami J, Shaked Y, Kerbel R. S, Ciruna B, & Dumont D. J. An eosinophil immune response characterizes the inflammatory skin disease observed in Tie-2 transgenic mice. J Leukoc Biol 84(1): 59-67 (2008).

Ward E. S., Güssow D., Griffiths A. D., Jones P. T., Winter G. I. Binding activities of a repertoire of single immunoglobulin variable domains secreted from *Escherichia coli*. Nature 341(6242):544-6 (1989).

Ward N. L. & Dumont, D. J. The angiopoietins and Tie2/Tek: adding to the complexity of cardiovascular development. Semin. Cell Dev. Biol. 13, 19-27 (2002).

Ward, N. L., Van Slyke, P. & Dumont, D. J. Functional inhibition of secreted angiopoietin: a novel role for angiopoietin 1 in coronary vessel patterning. Biochem. Biophys. Res. Commun. 323, 937-946 (2004).

Ward N. L., Haninec A. L., Van Slyke P., Sled J. G., Sturk C., Henkelman R. M., Wanless I. R. & Dumont D. J. Angiopoietin-1 causes reversible degradation of the portal microcirculation in mice: implications for treatment of liver disease. Am. J. Pathol. 165(3), 889-899 (2004).

Webb D. C., McKenzie A. N., Koskinen A. M. Yang M., Mattes J., and Foster P. S. Integrated signals between IL-13, IL-4, and IL-5 regulate airways hyperreactivity. J. Immunol. 165(1), 108-13 (2000).

Wu X., Zhao R., Li Z., Yao M., Wang H., Han J., Qu S., Chen X., Qian L., Sun Y., Xu Y., Gu J. A novel small peptide as a targeting ligand for receptor tyrosine kinase Tie2. Biochem. Biophys. Res. Commun. 315, 1004-1010 (2004).

Zhao, H., Leu, S. W., Shi, L., Dedaj, R., Zhao, G., Garg, H. G., Shen, L., Lien, E., Fitzgerald, K. A., Shiedlin, A., Shen, H., Quinn, D. A. & Hales, C. A. TLR4 is a negative regulator in noninfectious lung inflammation. J. Immunol. 184, 5308-5314 (2010).

The invention claimed is:

1. A method for reducing eosinophils and/or basophils in an animal in need thereof comprising administering a multimeric form of Tie2 binding peptide monomers to the animal in need thereof, wherein the multimeric form has Tie2 agonist activity, wherein each peptide monomer comprises:
   (i) a T7 peptide (SEQ ID NO:1) or a T7 modified peptide (SEQ ID NO:2);
   (ii) a GA3 peptide (SEQ ID NO:3) or a GA3 modified peptide (SEQ ID NO:4);
   (iii) a T4 peptide (SEQ ID NO:9) or a T4 modified peptide (SEQ ID NO:10);
   (iv) a T6 peptide (SEQ ID NO:7) or a T6 modified peptide (SEQ ID NO:8); or
   (v) a T8 peptide (SEQ ID NO:5) or a T8 modified peptide (SEQ ID NO:6);
   and wherein the Tie2 binding peptide monomers are multimerized via a linking moiety, spacer and/or multimerizing agent.

2. The method of claim 1, for treating atopic dermatitis or allergic rhinitis.

3. The method of claim 2, for treating atopic dermatitis.

4. The method of claim 1, for treating leukemia of eosinophil and/or basophil origin.

5. The method of claim 1, for treating inflammatory bowel disease.

6. The method of claim 1, for treating a parasitic infection.

7. The method of claim 1, for reducing inflammatory cytokine and/or chemokine levels comprising at least one of eotaxin, interleukin (IL)-17, monokine induced by gamma interferon (MIG), IL12/IL23 (p40), IL-9, macrophage inflammatory protein (MIP)-1a, MIP-1b, Regulated on Activation, Normal T Cell Expressed (RANTES) cytokine, tumor necrosis factor (TNF)-α, IL-1β, IL-5, IL-13, and monocyte chemoattractant protein (MCP)-1.

8. The method of claim 7, wherein the inflammatory cytokine and/or chemokine comprises eotaxin.

9. The method of claim 1, wherein the multimeric form is a dimer or tetramer.

10. The method of claim 1, wherein the multiple Tie2 binding peptide monomers are covalently linked to the spacer.

11. The method of claim 10, wherein the spacer comprises polyethylene glycol (PEG).

12. The method of claim 1, wherein the Tie2 binding peptide monomer comprises a T7 peptide as shown in SEQ ID NO:1 or a modified T7 peptide as shown in SEQ ID NO:2.

13. The method of claim 1, wherein the Tie2 binding peptide monomer comprises a GA3 peptide as shown in SEQ ID NO: 3 or a modified GA3 peptide as shown in SEQ ID NO:4.

14. The method of claim 1, wherein the Tie2 binding peptide monomer comprises a peptide selected from the group consisting of a T4 peptide as shown in SEQ ID NO:9, a modified T4 peptide as shown in SEQ ID NO:10, a T6 peptide as shown in SEQ ID NO:7, a modified T6 peptide as shown in SEQ ID NO:8, a T8 peptide as shown in SEQ ID NO:5 and a T8 modified peptide as shown in SEQ ID NO:6.

15. The method of claim 1, wherein the multimeric form is a dimer, comprising: (a) a first Tie2 binding peptide monomer; (b) a second Tie2 binding peptide monomer; and (c) a linking moiety connecting said first and second Tie2 binding peptide monomers, wherein said peptide dimer binds to and activates the Tie2 receptor.

16. The method of claim 15, wherein the first Tie2 binding peptide monomer and/or the second Tie2 binding peptide monomer is a T7 peptide as shown in SEQ ID NO:1 or a modified T7 peptide as shown in SEQ ID NO:2.

17. The method of claim 15, wherein the linking moiety comprises one or more water soluble polymers covalently bound to the first Tie2 binding peptide monomer and the second Tie2 binding peptide monomer.

18. The method of claim 17, wherein the water soluble polymer is a polyethylene glycol (PEG).

19. The method of claim 1, wherein the multimeric form comprises a peptide tetramer, comprising: (a) a first Tie2 binding peptide monomer; (b) a second Tie2 binding peptide monomer; (c) a third Tie2 binding peptide monomer; (d) a fourth Tie2 binding peptide monomer; and (e) a linking moiety connecting said first, second, third and fourth Tie2 binding peptide monomers, wherein said peptide tetramer binds to and activates the Tie2 receptor.

20. The method of claim 19, wherein the first, second, third and fourth Tie2 binding peptide monomers are T7 peptides as shown in SEQ ID NO:1 or a modified T7 peptide as shown in SEQ ID NO:2.

21. The method of claim 19, wherein the linking moiety comprises one or more soluble polymers covalently bound to the first, second, third and fourth Tie2 binding peptide monomers.

22. The method of claim 19, wherein the linking moiety is a branched chain water soluble polymer.

23. The method of claim 22, wherein the water soluble polymer is a branched chain polyethylene glycol (PEG).

24. The method of claim 23, wherein the PEG has a molecular weight in a range of about 3,000 Daltons to about 20,000 Daltons.

25. The method of claim 1, wherein the multimeric form of Tie2 binding peptide monomers is administered topically, systemically, intranasally or by inhalation.

26. The method of claim 1, wherein the animal is a human.

* * * * *

SEQUENCE LISTING

```
<160> NUMBER OF SEQ ID NOS: 10

<210> SEQ ID NO 1
<211> LENGTH: 7
<212> TYPE: PRT
<213> ORGANISM: Artificial Sequence
<220> FEATURE:
<223> OTHER INFORMATION: Synthetic construct

<400> SEQUENCE: 1
```

```
His His His Arg His Ser Phe
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic construct

<400> SEQUENCE: 2

Cys His His His Arg His Ser Phe
1               5

<210> SEQ ID NO 3
<211> LENGTH: 22
<212> TYPE: PRT
<213> ORGANISM: Artificial Sequence
<220> FEATURE:
<223> OTHER INFORMATION: Synthetic construct

<400> SEQUENCE: 3

Trp Thr Ile Ile Gln Arg Arg Glu Asp Gly Ser Val Asp Phe Gln Arg
1               5                   10                  15

Thr Trp Lys Glu Tyr Lys
            20

<210> SEQ ID NO 4
<211> LENGTH: 23
<212> TYPE: PRT
<213> ORGANISM: Artificial Sequence
<220> FEATURE:
<223> OTHER INFORMATION: Synthetic construct

<400> SEQUENCE: 4

Cys Trp Thr Ile Ile Gln Arg Arg Glu Asp Gly Ser Val Asp Phe Gln
1               5                   10                  15

Arg Thr Trp Lys Glu Tyr Lys
            20

<210> SEQ ID NO 5
<211> LENGTH: 7
<212> TYPE: PRT
<213> ORGANISM: Artificial Sequence
<220> FEATURE:
<223> OTHER INFORMATION: Synthetic construct

<400> SEQUENCE: 5

His Pro Trp Leu Thr Arg His
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic construct

<400> SEQUENCE: 6

Cys His Pro Trp Leu Thr Arg His
1               5

<210> SEQ ID NO 7
<211> LENGTH: 7
<212> TYPE: PRT
```

```
<213> ORGANISM: Artificial Sequence
<220> FEATURE:
<223> OTHER INFORMATION: Synthetic construct

<400> SEQUENCE: 7

Lys Leu Trp Val Ile Pro Lys
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic construct

<400> SEQUENCE: 8

Cys Lys Leu Trp Val Ile Pro Lys
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic construct

<400> SEQUENCE: 9

Asn Leu Leu Met Ala Ala Ser
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic construct

<400> SEQUENCE: 10

Cys Asn Leu Leu Met Ala Ala Ser
1               5
```